United States Patent [19]

Chandler

[11] Patent Number: 5,607,863

[45] Date of Patent: Mar. 4, 1997

[54] BARRIER-CONTROLLED ASSAY DEVICE

[75] Inventor: Howard M. Chandler, Yarmouth, Me.

[73] Assignee: SmithKline Diagnostics, Inc., San Jose, Calif.

[21] Appl. No.: 163,860

[22] Filed: Dec. 7, 1993

Related U.S. Application Data

[63] Continuation-in-part of Ser. No. 40,430, Mar. 31, 1993, which is a continuation-in-part of Ser. No. 888,831, May 27, 1992, abandoned, which is a continuation-in-part of Ser. No. 706,639, May 29, 1991.

[51] Int. Cl.$^6$ .................. G01N 33/543; G01N 33/558
[52] U.S. Cl. .................. 436/518; 422/56; 422/57; 422/58; 422/61; 422/104; 435/7.92; 435/7.93; 435/7.94; 435/805; 435/969; 435/970; 436/165; 436/170; 436/514; 436/810
[58] Field of Search ................ 436/518, 165, 436/170, 810, 514; 435/310, 805, 969, 970, 7.92, 7.93, 7.94; 422/56, 57, 58, 61, 104

[56] References Cited

U.S. PATENT DOCUMENTS

| | | |
|---|---|---|
| 3,723,064 | 3/1973 | Liotta . |
| 3,798,004 | 3/1974 | Zerachia et al. . |
| 3,888,629 | 6/1975 | Bagshawe . |
| 3,915,647 | 10/1975 | Wright . |
| 3,933,594 | 1/1976 | Milligan . |
| 3,966,897 | 6/1976 | Renn et al. . |
| 3,985,867 | 10/1976 | Redshaw . |
| 3,990,850 | 11/1976 | Friedman et al. . |
| 3,993,451 | 11/1976 | Verbeck . |
| 3,996,006 | 12/1976 | Pagano . |
| 4,018,662 | 4/1977 | Ruhenstroth-Bauer et al. . |
| 4,094,647 | 6/1978 | Deutsch et al. . |
| 4,108,729 | 8/1978 | Mennen . |
| 4,110,079 | 8/1978 | Schaeffer . |
| 4,168,146 | 9/1979 | Grubb et al. . |

(List continued on next page.)

FOREIGN PATENT DOCUMENTS

| | | |
|---|---|---|
| 0443231 | 8/1981 | European Pat. Off. . |
| 0068310 | 11/1982 | European Pat. Off. . |
| 0183442 | 6/1986 | European Pat. Off. . |
| 0191640 | 8/1986 | European Pat. Off. . |
| 0225054 | 6/1987 | European Pat. Off. . |
| 0238012 | 9/1987 | European Pat. Off. . |
| 0250137 | 12/1987 | European Pat. Off. . |
| 0262328 | 4/1988 | European Pat. Off. . |
| 026876 | 6/1988 | European Pat. Off. . |
| 0323605 | 7/1988 | European Pat. Off. . |
| 0279097 | 8/1988 | European Pat. Off. . |
| 0284232 | 9/1988 | European Pat. Off. . |
| 0291194 | 11/1988 | European Pat. Off. . |
| 0296724 | 12/1988 | European Pat. Off. . |
| 0299428 | 1/1989 | European Pat. Off. . |

(List continued on next page.)

*Primary Examiner*—James C. Housel
*Assistant Examiner*—Christopher L. Chi
*Attorney, Agent, or Firm*—William H. May; Gary T. Hampson

[57] ABSTRACT

An assay device for detection and/or determination of an analyte in a test sample uses a barrier containing an aperture to control the application of reagents to the device for greater reproducibility of results. In its simplest form, the device comprises: (1) a chromatographic medium having a first end, a second end, and first and second surfaces, and having a specific binding partner for the analyte immobilized thereto in a detection zone; (2) at least one absorber in operable contact with at least one of the first and second ends; and (3) a substantially fluid-impermeable barrier adjacent to the first surface of the chromatographic medium, the barrier having at least one aperture therethrough for application of liquid to the chromatographic medium, the barrier at least partially blocking application of liquid to the chromatographic medium. The device can be adapted for sandwich or competitive assays and can be used to perform amplified assays, such as those using silver amplification or enzyme amplification. Various arrangements of components within the device are possible, and elements such as filters can be accommodated.

85 Claims, 9 Drawing Sheets

U.S. PATENT DOCUMENTS

| | | |
|---|---|---|
| 4,189,304 | 2/1980 | Adams, Jr. et al. . |
| 4,223,089 | 9/1980 | Rothe et al. . |
| 4,246,339 | 1/1981 | Cole et al. . |
| 4,256,693 | 3/1981 | Kondo et al. .............................. 422/56 |
| 4,299,916 | 11/1981 | Litman et al. . |
| 4,313,734 | 2/1982 | Leuvering . |
| 4,333,733 | 6/1982 | Sanford et al. . |
| 4,365,970 | 12/1982 | Lawrence et al. . |
| 4,366,241 | 12/1982 | Tom et al. . |
| 4,376,110 | 3/1983 | David et al. . |
| 4,391,904 | 7/1983 | Litman et al. . |
| 4,425,438 | 1/1984 | Bauman et al. . |
| 4,427,769 | 1/1984 | Adlercreutz et al. . |
| 4,435,504 | 3/1984 | Zuk et al. . |
| 4,442,204 | 4/1984 | Greenquist et al. . |
| 4,444,193 | 4/1984 | Fogt et al. . |
| 4,446,232 | 5/1984 | Liotta . |
| 4,447,526 | 5/1984 | Rupchock et al. . |
| 4,447,529 | 5/1984 | Greenquist et al. . |
| 4,459,358 | 7/1984 | Berke . |
| 4,461,829 | 7/1984 | Greenquist . |
| 4,474,878 | 10/1984 | Halbert et al. . |
| 4,477,575 | 10/1984 | Vogel et al. . |
| 4,517,288 | 5/1985 | Giegel et al. . |
| 4,533,629 | 8/1985 | Litman et al. . |
| 4,582,811 | 4/1986 | Pucci et al. . |
| 4,594,327 | 6/1986 | Zuk . |
| 4,623,461 | 11/1986 | Hossom et al. . |
| 4,629,690 | 12/1986 | Weng et al. . |
| 4,642,285 | 2/1987 | Halbert et al. . |
| 4,668,619 | 5/1987 | Greenquist et al. . |
| 4,678,757 | 7/1987 | Rapkin et al. . |
| 4,683,197 | 7/1987 | Gallati . |
| 4,690,907 | 9/1987 | Hibino et al. . |
| 4,693,834 | 9/1987 | Hossom . |
| 4,703,017 | 10/1987 | Campbell et al. . |
| 4,717,656 | 1/1988 | Swanljung . |
| 4,738,823 | 4/1988 | Engelmann . |
| 4,740,468 | 4/1988 | Weng et al. . |
| 4,752,562 | 6/1988 | Sheiman et al. . |
| 4,761,381 | 8/1988 | Blatt et al. . |
| 4,775,636 | 10/1988 | Moeremans et al. . |
| 4,780,280 | 10/1988 | Berger et al. . |
| 4,786,594 | 11/1988 | Khanna et al. . |
| 4,789,526 | 12/1988 | Matkovich . |
| 4,789,629 | 12/1988 | Baker et al. . |
| 4,790,979 | 12/1988 | Terminiello et al. . |
| 4,797,260 | 1/1989 | Parker . |
| 4,803,170 | 2/1989 | Stanton et al. . |
| 4,806,311 | 2/1989 | Greenquist . |
| 4,806,312 | 2/1989 | Greenquist . |
| 4,810,470 | 3/1989 | Burkhardt et al. . |
| 4,814,142 | 3/1989 | Gleisner . |
| 4,816,224 | 3/1989 | Vogel et al. . |
| 4,818,677 | 4/1989 | Hay-Kaufman et al. . |
| 4,826,759 | 5/1989 | Guire et al. . |
| 4,837,373 | 6/1989 | Gunkel et al. . |
| 4,837,395 | 6/1989 | Leeder et al. . |
| 4,843,000 | 6/1989 | Litman et al. . |
| 4,853,335 | 8/1989 | Olsen et al. . |
| 4,855,240 | 8/1989 | Rosenstein et al. . |
| 4,857,453 | 8/1989 | Ullman et al. . |
| 4,859,612 | 8/1989 | Cole et al. . |
| 4,861,711 | 8/1989 | Friesen et al. . |
| 4,868,108 | 9/1989 | Bahar et al. . |
| 4,876,067 | 10/1989 | Deneke et al. . |
| 4,877,586 | 10/1989 | Devaney, Jr. et al. . |
| 4,879,215 | 11/1989 | Weng et al. . |
| 4,883,764 | 11/1989 | Kloepfer . |
| 4,900,663 | 2/1990 | Wie et al. . |
| 4,912,034 | 3/1990 | Kalra et al. . |
| 4,916,056 | 4/1990 | Brown, III et al. . |
| 4,916,078 | 4/1990 | Klose et al. . |
| 4,918,025 | 4/1990 | Grenner . |
| 4,920,046 | 4/1990 | McFarland et al. . |
| 4,938,927 | 7/1990 | Kelton et al. . |
| 4,939,098 | 7/1990 | Suzuki et al. . |
| 4,943,522 | 7/1990 | Eisinger et al. . |
| 4,952,517 | 8/1990 | Bahar . |
| 4,956,275 | 9/1990 | Zuk et al. . |
| 4,956,302 | 9/1990 | Gordon et al. . |
| 4,959,307 | 9/1990 | Olson . |
| 4,960,691 | 10/1990 | Gordon et al. . |
| 4,963,325 | 10/1990 | Lennon et al. . |
| 4,963,468 | 10/1990 | Olson . |
| 4,977,078 | 12/1990 | Niimura et al. . |
| 4,981,786 | 1/1991 | Dafforn et al. . |
| 4,999,285 | 3/1991 | Stiso . |
| 4,999,287 | 3/1991 | Allen et al. . |
| 5,006,464 | 4/1991 | Chu et al. . |
| 5,006,474 | 4/1991 | Horstman et al. . |
| 5,030,555 | 7/1991 | Clemmons . |
| 5,030,558 | 7/1991 | Litman et al. . |
| 5,039,607 | 8/1991 | Skold et al. . |
| 5,051,237 | 9/1991 | Grenner et al. . |
| 5,071,746 | 12/1991 | Wilk et al. . |
| 5,073,484 | 12/1991 | Swanson et al. . |
| 5,075,078 | 12/1991 | Osikowicz et al. . |
| 5,079,142 | 1/1992 | Coleman et al. . |
| 5,079,174 | 1/1992 | Buck et al. . |
| 5,085,987 | 2/1992 | Olson . |
| 5,085,988 | 2/1992 | Olson . |
| 5,096,809 | 3/1992 | Chen et al. . |
| 5,100,619 | 3/1992 | Baker et al. . |
| 5,104,811 | 4/1992 | Berger et al. . |
| 5,104,812 | 4/1992 | Kurn et al. . |
| 5,106,582 | 4/1992 | Baker . |
| 5,106,758 | 4/1992 | Adler et al. . |
| 5,110,550 | 5/1992 | Schlipfenbacher et al. . |
| 5,114,673 | 5/1992 | Berger et al. . |
| 5,114,862 | 5/1992 | Brenneman . |
| 5,120,643 | 6/1992 | Ching et al. . |
| 5,120,662 | 6/1992 | Chan et al. . |
| 5,132,208 | 7/1992 | Freitag et al. . |
| 5,135,872 | 8/1992 | Pouletty et al. . |
| 5,135,873 | 8/1992 | Patel et al. . |
| 5,137,804 | 8/1992 | Greene et al. . |
| 5,137,808 | 8/1992 | Ullman et al. . |
| 5,141,850 | 8/1992 | Cole et al. . |
| 5,156,952 | 10/1992 | Litman et al. . |
| 5,158,869 | 10/1992 | Pouletty et al. . |
| 5,160,486 | 11/1992 | Schlipfenbacher et al. . |
| 5,162,237 | 11/1992 | Messenger et al. . |
| 5,164,294 | 11/1992 | Skold et al. . |
| 5,177,021 | 1/1993 | Kondo . |
| 5,182,191 | 1/1993 | Fan et al. . |
| 5,185,127 | 2/1993 | Vonk . |
| 5,188,939 | 2/1993 | Mangold et al. . |
| 5,188,966 | 2/1993 | Eikmeier et al. . |
| 5,202,267 | 4/1993 | Ditlow et al. . |
| 5,202,268 | 4/1993 | Kuhn et al. . |
| 5,209,904 | 5/1993 | Forney et al. . |
| 5,223,436 | 6/1993 | Freitag et al. . |
| 5,234,813 | 8/1993 | McGeehan et al. . |
| 5,248,619 | 9/1993 | Skold et al. . |
| 5,256,372 | 10/1993 | Brooks et al. . |
| 5,258,163 | 11/1993 | Krause et al. . |
| 5,260,193 | 11/1993 | Olson . |
| 5,260,222 | 11/1993 | Patel et al. . |
| 5,264,180 | 11/1993 | Allen et al. . |
| 5,275,785 | 1/1994 | May et al. . |
| 5,278,079 | 1/1994 | Gubinski et al. . |

| | | |
|---|---|---|
| 5,308,580 | 5/1994 | Clark . |
| 5,314,804 | 5/1994 | Boguslaski et al. ............... 435/12 |
| 5,415,994 | 5/1995 | Imrich et al. ............... 435/5 |

FOREIGN PATENT DOCUMENTS

| | | |
|---|---|---|
| 0297292 | 1/1989 | European Pat. Off. . |
| 0306772 | 3/1989 | European Pat. Off. . |
| 0310406 | 4/1989 | European Pat. Off. . |
| 0322340 | 6/1989 | European Pat. Off. . |
| 0319294 | 6/1989 | European Pat. Off. . |
| 0339450 | 11/1989 | European Pat. Off. . |
| 0415679 | 3/1991 | European Pat. Off. . |
| 0516095 | 5/1992 | European Pat. Off. . |
| 0560410 | 9/1993 | European Pat. Off. . |
| 2016687 | 9/1979 | United Kingdom . |
| 2204398 | 11/1988 | United Kingdom . |
| WO89/03992 | 5/1989 | WIPO . |
| WO90/5906 | 5/1990 | WIPO . |
| WO91/01003 | 1/1991 | WIPO . |
| WO91/19980 | 12/1991 | WIPO . |
| WO92/01226 | 1/1992 | WIPO . |
| WO93/03176 | 2/1993 | WIPO . |

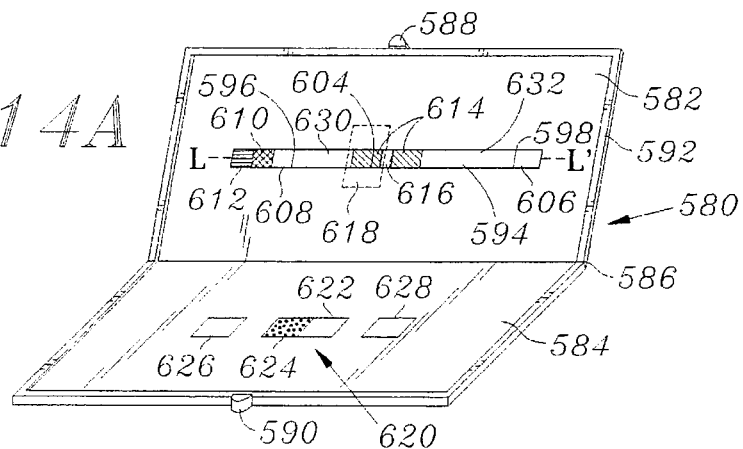
FIG. 14A
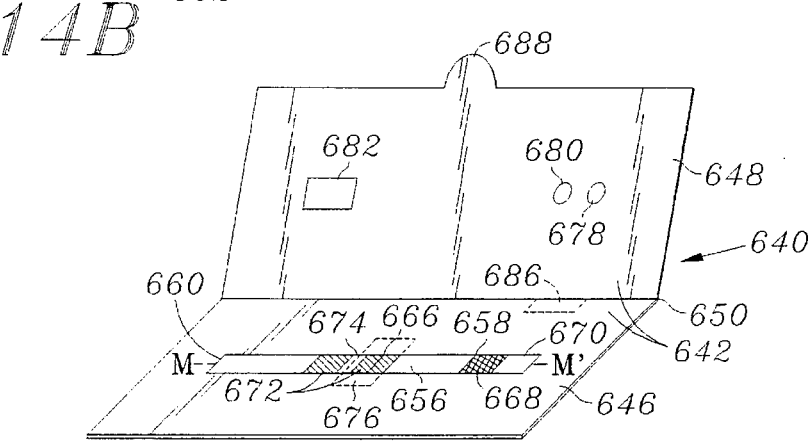
FIG. 14B
FIG. 15A
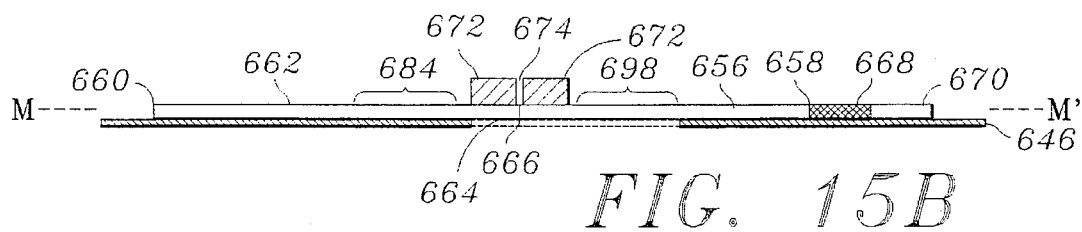
FIG. 15B

BARRIER-CONTROLLED ASSAY DEVICE

CROSS-REFERENCES

This application is a continuation-in-part of U.S. application Ser. No. 08/040,430 by Howard M. Chandler et al., filed Mar. 31, 1993, and entitled "Assay Device," which was itself a continuation-in-part of U.S. application Ser. No. 07/888,831, by Howard M. Chandler, filed May 27, 1992, now abandoned and also entitled "Assay Device," which was in turn a continuation-in-part of U.S. application Ser. No. 07/706,639 by Howard M. Chandler, filed May 29, 1991, and entitled "Assay Device." All three of these preceding applications are incorporated herein in their entirety by this reference.

TABLE OF CONTENTS

For convenience, the following Table of Contents is provided:
BACKGROUND OF THE INVENTION
SUMMARY
BRIEF DESCRIPTION OF THE DRAWINGS
DESCRIPTION
Definitions
  I. BARRIER-CONTROLLED ASSAY DEVICES
    A. Principles of the Method
    B. Elements Common to Devices According to the Present Invention
      1. The Chromatographic Medium
      2. Absorbers
      3. Other Fluid-Carrying Elements
      4. Filters
      5. Opposable Components
      6. Substantially Fluid-Impermeable Barrier
      7. Labeled Components
    C. Assay Devices Employing Vertical/Lateral Flow
      1. Basic Assay Device Employing Vertical/Lateral Flow
      2. One-Component Assay Device With Applicator Adjacent to Barrier
      3. Two-Component Device With Applicator on First Opposable Component
      4. Two-Component Device With Applicator on Second Opposable Component
      5. Devices With Filter to Remove Particulates
        a. Device With Filter in Fluid Path After Introduction of Resolubilized Labeled Specific Binding Partner
        b. Device With Filter in Fluid Path Before Introduction of Resolubilized Labeled Specific Binding Partner
      6. Device for Extraction of a Swab
      7. Devices for Competitive Immunoassays
    D. Non-Isotropic Flow Devices
    E. Devices Employing Direct Absorption of Analyte to the Chromatographic Medium
  II. SEQUENTIAL IMMUNOCHROMATOGRAPHY
  III. AMPLIFIED IMMUNOCHROMATOGRAPHY
    A. Principles of Silver Amplification
    B. Devices Employing Silver Amplification
      1. Device With Silver Salt Incorporated in Applicator on Second Opposable Component
      2. Device With Two-Sector Applicator to Provide Wash
      3. Device with Base Panel and Insert
  IV. ENZYME IMMUNOCHROMATOGRAPHY
    A. Principles of Enzyme Labeling
      1. Choice of Enzymes and Substrates
      2. Coupling of Enzymes to Members of Specific Binding Pair
    B. Devices Suitable for Enzyme Immunochromatography
Example 1—Example Showing Lack of Reaction With Sample Negative for Giardia
Example 2—Experiment Showing Positive Detection of Giardia
Example 3—Assay Device for Streptococcus A
Example 4—Device for Enzyme Immunochromatography
ADVANTAGES OF THE INVENTION

BACKGROUND OF THE INVENTION

This invention is directed to test devices for determination of characteristics of samples, unitized housings, and kits incorporating the test devices and housings, and methods of determining the characteristics of samples using the test devices and housings.

Among the many analytical systems used for detection and/or determination of analytes, particularly analytes of biological interests, are chromatographic assay systems. Among the analytes frequently assayed with such systems are:

(1) hormones, such as human chorionic gonadotropin (hCG), frequently assayed as a marker of human pregnancy;

(2) antigens, particularly antigens specific to bacterial, viral, and protozoan pathogens, such as Streptococcus, hepatitis virus, and Giardia;

(3) antibodies, particularly antibodies induced as a result of infection with pathogens, such as antibody to the bacteria *Helicobacter pylori* and to human immunodeficiency virus (HIV);

(4) other proteins, such as hemoglobin, frequently assayed in determinations of fecal occult blood, an early indicator of gastrointestinal disorders such as colon cancer;

(5) enzymes, such as aspartate aminotransferase, lactate dehydrogenase, alkaline phosphatase, and glutamate dehydrogenase, frequently assayed as indicators of physiological function and tissue damage;

(6) drugs, both therapeutic drugs such as antibiotics, tranquilizers, and anticonvulsants, and illegal drugs of abuse, such as cocaine, heroin, and marijuana;

(7) environmental pollutants such as pesticides and aromatic hydrocarbons; and (8) vitamins.

Such chromatographic systems are frequently used by physicians and medical technicians for rapid in-office diagnosis and therapeutic monitoring of a variety of conditions and disorders. They are also increasingly used by patients themselves for at-home monitoring of such conditions and disorders.

Among the most important of such systems are the "thin layer" systems in which a solvent moves across a thin, flat absorbent medium. Among the most important of tests that can be performed with such thin layer systems are immunoassays, which depend on the specific interaction between an antigen or hapten and a corresponding antibody. The use of immunoassays as a means of testing for the presence and/or amount of clinically important molecules has been known for some time. As early as 1956, J. M. Singer reported the use of an immune-based latex agglutination test for detecting a factor associated with rheumatoid arthritis (Singer et al., Am. *J. Med.* 22:888–892 (1956)).

Among the chromatographic techniques used in conjunction with immunoassays is a procedure known as immunochromatography. In general, this technique uses a disclosing reagent or particle that has been linked to an antibody to the molecule to be assayed, forming a conjugate. This conjugate is then mixed with a specimen, and if the molecule to be assayed is present in the specimen, the disclosing reagent-linked antibodies bind to the molecule to be assayed, thereby giving an indication that the molecule to be assayed is present. The disclosing reagent or particle can be identifiable by color, magnetic properties, radioactivity, specific reactivity with another molecule, or another physical or chemical property. The specific reactions that are employed vary with the nature of the molecule being assayed and the sample to be tested.

Immunochromatographic assays fall into two principal categories: "sandwich" and "competitive," according to the nature of the antigen-antibody complex to be detected and the sequence of reactions required to produce that complex. The antigen to be detected can itself be an antibody, such as in serological assays for *H. pylori*-specific antibody. In such cases, the antibody to be detected can be bound to a specific antigen. Alternatively, the antigen to be detected can be detected indirectly by using a labeled second antibody that binds the first antibody to the analyte to be detected.

In general, the sandwich immunochromatographic procedures call for mixing the sample that may contain the analyte to be assayed with antibodies to the analyte. These antibodies are mobile and typically are linked to a label or a disclosing reagent, such as dyed latex, a colloidal metal sol, or a radioisotope. This mixture is then applied to a chromatographic medium containing a band or zone of immobilized antibodies to the analyte of interest. The chromatographic medium often is in the form of a strip resembling a dipstick. When the complex of the molecule to be assayed and the labeled antibody reaches the zone of the immobilized antibodies on the chromatographic medium, binding occurs and the bound labeled antibodies are localized at the zone. This indicates the presence of the molecule to be assayed. This technique can be used to obtain quantitative or semi-quantitative results.

Examples of sandwich immunoassays performed on test strips are described by U.S. Pat. No. 4,168,146 to Grubb et al. and U.S. Pat. No. 4,366,241 to Tom et al., both of which are incorporated herein by this reference.

In competitive immunoassays, the label is typically a labeled analyte or analyte analogue which competes for binding of an antibody with any unlabeled analyte present in the sample. Competitive immunoassays are typically used for detection of analytes such as haptens, each hapten being monovalent and capable of binding only one antibody molecule. Examples of competitive immunoassay devices are those disclosed by U.S. Pat. No. 4,235,601 to Deutsch et al., U.S. Pat. No. 4,442,204 to Liotta, and U.S. Pat. No. 5,208,535 to Buechler et al., all of which are incorporated herein by this reference.

Although useful, currently available chromatographic techniques using test strips have a number of drawbacks. Many samples, such as fecal samples, contain particulate matter that can clog the pores of the chromatographic medium, greatly hindering the immunochromatographic process. Other samples, such as blood, contain cells and colored components that make it difficult to read the test. Even if the sample does not create interference, it is frequently difficult with existing chromatographic test devices to apply the sample to the chromatographic medium so that the sample front moves uniformly through the chromatographic medium to ensure that the sample reaches the area where binding is to occur in a uniform, straight-line manner. Other problems exist with currently-available test strips because of the nature of the sample to be assayed or the assay to be carried out. In many currently-available test strips, the time of passage of the specimen, from the point of application to passage past the specific capture band on the solid phase, frequently results in an undesirable time delay in obtaining results. In addition, valuable specimen and reagents may be lost in the dead volume of the elements in the path to the capture zone. Additionally, currently available immunochromatographic test strip designs are unsuitable for carrying out enzyme immunoassays, because such designs typically leave a background of active enzyme in the test strip, which can create a high background in the test strip when substrate is added and can interfere with detection of analyte, particularly at low concentrations.

With currently-available designs, it is also impractical to perform washing steps which are frequently desirable to improve sensitivity and to reduce background. Also, it is difficult, and in many cases impossible, to carry out preincubation steps within the device. Additionally, there is a need for an effective assay for a number of antigens, such as *Chlamydia trachomatis* lipopolysaccharide (LPS) antigen, that bind strongly and nonspecifically to materials commonly used as a solid phase in test strips.

Sample preparation and waste generation are responsible for other problems with currently available devices and techniques for immunochromatography. The increased prevalence of diseases spread by infected blood and blood fractions, such as AIDS and hepatitis, has exacerbated these problems. It is rarely possible to apply a sample (such as feces) or a sampling device (such as a throat swab) directly to the chromatographic medium. Several extraction and pretreatment reactions are usually required before the sample can be applied to the chromatographic medium. These reactions are typically carried out by the physician or technician performing the test in several small vessels, such as test tubes or microfuge tubes requiring the use of transfer devices such as pipettes. Each of these devices is then contaminated and must be disposed of using special precautions so that workers or people who may inadvertently come into contact with the waste do not become contaminated. Still another limitation in chromatographic devices currently available for use by the physician or technician is their inability to perform two-directional and two-dimensional chromatography. These techniques have long been known to be powerful analytical tools, but their complexity relative to simple unidirectional chromatography has made it difficult to apply them to test strip devices in the physician's office or a clinical laboratory.

Accordingly, there is a need for an improved assay device capable of handling a broad range of chromatographic assays. Such a device should be able to handle all types of immunoassays, including both sandwich and competitive immunoassays as well as other types of assays using chromatography. Such a device should be capable of receiving a possibly contaminated sample or a sample preparation device directly so as to eliminate the need for extraction vessels and transfer devices. Such a device, preferably in the form of a test strip, should also be capable of performing immunochromatographic assays on colored samples or samples containing particulates without interference and should be able to deliver the sample to the chromatographic medium uniformly and evenly to improve accuracy and precision of the tests. Additionally, such an improved test strip should be capable of performing two-directional or two-dimensional chromatography when used in clinical laboratories or physicians offices. Moreover, such a test strip should minimize the time delay experienced in the performance of the assay and also minimize the dead volume in order to provide maximum economy in the use of samples and reagents. Finally, such an improved test strip should provide lower background for enzymatic immunoassays.

SUMMARY

I have developed an assay device that meets these needs, and provides improved and more reproducible assays for analytes of biological interest, while simplifying the performance of the assay. The device can perform all types of immunoassays, including sandwich immunoassays and competitive immunoassays. The device can also perform amplified immunoassays in which a signal is amplified either by enzymatic action or by the use of silver to amplify a signal generated by a gold label. The device can also be used to assay analytes that bind directly to a chromatographic medium, such as lipopolysaccharides.

Assay devices according to the present invention can be constructed with one component, but, preferably, are constructed with two or more opposable components. When constructed with two or more opposable components, the assay device makes use of pressure to transfer fluid from one opposable component to another opposable component, and also to drive fluid through the chromatographic medium and elements such as filters. The use of pressure not only speeds up the operative of the device, but allows the performance of additional steps, such as extraction steps to remove interfering particulate components, within a single device. The pressure is generated by placing the opposable components together with engagers such as interlocking elements on each of the opposable components. Preferably, a predetermined amount of pressure is applied to ensure the optimum performance of each step of the assay procedure.

Devices with two or more opposable components can additionally incorporate an insert for application of reagents. This arrangement is particularly useful in performing amplified immunoassays.

Additionally, the device can perform other types of specific binding assays, such as: (1) assays based on the affinity of specific binding proteins or glycoproteins such as lectins, hormone receptors, or viral receptors for their specific ligands; (2) assays based on the affinity of enzymes for their corresponding substrates or inhibitors; or (3) assays based on the affinity of a nucleic acid (DNA or RNA) segment for a complementary nucleic acid segment according to the Watson-Crick base pairing rules.

In a basic, one-component form, a device according to the present invention suitable for performing a sandwich immunoassay comprises:

(1) a chromatographic medium having a first end, a second end, and first and second surfaces, and having a specific binding partner for the analyte immobilized thereto in a detection zone;

(2) at least one absorber in operable contact with at least one of the first and second ends; and (3) a substantially fluid-impermeable barrier adjacent to the first surface of the chromatographic medium, the barrier having at least one aperture therethrough for application of liquid to the chromatographic medium, the barrier at least partially blocking application of liquid to the chromatographic medium.

The chromatographic medium, absorbers, barrier, and aperture are configured such that liquid applied to the barrier is drawn through the chromatographic medium by the at least one absorber so that an analyte and a detection reagent for the analyte can form a ternary complex at the detection zone on the chromatographic medium.

This device can be used in a method for detecting an analyte that comprises:

(1) mixing the sample with an aqueous solution of a labeled detection reagent for the analyte to form a solution containing the sample and the labeled detection reagent;

(2) applying the solution containing the sample and the labeled detection reagent to the aperture of the assay device;

(3) allowing the solution containing the sample and the labeled detection reagent to the analyte to flow through at least the portion of the chromatographic medium including the detection zone; and (4) detecting and/or determining the analyte in the test sample by observing and/or measuring the labeled detection reagent bound at the detection zone.

A similar one-component device includes an additional element, an applicator adjacent to the barrier. The applicator contains a labeled detection reagent for the analyte in a form that can be resolubilized by the addition of an aqueous liquid to the applicator. The applicator is positioned such that the barrier is located between the applicator and the chromatographic medium, and such that a sample applied to the applicator is drawn through the aperture after resolubilizing the specific binding partner and then is drawn through the chromatographic medium by the at least one absorber so that the analyte and the detection reagent for the analyte can form a ternary complex at the detection zone on the chromatographic medium. Similar principles of operation apply to other devices according to the present invention, both one-component and two-component. The order of steps can be varied as necessary to allow the sample and other reagents, such as a labeled specific binding partner for the analyte, to be applied to and migrate through the chromatographic medium.

A basic, two-component form of the device comprises: (1) a first opposable component including:

(a) a chromatographic medium having a first end, a second end, and first and second surfaces, and having a specific binding partner for the analyte immobilized thereon in a detection zone;

(b) at least one absorber in operable contact with at least one of the first and second ends of the chromatographic medium; and (c) a substantially fluid-impermeable barrier adjacent to the first surface of the chromatographic medium and having an aperture for application of liquid to the chromatographic medium, the barrier at least partially blocking application of liquid to the chromatographic medium; and (2) a second opposable component to apply at least one reactant directly or indirectly to the chromatographic medium through the aperture. The first and second opposable components are configured so that bringing the first and second opposable components into opposition results in the second opposable component applying at least one reactant directly or indirectly to the chromatographic medium through the aperture.

A more elaborate version of such a two-component assay device comprises:

(1) a first opposable component including:
  (a) a chromatographic medium having a first end, a second end, and first and second surfaces, and having a specific binding partner for the analyte immobilized thereon in a detection zone;
  (b) at least one absorber in operable contact with at least one of the first and second ends of the chromatographic medium;
  (c) a substantially fluid-impermeable barrier adjacent to the first surface of the chromatographic medium and having an aperture for application of liquid to the chromatographic medium, the barrier at least partially blocking application of liquid to the chromatographic medium; and
  (d) an applicator adjacent to the barrier, the applicator containing a labeled detection reagent for the analyte in a form that can be resolubilized by the addition of an aqueous liquid to the applicator; and
(2) a second opposable component including a sample preparation zone.

The applicator is positioned such that the barrier is located between the applicator and the chromatographic medium and such that an aqueous liquid applied to the applicator is drawn through the aperture after resolubilizing the detection reagent and then is drawn through the chromatographic medium by the at least one absorber so that the analyte and the labeled detection reagent can form a ternary complex at the detection zone on the chromatographic medium. The first and second opposable components are configured so that bringing the first and second opposable components into opposition results in the sample preparation zone being in contact with the applicator so that sample in the sample preparation zone is applied to the applicator for resolubilization of the resolubilizable detection reagent and chromatography through the chromatographic medium.

In a similar device, the applicator is transferred to the second opposable component to which the sample is applied.

Another version of a two-component device according to the present invention incorporates a filter for removing particulates adjacent to the substantially fluid-impermeable barrier on the first opposable component, with an applicator containing a resolubilizable labeled specific binding partner for the analyte on the second opposable component. In an alternative arrangement, the applicator can be located on the first opposable component and the filter positioned so that sample applied to the first opposable component passes through the filter before reaching the applicator.

Another version of the device incorporates a second substantially fluid-impermeable barrier adjacent to a first portion of the applicator, and a distribution membrane adjacent to the second barrier and in operable contact with a second portion of the applicator not adjacent so that fluid can flow from the distribution membrane to the applicator around the second barrier. In this version of the device, the second opposable component includes a receptacle for a swab containing a test sample.

In another version of the device adapted to receive a swab on the second opposable component, the first opposable component includes a distribution membrane adjacent to the first substantially fluid-impermeable barrier to direct fluid to the first aperture in the first substantially fluid-impermeable barrier, a second substantially fluid-impermeable barrier adjacent to a central portion of the distribution membrane, an applicator containing a labeled specific binding partner to the analyte in resolubilizable form and positioned adjacent to the barrier membrane so that fluid can flow from the applicator around the second barrier to the portion of the distribution membrane to which the second substantially fluid-impermeable barrier is not directly adjacent, and a surface barrier containing a second aperture therethrough for application of liquid to the applicator.

Another version of a two-component device according to the present invention and suitable for performing a sandwich immunoassay uses non-isotropic flow. This device comprises:

(1) a first opposable component including:
  (a) a chromatographic medium having a first end and a second end and first and second surfaces, and having immobilized thereon in separate discrete and non-overlapping zones:
    (i) a detection zone of a specific binding partner to the analyte; and
    (ii) a control zone of analyte or analogue thereof; the detection zone being located between a point removed from the ends of the chromatographic medium and the first end of the chromatographic medium, and the control zone being located between a point removed from the ends of the chromatographic medium and the second end of the chromatographic medium;
  (b) an absorber in operable contact with the first end of the chromatographic medium;
  (c) a first substantially fluid-impermeable barrier adjacent to the first surface of the chromatographic medium and having a first application area substantially smaller than the area of the chromatographic medium and located at a point removed from the ends of the chromatographic medium, the first barrier at least partially blocking application of liquid to the chromatographic medium;
  (d) an applicator adjacent to the first barrier, the applicator containing a labeled specific binding partner to the analyte in a form that can be resolubilized by the addition of an aqueous liquid to the applicator, the applicator positioned to apply liquid to the chromatographic medium at the first application area; and
  (e) a second substantially fluid-impermeable barrier adjacent to the applicator and positioned to at least partially block application of liquid to the applicator and to allow application of liquid to the applicator through a second application area substantially smaller than the area of the chromatographic medium and located closer to the second end of the chromatographic medium than to the first end of the chromatographic medium; and
(2) a second opposable component including a sample preparation zone.

In this device, the first and second opposable components are configured so that bringing the first and second opposable components into opposition results in the sample preparation zone being in contact with the second barrier and with the second application area so that the sample in the sample preparation zone is applied to the applicator through the second applicator area and traverses substantially the entire length of the applicator in order to apply the sample and the resolubilized labeled specific binding partner to the chromatographic medium through the first application area.

Another version of an assay device according to the present invention is suitable for performing immunoassays on analytes, such as lipopolysaccharides, that bind directly to the chromatographic medium. Such a device can comprise:

(1) a first opposable component including:
  (a) a chromatographic medium having a first end, a second end, and first and second surfaces, the chromatographic medium having an affinity for the analyte sufficient to immobilize the analyte from an aqueous solution containing the analyte on the chromatographic medium;
  (b) an applicator in operable contact with the first end of the chromatographic medium, the applicator containing a labeled specific binding partner to the analyte in a form that can be resolubilized by the addition of an aqueous liquid to the applicator;
  (c) an absorber in operable contact with the second end of the chromatographic medium; and
  (d) a substantially fluid-impermeable barrier adjacent to the first surface of the chromatographic medium and having an aperture for application of liquid to the chromatographic medium, the barrier at least partially blocking application of liquid to the chromatographic medium; and
(2) a second opposable component including a sample preparation zone.

In this device, the first and second opposable components are configured so that bringing the first and second opposable components into opposition results in the sample preparation zone being in contact with the barrier so that the sample in the sample preparation zone is applied to the chromatographic medium and so that analyte in the test sample is immobilized on the chromatographic medium in at least the vicinity of the aperture.

Still another version of an assay device according to the present invention is particularly useful for performing sequential immunoassays in which the capture step is completed before the labeling step begins. Such a device can comprise:
(1) a first opposable component including:
  (a) a chromatographic medium having a first end, a second end, and first and second surfaces, and having a specific binding partner immobilized thereon in a detection zone;
  (b) a sample preparation zone in operable contact with the first end of the chromatographic medium;
  (c) a first absorber in operable contact with the second end of the chromatographic medium; and
  (d) a substantially fluid-impermeable barrier adjacent to the first surface of the chromatographic medium and having an aperture for application of liquid to the chromatographic medium, the barrier at least partially blocking application of liquid to the chromatographic medium; and
(2) a second opposable component including:
  (a) an applicator containing a labeled specific binding partner to the analyte in a form that can be resolubilized by the addition of an aqueous liquid to the applicator, the applicator positioned such that when the first and second opposable components are brought into opposition, the applicator is in contact with the barrier so that resolubilized labeled specific binding partner is applied through the aperture in the barrier to the chromatographic medium; and
  (b) second and third absorbers positioned such that when the first and second opposable components are brought into opposition, the second absorber and third absorber are in operable contact with portions of the chromatographic medium so that the second and third absorbers remove fluid from the chromatographic medium.

Another version of an assay device according to the present invention is suitable for performing an immunoassay in which a gold label is amplified with silver. Such a device can comprise:
(1) a first opposable component including:
  (a) a chromatographic medium having a first end, a second end, and first and second surfaces, and having a specific binding partner to the analyte immobilized thereon in a detection zone;
  (b) an absorber in operable contact with the second end of the chromatographic medium;
  (c) a conductor in operable contact with the first end of the chromatographic medium;
  (d) a conjugate zone containing a specific binding partner to the analyte labeled with a gold sol in a form that can be resolubilized by the addition of an aqueous liquid to the conjugate zone, the conjugate zone in direct contact with the conductor and in indirect contact with the first end of the chromatographic medium;
  (e) a sample preparation zone for application of a test sample, the sample preparation zone being in direct contact with the conjugate zone, the conductor, conjugate zone, and sample preparation zone being positioned so that the conjugate zone bridges the sample preparation zone and the conductor; and
  (f) a substantially fluid-impermeable barrier adjacent to the first surface of the chromatographic medium and having an aperture for application of liquid to the chromatographic medium, the barrier at least partially blocking application of liquid to the chromatographic medium; and
(2) a second opposable component including:
  (a) an applicator containing, in a form that can be resolubilized by the addition of an aqueous liquid to the applicator: (A) a soluble silver salt and (B) a reducing agent, the applicator positioned so that when the first and second opposable components are brought into opposition, the applicator is in contact with the barrier so that resolubilized silver salt and reducing agent are applied through the aperture in the barrier to the chromatographic medium; and
  (b) second and third absorbers positioned such that when the first and second opposable components are brought into opposition, the second absorber and third absorber are in operable contact with portions of the chromatographic medium so that the second and third absorbers remove fluid from the chromatographic medium.

In a similar device, the second opposable component includes an applicator including two sectors, a first sector for receiving an aqueous liquid, and a second sector containing, in resolubilizable form, a soluble silver salt and a reducing agent. In this device, the applicator is positioned so that when the first and second opposable components are brought into opposition, the first sector of the applicator is in direct contact with the aperture in the barrier and the second sector of the applicator is in indirect contact with the aperture so that the aqueous liquid is applied first to the chromatographic medium to provide a wash, followed by the aqueous silver salt and the reducing agent.

Still another version of an assay device according to the present invention suitable for performing silver-amplified immunoassays incorporates a base panel and an insert. The device can comprise:
(1) a base panel including:
  (a) a first opposable component including:

(i) a chromatographic medium having a first end, a second end, and first and second surfaces, and having a specific binding partner to the analyte immobilized thereon in a detection zone;

(ii) a conjugate zone containing a specific binding partner to the analyte labeled with a gold sol in a form that can be resolubilized by the addition of an aqueous liquid to the conjugate zone, the conjugate zone being in operable contact with the first end of the chromatographic medium;

(iii) a conductor in operable contact with the conjugate zone, the conjugate zone bridging the first end of the chromatographic medium and the conductor; and (iv) a substantially fluid-impermeable barrier adjacent to the first surface of the chromatographic medium and having an aperture for application of liquid to the chromatographic medium, the barrier at least partially blocking application of liquid to the chromatographic medium;

(b) a second opposable component including:

(i) a first receptacle for a swab containing a test sample;

(ii) a well for addition of at least one extraction reagent to the swab; and (iii) a first absorber separated from the receptacle and the well; and (c) a second receptacle for holding an insert stable against relative motion of the surfaces of the insert and of the first and second opposable components; and (2) an insert including:

(a) an applicator containing, in a form that can be resolubilized by the addition of an aqueous liquid to the applicator: (A) a soluble silver salt and (B) a reducing agent;

(b) a second absorber;

(c) a third absorber; and (d) a protrusion for insertion into the second receptacle of the base panel.

The first and second opposable components of the base panel are configured so that, when they are brought into opposition, the first absorber is brought into contact with a portion of the chromatographic medium, and the receptacle is brought into contact with the conductor. The insert is configured such that when the protrusion is inserted into the second receptacle of the base panel, the applicator is in operable contact with the aperture to apply the contents of the applicator to the chromatographic medium through the aperture, and the second and third absorbers are each in operable contact with a portion of the chromatographic medium to withdraw fluid from the chromatographic medium.

A similar device can be used for performing an enzyme-amplified immunoassay. In this device, the applicator of the insert contains, in resolubilizable form, a substrate for an enzyme label that is bound to a specific binding partner to the analyte. The enzyme label produces an insoluble detectable product by catalysis of a reaction involving the substrate.

Other versions of assay devices according to the present invention are suitable for performing competitive immunoassays. In general, a version suitable for performing competitive immunoassays comprises:

(1) a chromatographic medium having a first end, a second end, and first and second surfaces, and having a secondary specific binding partner immobilized thereon in a detection zone, the secondary specific binding partner capable of binding a member of a specific binding pair that lacks affinity for the analyte;

(2) at least one absorber in operable contact with at least one of the first and second ends of the chromatographic medium;

(3) a substantially fluid-impermeable barrier adjacent to the first surface of the chromatographic medium, the barrier having at least one aperture for application of liquid to the chromatographic medium, the barrier at least partially blocking application of liquid to the chromatographic medium; and (4) an affinity membrane adjacent to the barrier, the affinity membrane containing a specific binding partner to the analyte immobilized thereto. The chromatographic medium, absorber, barrier, aperture, and affinity membrane are configured such that liquid applied to the affinity membrane is drawn through the chromatographic medium by the at least one absorber so that a labeled detection reagent binds at the detection zone on the chromatographic medium if analyte is present in the sample.

This device can be elaborated by including a second component, incorporating an applicator containing an analyte analogue in a form that can be resolubilized by the addition of an aqueous liquid to the applicator, the analyte analogue comprising analyte covalently bound to a member of a specific binding pair lacking affinity for the analyte and bindable by the specific binding partner, the analyte analogue being labeled with a detectable label.

BRIEF DESCRIPTION OF THE DRAWINGS

These and other features, aspects, and advantages of the present invention will become better understood with reference to the following description, appended claims, and accompanying drawings where:

FIG. 14A is a drawing of a two-component assay device according to the present invention suitable for performing an assay of an analyte using silver amplification in which a wash is provided before the silver amplification step;

FIG. 14B is a cross-section along line L–L' of the first component of the two-component assay device of FIG. 14A, showing the detail of the chromatographic medium, elements in direct or indirect contact with the chromatographic medium, the barrier, and the aperture;

FIG. 15A is a drawing of an assay device according to the present invention employing a two-component base panel and an insert and suitable for performing a silver-amplified assay for an analyte using a gold label;

FIG. 15B is a cross-section along line M–M' of the first component of the base panel of the assay device of FIG. 15A, showing the detail of the chromatographic medium, elements in direct or indirect contact with the chromatographic medium, the barrier, and the aperture;

DESCRIPTION

Definitions

Figure 1:
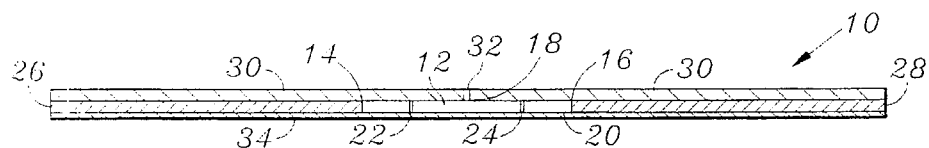
FIG. 1 is a depiction of a side view of a basic single-component assay device according to the present invention.

In the context of this disclosure, the following terms are defined as follows unless otherwise indicated:

Specific Binding Partner: A member of a pair of molecules that interact by means of specific non-covalent interactions that depend on the three-dimensional structures of the molecules involved. Typical pairs of specific binding partners include antigen-antibody, hapten-antibody, hormone-receptor, nucleic acid strand-complementary nucleic acid strand, substrate-enzyme, inhibitor-enzyme, carbohydrate-lectin, biotin-avidin, and virus-cellular receptor.

Operable Contact: Two solid components are in operable contact when they are in contact, either directly or indirectly, in such a manner that an aqueous liquid can flow from one of the two components to the other substantially uninterruptedly, by capillarity or otherwise. "Direct contact" means that the two elements are in physical contact, such as edge-to-edge or front-to-back. Typically, when two components are in direct contact, they are overlapped with an overlap of about 0.5 to about 3 mm. However, the components can be placed with abutting edges. "Indirect contact" means that the two elements are not in physical contact, but are bridged by one or more conductors.

Finite Capacity: An absorber has finite capacity when it becomes saturated by liquid received during the normal performance of an assay in the device in which the absorber is located. At that point, the absorber can release additional liquid absorbed and become at least partially conductive.

Analyte: The term "analyte" includes both the actual molecule to be assayed and analogues and derivatives thereof when such analogues and derivatives bind another molecule used in the assay in a manner substantially equivalent to that of the analyte itself.

Antibody: The term "antibody" includes both intact antibody molecules of the appropriate specificity and antibody fragments (including Fab, F(ab'), and F(ab')$_2$ fragments) as well as chemically modified intact antibody molecules and antibody fragments, including hybrid antibodies assembled by in vitro reassociation of subunits.

Secondary Specific Binding Partner: An additional specific binding partner that binds to a member of a pair of specific binding partners when the pair of specific binding partners is interacting is designated a secondary specific binding partner. For example, a pair of specific binding partners can comprise Giardia antigen and rabbit anti-Giardia antibody. In that case, the secondary specific binding partner can be goat anti-rabbit IgG antibody. The secondary specific binding partner can be specific for the species, class, or subclass of an antibody specific binding partner to which it binds. Alternatively, when one of the specific binding partners is labeled with biotin, the secondary specific binding partner can comprise a molecule conjugated to avidin.

*BARRIER-CONTROLLED ASSAY DEVICES*

One aspect of the present invention is barrier-controlled assay devices useful for immunoassays and other assays depending on specific binding interactions. Two types of assays for which devices according to the present invention are particularly useful are sandwich immunoassays and competitive immunoassays.

A. Principles of the Method

All of the devices according to the present invention have a chromatographic medium adjacent to which is a substantially liquid-impermeable barrier. The barrier at least partially blocks application of liquid to the chromatographic medium. The barrier has an aperture therethrough for application of liquid to the chromatographic medium. Typically, the aperture is substantially smaller than the barrier; preferably, it is in the form of a line or slit.

In some cases, fluid is intended to be applied to the chromatographic medium during the course of the assay procedure through the aperture. This is the situation when both ends of the chromatographic medium are bounded by absorbers. In other cases, liquid can enter the chromatographic medium through one of the ends of the chromatographic medium, as well as through the aperture. In all cases, liquid is intended to flow into the chromatographic medium from the aperture in a direction approximately normal to the plane of the chromatographic medium. This flow in a plane other than the plane of the chromatographic medium is a characteristic of assay devices according to the present invention. These flow characteristics result in more efficient flow and more efficient use of reagents in devices according to the present invention.

Although the basic principle of the invention can be used in a single-component assay device, it is generally preferred to construct assay devices containing two or more opposable components connected by a hinge and fastenable by engagers such as locks. This allows pressure to be placed on the component to drive fluid from one component to another and to accelerate the rate of flow. In other cases, devices comprise two opposable components, with one of the components having a receptacle for positioning of an insert. This arrangement is particularly useful for enzyme immunochromatographic assays and assays involving amplification of a signal, such as gold sol labeling with silver amplification.

B. Elements Common to Devices According to the Present Invention

A number of elements are common to assay devices according to the present invention and are discussed here for convenience.

1. The Chromatographic Medium

The chromatographic medium is a strip. Typically, the strip is substantially planar, although this is not required in all applications. It is typically rectangular, having first and second ends and first and second surfaces. Throughout this description, the term "first end" refers to the end in which liquid is first applied to the chromatographic medium and the term "second end" applies to the opposite end of the chromatographic medium. The liquid applied at or near the first end of the chromatographic medium can be, but is not necessarily, a sample or a treated sample. The chromatographic medium is composed of material suitable as a medium for thin layer chromatography of analyte and analyte-antibody conjugates, such as nitrocellulose, nylon, rayon, cellulose, paper, or silica. The chromatographic medium can be pretreated or modified as needed. Typically, the chromatographic medium is translucent, so that colored zones appearing on it can be viewed from either side.

2. Absorbers

In a number of devices according to the present invention, absorbers are in operable contact with one or both ends of the chromatographic medium. The absorbers can be made of any bibulous material that will hold an aqueous liquid sufficiently so liquid can be drawn through the chromatographic medium and accumulated in the absorber. Typical materials include, but are not limited to, filter paper.

3. Other Fluid-Carrying Elements

As described below, in particular devices according to the present invention, other fluid-carrying elements can be employed as sample preparation zones, applicators, distribution membranes, and/or conductors. These elements are prepared of hydrophilic media that pass aqueous liquids without substantially absorbing them. Such materials are well-known in the art. In some cases, these elements can have incorporated therein a component in dry form that can be resolubilized by addition of an aqueous liquid to the element.

4. Filters

Some devices according to the present invention incorporate at least one filter element to remove particulate elements, such as may be present in fecal matter or other specimens. Alternatively, filters can remove whole cells or bacteria with porosities of 0.22 µm or 0.45 µm. Selection of appropriate filter materials is known to one of ordinary skill in the art; various porous or microporous materials can be used, including cheesecloth, paper, cotton, cellulose, nitrocellulose, or cellulose acetate of appropriate porosities.

5. Opposable Components

Many of the embodiments of the assay device according to the present invention comprise two opposable components. The bodies of the opposable components are preferably made of laminated cardboard that is sufficiently impervious to moisture to contain the liquids involved in the performance of the assay carried out by the device. Other cellulose-based materials, such as paperboard or solid bleached sulfite (SBS) can also be used. Alternatively, the bodies of the opposable components can be made of plastic that is impervious to moisture. A suitable plastic is a polycarbonate plastic such as Lexan™.

The opposable components are joined by a hinge, preferably made a material impermeable to aqueous liquids, such as a plastic that can be compatibly joined with or is the same as the material used for the first and second opposable components.

6. Substantially Fluid-Impermeable Barrier

All devices according to the present invention incorporate at least one substantially fluid-impermeable barrier. The substantially fluid-impermeable barrier can be made of plastic, cardboard, or paper, such as a paper label with adhesive backing. Typically, the substantially fluid-impermeable barrier is thinner than the opposable components. The substantially fluid-impermeable barrier need only be substantially fluid-impermeable for the period of the assay, typically about one to about ten minutes.

7. Labeled Components

For assay devices intended to perform a sandwich immunoassay, the labeled component is typically a labeled specific binding partner to the analyte. The label is preferably a visually detectable label, such as a colloidal metal label. Preferably, the colloidal metal label is gold, silver, bronze, iron, or tin; most preferably, it is gold. The preparation of gold-labeled antibodies and antigens is described in J. DeMey, "The Preparation and Use of Gold Probes," in *Immunocytochemistry: Modern methods and applications*"(J. M. Polak and S. VanNoorden, eds., Wright, Bristol, England, 1986, ch. 8, pp. 115–145, incorporated herein by this reference. Antibodies labeled with colloidal gold are commercially available, such as from Sigma Chemical Company, St. Louis, Mo.

Alternatively, other colloidal labels, such as a colloidal sulfur label or a dye-silica label, can also be used. In a less preferred alternative, the visually detectable label can be a colloidal latex label. It is also possible to use other labels, such as a radioactive label.

One particular embodiment of the present invention uses enzyme-labeled components. These are discussed below.

C. Assay Devices Employing Vertical/Lateral Flow

1. Basic Assay Device Employing Vertical/Lateral Flow

A device according to the present invention employing vertical/lateral flow in a single component comprises:

(1) a chromatographic medium having a first end, a second end, and first and second surfaces, and having a specific binding partner for the analyte immobilized thereto in a detection zone;

(2) at least one absorber in operable contact with at least one of the first and second ends; and (3) a substantially fluid-impermeable barrier adjacent to the first surface of the chromatographic medium, the barrier having at least one aperture therethrough for application of liquid to the chromatographic medium, the barrier at least partially blocking application of liquid to the chromatographic medium.

In this device, the chromatographic medium, absorbers, barrier, and aperture are configured such that liquid applied to the barrier is drawn through the chromatographic medium by the at least one absorber so that an analyte and a detection reagent for the analyte can form a ternary complex at the detection zone on the chromatographic medium.

Typically, the assay device comprises at least two absorbers, one in operable contact with the first end of the chromatographic medium and one in operable contact with the second end of the chromatographic medium. The detection zone is preferably substantially smaller than the area of the chromatographic medium, and the chromatographic medium preferably further includes a control zone of analyte or analogue thereof immobilized thereto in an area substantially smaller than the chromatographic medium and not overlapping with the detection zone. In this arrangement, the control and detection zones are positioned with respect to the aperture and the absorbers such that the detection zone is between the aperture and one of the absorbers and the control zone is between the aperture and the other absorber.

Typically, the assay device further comprises a substantially transparent backing adjacent to the second surface of the chromatographic medium, i.e., the surface that is not adjacent to the barrier and aperture. This is to allow viewing of the chromatographic medium and bands or zones of reagents bound thereto for detection of the analyte. The barrier and other components that are in the line of vision of a user of the device can also be fabricated from transparent materials.

In one preferred arrangement, the aperture is substantially smaller in area than the barrier and the barrier is positioned in relation to the chromatographic medium so that liquid can enter the region of the chromatographic medium adjacent to the barrier only through the aperture.

Typically, the chromatographic medium and the at least one absorber are substantially planar with the barrier being located in a second plane substantially parallel to the plane of the chromatographic medium.

A basic single-component device is depicted in FIG. 1. The device 10 has a planar chromatographic medium 12 having a first end 14, a second end 16, and first and second surfaces 18 and 20. The chromatographic medium 12 has a specific binding partner to the analyte immobilized thereon in a detection zone 22 substantially smaller than the area of the chromatographic medium 12. Preferably, the chromatographic medium 12 further includes a control zone 24 of analyte or analog thereof immobilized thereto in an area substantially smaller than the chromatographic medium 12 and not overlapping the detection zone 22.

The device 10 also has a first absorber 26 in operable contact with the first end 14 of the chromatographic medium 12, and a second absorber 28 in operable contact with the second end 16 of the chromatographic medium 12.

The device 10 also has a substantially fluid-impermeable barrier 30 adjacent to the first surface 18 of the chromatographic medium 12. The barrier 30 has an aperture 32 therethrough for application of liquid to the chromatographic medium 12. The aperture 32 is substantially smaller in area than the barrier 30 so that liquid can enter the region of the chromatographic medium 12 adjacent to the barrier 30 only through the aperture 32.

The chromatographic medium 12 and the absorbers 26 and 28 are preferably substantially in one plane, with the barrier 30 being preferably located in a second plane substantially parallel to the plane defined by the chromatographic medium 10 and the absorbers 26 and 28. The control zone 24 and the detection zone 22 are positioned with respect to the aperture 32 and the absorbers 26 and 28 so that the detection zone 22 is between the aperture 32 and one of the absorbers and the control zone 24 is between the aperture 32 and the other of the two absorbers. In this device, flow in the chromatographic medium 12 is isotropic with respect to fluid applied through the aperture 32 in the barrier 30.

The assay device 10 can further comprise a substantially transparent backing 34 adjacent to the second surface 20 of the chromatographic medium 12.

In operation, the sample to be assayed is mixed with an aqueous solution of a labeled specific binding partner for the analyte to be assayed to form a solution containing the sample and the labeled specific binding partner. The solution containing the sample and labeled specific binding partner is applied to the aperture 32 and is allowed to flow through at least the portion of the chromatographic medium 12 including the detection zone 22, and, if present, the control zone 24. The analyte is then detected and/or determined by observing and/or measuring the labeled specific binding partner in the detection zone 22. The labeled specific binding partner for the analyte binds to the analyte or analogue in the control zone 24, indicating that the test was performed properly. The flow from the aperture 32 to the control zone 22 and the detection zone 34 is in different directions, which is characteristic of assay devices according to the present invention. Thus the same fluid containing the sample and the labeled specific binding partner does not contact both the detection zone 22 and the control zone 24.

A typical sample volume for this is 5 μl–100 μl, more typically 10 μl–40 μl. Typically, flow within the chromatographic medium takes place within about 30 seconds to about five minutes, depending on the dimensions of the chromatographic medium and the material for which it is made, more typically within about one to two minutes. Assays are generally performed at room temperature, but can, if desired, be performed at elevated temperatures of 37° C. to speed up the chromatography and the reaction if the reagents are sufficiently stable. The assay can also be performed at lower temperatures, down to about 4° C. if desirable for enhanced stability of the reagents used.

2. One-Component Assay Device With Applicator Adjacent to Barrier

A further development of an assay device according to the present invention is a one-component assay device with an applicator adjacent to the barrier. The applicator contains a labeled specific binding partner for the analyte in a form that can be resolubilized by addition of an aqueous liquid to the applicator. This eliminates the need to prepare a separate solution of sample and a labeled specific partner and to apply the solution to the device.

This device comprises:

(1) a planar chromatographic medium having a first end, a second end, and top and bottom surfaces and having a specific binding partner to the analyte immobilized thereon in a detection zone as described above;

(2) at least one absorber in operable contact with at least one of the ends of the chromatographic medium;

(3) a substantially fluid-impermeable barrier adjacent to the first surface of the chromatographic medium and having a aperture therethrough for application for liquid to the chromatographic medium as described above; and (4) an applicator adjacent to the barrier, the applicator containing a labeled specific binding partner to the analyte in a form that can be resolubilized by the addition of an aqueous liquid to the applicator.

The applicator is positioned such that the barrier is located between the applicator and the chromatographic medium, and such that a sample applied to the applicator is drawn through the aperture after resolubilizing the specific binding partner and then is drawn through the chromatographic medium by the absorbers so that the analyte and the labeled specific binding partner to the analyte form a ternary complex at the detection zone on the chromatographic medium. This ternary complex is characteristic of a sandwich immunoassay.

As with the device described above, this device preferably comprises a control zone on the chromatographic medium, a second absorber so that there are absorbers at both ends of the chromatographic medium, and a substantially transparent backing adjacent to the second surface of a chromatographic medium, i.e., the surface not adjacent to the barrier.

Figure 2:
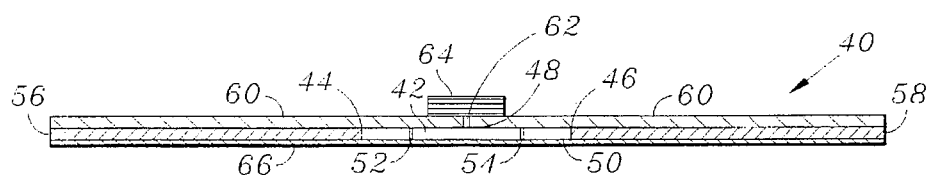
FIG. 2 is a depiction of a side view of a single-component device incorporating an applicator adjacent to the barrier.

This device is depicted in FIG. 2. The device 40 has a planar chromatographic medium 42 having a first end 44 and a second end 46, and first and second surfaces 48 and 50. The chromatographic medium 42 has a specific binding partner to the analyte immobilized in a detection zone 52, and preferably also a control zone 54. The device has a first absorber 56 in operable contact with the first end 44 of the chromatographic medium 42, and a second absorber 58 in operable contact with the second end 46 of the chromatographic medium 42.

The device also has a substantially fluid-impermeable barrier 60 adjacent to the first surface 48 of the chromatographic medium 42. The barrier 60 has an aperture 62 therethrough for application of liquid to the chromatographic medium 42. The aperture 62 is substantially smaller in area than the barrier 60 as described above.

The device 40 also has an applicator 64 adjacent to the barrier 60. The applicator 64 contains a labeled specific binding partner in a form that can be resolubilized by the addition of an aqueous liquid to the applicator 64. The applicator 64 is positioned such that the barrier 60 is between the applicator 64 and the chromatographic medium 42. A sample applied to the applicator 64 is drawn through the aperture 62 after resolubilizing the specific binding partner and then is drawn through the chromatographic medium 42 by the first and second absorbers 56 and 58. This arrangement allows analyte in the sample and labeled specific binding partner to the analyte to form a ternary complex at the detection zone 52 on the chromatographic medium 42. This arrangement further allows the labeled specific binding partner to the analyte can bind the analyte or analyte analogue in the control zone 54 to indicate proper performance of the assay.

The device also has a substantially transparent backing 66 adjacent to the second surface 50 of the chromatographic medium 42.

In use, the sample is applied to the applicator 64 and allowed to resolubilize the labeled specific binding partner in the applicator 64 to form a solution containing a sample and the resolubilized labeled specific binding partner. The solution containing the sample and the resolubilized labeled specific binding partner is then allowed to flow through the aperture 62 and then through at least a portion of the chromatographic medium 42 including the detection zone 52 and, if present, the control zone 54. Detection and/or determination of the analyte is then performed by observing the presence of visible bands at the detection zone 52 and/or the control zone 54.

3. Two-Component Device With Applicator on First Opposable Component

A further development of the device in the present invention is a device with at least two components, with first and second opposable components joined by a hinge.

An embodiment of the device incorporating at least two opposable components comprises:

(1) a first opposable component including:
   (a) a chromatographic medium having a first end, a second end, and first and second surfaces, and having a specific binding partner for the analyte immobilized thereon in a detection zone;
   (b) at least one absorber in operable contact with at least one of the first and second ends of the chromatographic medium; and
   (c) a substantially fluid-impermeable barrier adjacent to the first surface of the chromatographic medium and having an aperture for application of liquid to the chromatographic medium, the barrier at least partially blocking application of liquid to the chromatographic medium; and (2) a second opposable component to apply at least one reactant directly or indirectly to the chromatographic medium through the aperture.

In this device, the first and second opposable components are configured so that bringing the first and second opposable components into opposition results in the second opposable component applying at least one reactant directly or indirectly to the chromatographic medium through the aperture.

Preferably, the first and second opposable components can be held in opposition so that pressure facilitates application of the at least one reactant to the chromatographic medium through the aperture.

In one preferable embodiment of a device according to the present invention using two opposable components, the first opposable component has a chromatographic medium, a barrier, and an applicator containing a labeled specific binding partner to the analyte. The second opposable component has a sample preparation zone to which the sample is applied. This device also has means for opposing the opposable components and applying pressure thereto. The pressure is sufficient to transfer fluid from one opposable component to the other opposable component in a direction substantially normal to the opposable component so that the fluid transferred is applied to the barrier or another element substantially parallel to the barrier. The pressure applied greatly increases the rate and efficiency of fluid transfer and minimizes any dead volume of reagent left behind in fluid-containing elements.

This device comprises:

(1) a first opposable component including a planar chromatographic medium, at least one absorber, a substantially fluid-impermeable barrier having an aperture therethrough, and an applicator adjacent to the barrier; and (2) a second opposable component including a sample preparation zone.

The first and second opposable components are configured so that bringing the first and second opposable components into opposition results in the sample preparation zone being in contact with the applicator so that sample in the sample preparation zone is applied to the applicator for resolubilization of the resolubilizable specific binding partner and chromatography through the chromatographic medium.

This sample preparation zone can contain at least one reagent for treatment of the sample. The reagent or reagents that can be present in the sample preparation zone vary with the sample to be applied to the sample preparation zone and with the analyte to the assay. They can include, but are not limited to, acids or alkalis to adjust the pH, buffers to stabilize the pH, chelating agents such as EDTA or EGTA to chelate metals, hydrolytic enzymes to lyse the cell membrane of animal cells or the cell wall of bacteria, to liberate analytes, substrates or coenzymes for enzymes, and the like. One particularly useful extraction reagent is a mixture of sodium nitrite and acetic acid to generate nitrous acid. The sodium nitrite can be present in dried form on the sample preparation zone, and the acetic acid can be added to the sample preparation zone after the addition of the sample.

Figure 3A:
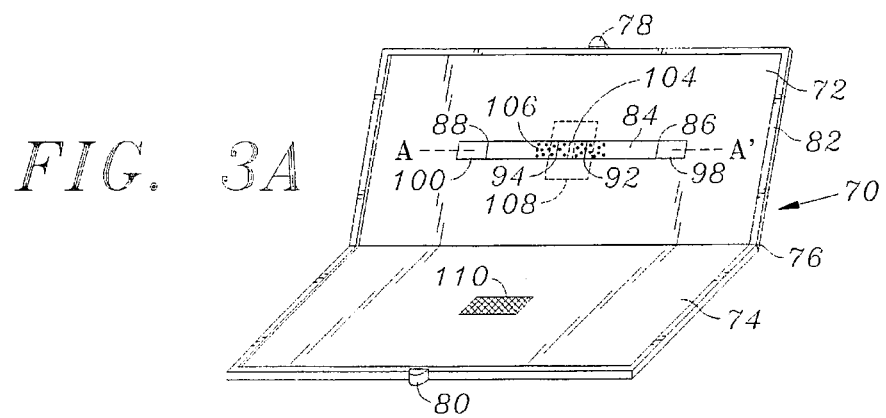
FIG. 3A is a drawing of a two-component assay device according to the present invention with a chromatographic medium, barrier, and applicator on the first component and a sample preparation means on the second component, showing the components separated.
Figure 3B:
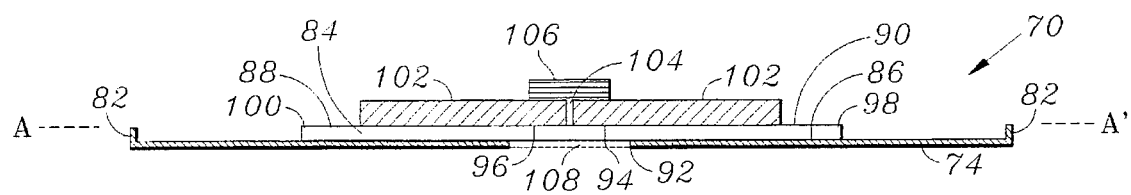
FIG. 3B is a depiction of a side view of the first component of the two-component assay device of FIG. 3A, showing the barrier, aperture, and applicator.

This device is depicted in FIGS. 3A and 3B. The arrangement of the two components is shown in FIG. 3A, and a cross-section of the first component along line A–A', showing the detail of the barrier and the aperture, is shown in FIG. 3B. The device 70 has a first opposable component 72 and a second opposable component 74, joined by a hinge 76. The first and second opposable components 72 and 74 preferably further include engagers that secure the opposable components 72 and 74 in opposition. The engagers can comprise locks, such as locks 78 and 80 that are engaged when the first opposable component 72 and the second opposable component 74 are brought into opposition. To guard against leakage of samples or reagents, a sealing ridge or gasket 82 is positioned around the perimeter of the first and second opposable components 72 and 74.

The first opposable component 72 includes a planar chromatographic medium 84 having a first end 86 and a second end 88, and first and second surfaces 90 and 92. The chromatographic medium 84 includes a detection zone 94, and preferably, a control zone 96. The first opposable component 72 includes a first absorber 98 in operable contact with the first end 86 of the chromatographic medium 84, and a second absorber 100 in operable contact with the second end 88 of the chromatographic medium 84.

The device 70 has a substantially fluid-impermeable barrier 102 adjacent to the chromatographic medium 84. The barrier 102 has an aperture 104 therethrough for application of fluid to the chromatographic medium 84.

The first opposable component 72 also includes an applicator 106 adjacent to the barrier 102. The applicator 104 includes a labeled specific binding partner to the analyte in resolubilizable form. The applicator 106 is positioned so that the barrier 102 is between the applicator 106 and the chromatographic medium 84.

The first opposable component 72 also includes an aperture 108 to allow viewing of the chromatographic medium 84.

The second opposable component 74 includes a sample preparation zone 110, which can contain at least one reagent for treatment of the sample before the sample is applied to the applicator 106. The sample, or, optionally, a sampling device such as a throat swab or a microporous filter, can be placed by the operator on the sample preparation zone 110; if needed, other reagents can be added.

In operation, a sample is applied to the sample preparation zone 110. If desired, the sample can be incubated in the sample preparation zone 110 so that at least one reagent for treatment of the sample can react with the sample to produce a treated sample. The first and second opposable component 72 and 74 are then brought into opposition so that the sample is transferred from the sample preparation zone 110 to the applicator 106. The sample transferred to the applicator 106 is then allowed to resolubilize the labeled specific binding partner in the applicator 106, and chromatography and detection of the analyte is carried out as in the single-component device described above.

4. Two-Component Device With Applicator on Second Opposable Component

Another two-component device according to the present invention is similar to the device depicted in FIG. 3, but has the applicator on the second opposable component. The applicator has labeled specific binding partner for analyte in a resolubilizable form and can also contain one or more reagents for treatment of the sample.

This device comprises:

(1) a first opposable component including a planar chromatographic medium having a first end, a second end, and first and second surfaces and having a specific binding partner to the analyte immobilized thereon as described above, at least one absorber in operable contact with at least one of the ends of the chromatographic medium, and a substantially fluid-impermeable barrier adjacent to the first surface of the chromatographic medium and having an aperture therethrough for application of liquid to the chromatographic medium as described above; and (2) a second opposable component including an applicator for application of a sample thereto, the applicator containing a labeled specific binding partner to the analyte in a form that can be resolubilized by the addition of an aqueous liquid.

Figure 4A:
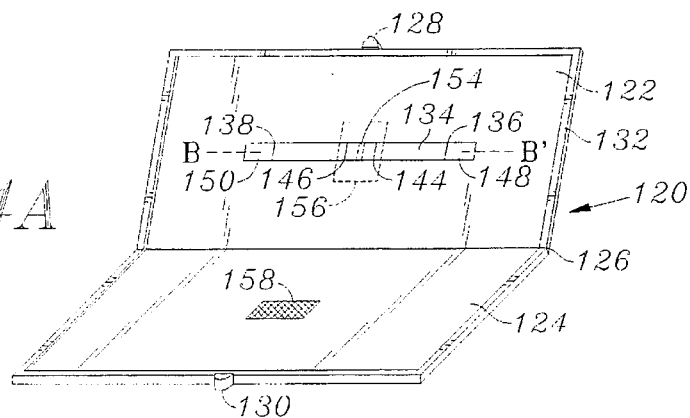
FIG. 4A is a drawing of a two-component assay device according to the present invention with a chromatographic medium, barrier, and aperture on the first component and an applicator on the second component.
Figure 4B:
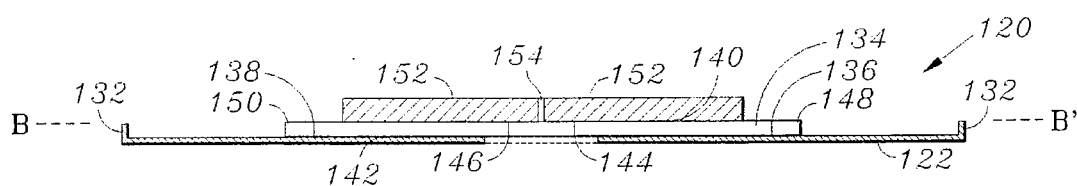
FIG. 4B is a cross-section through line B–B' of the first component of the two-component assay device of FIG. 4A, showing the barrier and aperture.

This device is depicted in FIGS. 4A and 4B. The arrangement of the two components is shown in FIG. 4A, and a cross-section of the first component along line B—B', showing the detail of the barrier and the aperture, is shown in FIG. 4B. The device 120 has a first opposable component 122 and a second opposable component 124, joined by a hinge 126. The first and second opposable components 122 and 124 preferably further include locks 128 and 130 that are engaged when the first and second opposable components 122 and 124 are brought into opposition, and a sealing ridge or gasket 132.

The first opposable component includes a planar chromatographic medium 134 having a first end 136, a second end 138, and first and second surfaces 140 and 142. The chromatographic medium 134 has a specific binding partner to the analyte immobilized in a detection zone 144 substantially smaller than the area of the chromatographic medium 134, and preferably a control zone of analyte or analyte analogue 146.

The first opposable component 122 also has a first absorber 148 in operable contact with the first end 136 of the chromatographic medium 134 and a second absorber 150 in operable contact with the second end 138 of the chromatographic medium 134. The first opposable component 122 also has a substantially fluid-impermeable barrier 152 adjacent to the first surface 140 of the chromatographic medium 134. The barrier 152 has an aperture 154 therethrough for application of liquid to the chromatographic medium 134. The aperture 154 is substantially smaller in area than the barrier 152 so that liquid can enter the region of the chromatographic medium 134 adjacent to the barrier 152 only through the aperture 154. The chromatographic medium and the absorbers 148 and 150 are substantially planar, with the barrier 152 being located in a second plane substantially parallel to the plane defined by the chromatographic medium 134 and the absorbers 148 and 150. The control zone 146 and the detection zone 144 are positioned with respect to the aperture 154 and the absorbers 148 and 150 so that the detection zone 144 is between the aperture 154 and one of the absorbers and the control zone 146 is between the aperture 154 and the other of the absorbers. The first opposable component 122 also includes a window 156 for viewing of at least a portion of the chromatographic medium 134.

The second opposable component 124 has an applicator 158 to which sample is applied and which contains a resolubilizable labeled specific binding partner to the analyte. The applicator 156 can also contain at least one reagent for treatment of the sample in dry form.

In use, the sample is applied to the applicator 156 to resolubilize the labeled specific binding partner for the analyte. If desired, the sample can be incubated in the applicator 156 to ensure that any reagent for treatment of the sample reacts with the sample. The first and second opposable components 132 and 134 are then brought in to opposition so that the sample and the resolubilized labeled specific binding partner can be applied to the chromatographic medium 134 through the aperture 154. Chromatography and detection of the analyte are carried out as described above by observing labeled specific binding partner bound to the detection zone 144 on the chromatographic medium 134.

5. Devices With Filter to Remove Particulates a. Device With Filter in Fluid Path After Introduction of Resolubilized Labeled Specific Binding Partner Several versions of devices according to the present invention incorporate a filter to remove particulates, such as fecal matter, from a sample such as a fecal sample used to detect fecal occult blood as an indicator of gastrointestinal disease. One such device places the filter in the fluid path after introduction of the resolubilized specific binding partner. This device has an applicator on the second opposable component containing labeled specific binding partner in resolubilizable form.

This version of a filter-containing device comprises: (1) a first opposable component including a planar chromatographic medium having a first end, a second end, and first and second surfaces and having a specific binding partner to the analyte immobilized thereon, at least one absorber in operable contact with one of the ends of the chromatographic medium, a substantially fluid-impermeable barrier adjacent to the first surface of the chromatographic medium and having an aperture therethrough for application of liquid to the chromatographic medium, and a filter for removing particulates adjacent to the barrier; and (2) a second opposable component including an applicator for application of a sample thereto.

In this device, the chromatographic medium, the barrier, and the filter are positioned so that the barrier is located between the filter and the chromatographic medium. The first and second opposable components are configured so that bringing the first and second opposable components into opposition results in the applicator being in contact with the filter so that the sample and the resolubilized labeled specific binding partner in the applicator are applied to the filter and then through the aperture to the barrier to the chromatographic medium for chromatography.

Figure 5A:
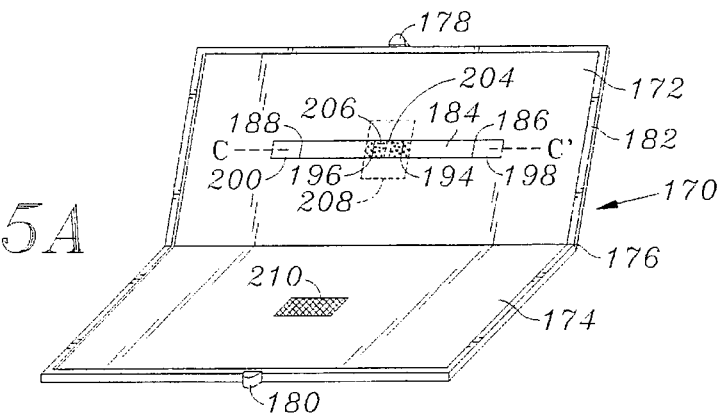
FIG. 5A is a drawing of a two-component assay device according to the present invention with a chromatographic medium, barrier, aperture, and filter membrane on the first component and an applicator on the second component.
Figure 5B:
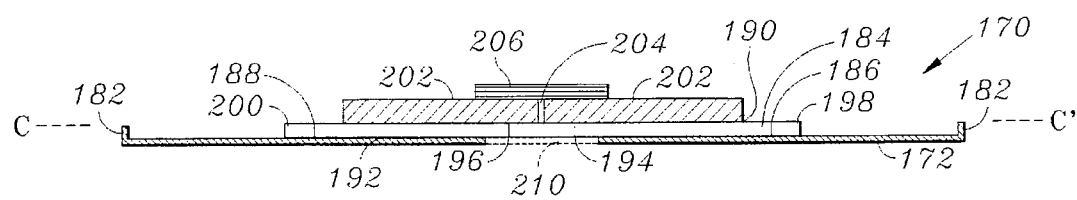
FIG. 5B is a cross-section through line C–C' of the first component of the two-component assay device of FIG. 5A, showing the barrier, aperture, and filter membrane.

This device is depicted in FIGS. 5A and 5B. The arrangement of the two components is shown in FIG. 5A, and a cross-section of the first component along line C–C' showing the detail of the barrier, the aperture, and the filter membrane, is shown in FIG. 5B. The device 170 includes a first opposable component 172 and a second opposable component 174, joined by hinge 176. The first and second opposable components 172 and 174 preferably further include locks 178 and 180 that are engaged when the first and second opposable components 172 and 174 are brought into opposition, and a sealing ridge or gasket 182.

The first opposable component 172 includes a planar chromatographic medium 184 having a first end 186, a second end 188, and first and second surfaces 190 and 192. The chromatographic medium 184 has a specific binding partner to the analyte immobilized in a detection zone 194 substantially smaller than the area of the chromatographic medium 184 and, preferably, a control zone 196 containing analyte or analogue thereof immobilized on the chromatographic medium 184. The first opposable component 172 also includes a first absorber 198 in operable contact with the first end 186 of the chromatographic medium 184, and a second absorber 200 in operable contact with the second end 188 of the chromatographic medium 184.

The first opposable component 172 also includes a substantially fluid-impermeable barrier 202 adjacent to the first surface 190 of the chromatographic medium 184. The barrier 202 has an aperture 204 therethrough for application of liquid to the chromatographic medium 184. The aperture 204 is substantially smaller in area than the barrier 202 so that liquid can enter the region of the chromatographic medium 184 adjacent to the barrier 202 only through the aperture 204.

The first opposable component 172 further includes a filter 206 adjacent to the barrier 202 for removing particulates.

The first opposable component 172 further includes a window 208 for viewing of at least a portion of the chromatographic medium 184.

The second opposable component 174 includes an applicator 210 containing a labeled specific binding partner in resolubilizable form. The applicator 210 can also contain at least one reagent for treatment of the sample.

In operation, bringing the first and second opposable components 172 and 174 into opposition results in the applicator 210 being in contact with the filter 206 so that the sample and the resolubilized labeled specific binding partner in the applicator 210 are applied to the filter 206, and then, after passage through the filter 206, through the aperture 204 and onto the chromatographic medium 184 for chromatography and detection of the analyte as described above.

Device With Filter in Fluid Path Before Introduction of Resolubilized Labeled Specific Binding Partner This version may be particularly useful if particulates interfere with resolubilization of the labeled specific binding partner or with reaction of the labeled specific binding partner with the analyte.

This version comprises:

(1) a first opposable component including:
(a) a planar chromatographic medium having a first end, a second end, and first and second surfaces, and having a specific binding partner to the analyte immobilized thereon as described above;
(b) at least one absorber in operable contact with at least one of the ends of the chromatographic medium;
(c) a substantially fluid-impermeable barrier adjacent to the first surface of the chromatographic medium and having an aperture therethrough for application of liquid to the chromatographic medium as described above;
(d) an applicator adjacent to the barrier containing a labeled specific binding partner to the analyte in resolubilizable form; and
(e) a filter for removing particulates adjacent to the applicator; and (2) a second opposable component including a sample preparation zone.

The barrier, the applicator, and the filter are positioned so that the applicator is located between the barrier and the filter, with the barrier being located closest to the chromatographic medium. The first and second opposable components are configured so that bringing the first and second opposable components into opposition results in the sample preparation zone being in contact with the filter so that sample is applied to the filter, the filtered sample is applied to the applicator to resolubilize the labeled specific binding partner and the applicator to form a solution of filtered sample and labeled specific binding partner, and the solution of filtered sample and labeled specific binding partner is applied to the chromatographic medium through the aperture in the barrier.

Figure 6A:
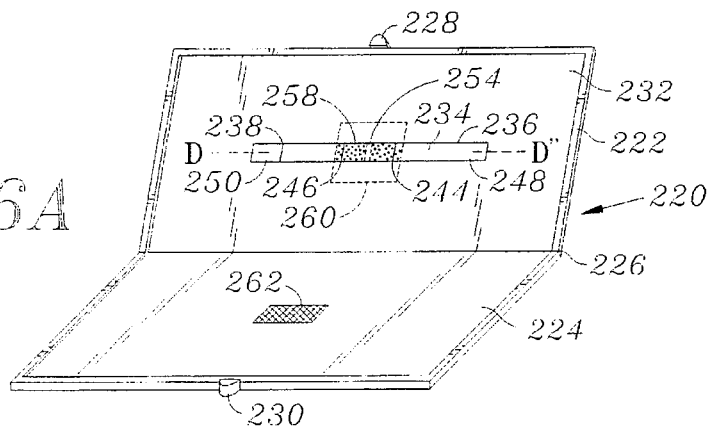
FIG. 6A is a drawing of another two-component assay device according to the present invention with a chromatographic medium, barrier, aperture, applicator, and filter membrane on the first component and a sample preparation zone on the second component.
Figure 6B:
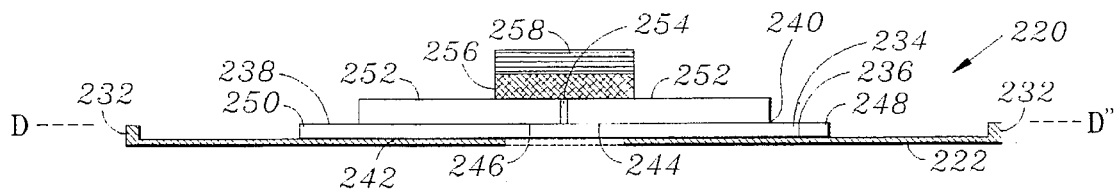
FIG. 6B is a cross-section through line D–D' of the first component of the two-component assay device of FIG. 6A, showing the barrier, the aperture, the applicator and the filter membrane.

This version is depicted in FIG. 6A and 6B. The arrangement of the two components is shown in FIG. 6A, and a cross-section of the first component along line D–D', showing the detail of the barrier, the aperture, the applicator and the filter membrane is shown in FIG. 6B. The device 220 has a first opposable component 222 and a second opposable component 224, joined by a hinge 226. The first and second opposable components 222 and 224 preferably further include locks 228 and 230 which can be engaged when the first opposable component 222 and the second opposable component 224 are brought into opposition. A sealing ridge or gasket 232 is positioned around the perimeter of the first and second opposable components 222 and 224. The first opposable component 222 has a chromatographic medium 234, with first and second ends 236 and 238, a first surface 240, and a second surface 242. The chromatographic medium 234 has a detection zone 244, and, preferably a control zone 246, not overlapping the detection zone 244. The first opposable component also includes a first absorber 248 in operable contact with the first end 236 of the chromatographic medium 234, and a second absorber 250 in operable contact with the second end 238 of the chromatographic medium 234.

The first opposable component 222 also includes a fluid-impermeable barrier 252 adjacent to the first surface 240 of the chromatographic medium 234, with an aperture 254 therethrough for application of liquid to the chromatographic medium 234. The aperture 254 is substantially smaller in area than the barrier 252 so that liquid can enter the chromatographic medium 234 only through the aperture 254.

The first opposable component 222 further includes an applicator 256 adjacent to the barrier 252. The applicator contains a labeled specific binding partner to the analyte in resolubilizable form. The first opposable component also includes a filter 258 for removing particulates adjacent to the applicator 256. The filter 258, the applicator 256, and the barrier and aperture 252 and 254 are arranged so that liquid transferred to the first opposable component 222 first is applied to the filter 258, then to the applicator 256, and finally to the aperture 254 in the barrier 252 for transfer to the chromatographic medium 234.

Preferably, the first opposable component 222 further includes a window 260 adjacent to the second surface 242 of the chromatographic medium 234.

The second opposable component 224 includes a sample preparation zone 262 that can contain at least one reagent for treatment of the sample.

In operation, the sample is transferred to the second opposable component 224 with incubation, if desired, and the first and second opposable components 222 and 224 are then brought in to opposition. Chromatography and detection of the analyte at the detection zone 244 of the chromatographic medium 234 are carried out essentially as described above.

6. Device for Extraction of a Swab

Another version of an assay device according to the present invention is adapted for extraction of a swab. In many cases, biological samples are obtained on swabs, and it is difficult to extract the sample from the swab without performing multiple extractions in extraction vessels. The performance of such multiple extractions not only requires substantial expenditures of labor and time, but leads to the generation of large quantities of waste that must be disposed. This has become an increasingly serious problem since the rise of diseases spread by secretions such as AIDS and hepatitis.

A device according to the present invention suitable for the extraction of a swab and the assay of an analyte contained in the swab can comprise:

(1) a first opposable component including:
  (a) a planar chromatographic medium having a first end, a second end, and first and second surfaces, and having a specific binding partner to the analyte immobilized thereon as described above;
  (b) at least one absorber in operable contact with one of the ends of the chromatographic medium;
  (c) a first substantially fluid-impermeable barrier adjacent to the first surface of the chromatographic medium and having an aperture therethrough for application of liquid to the chromatographic medium as described above;
  (d) an applicator adjacent to the first barrier, the applicator containing a labeled specific binding partner to the analyte in a form that can be resolubilized by the addition of an aqueous liquid to the applicator;
  (e) a second substantially fluid-impermeable barrier adjacent to a central portion of the applicator; and
  (f) a distribution membrane adjacent to the second barrier and in operable contact with the portion of the applicator to which the second barrier is not adjacent so that fluid can flow from the distribution membrane to the applicator only around the second barrier; and (2) a second opposable component including a receptacle for a swab containing a test sample.

The first and second opposable components are configured so that bringing the first and second opposable components into opposition results in a swab inserted in the receptacle being in contact with the distribution membrane so that the sample in the swab is applied to the distribution membrane and then to the chromatographic medium through the aperture in the first barrier after passing around the second barrier and through the applicator.

Figure 7A:
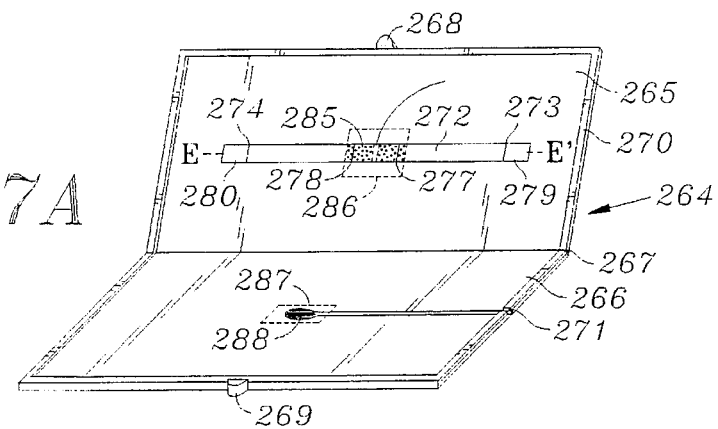
FIG. 7A is a drawing of another two-component assay device according to the present invention suitable for use with a sample on a swab, with a chromatographic medium, a first barrier, an aperture, an applicator, a second barrier, and a distribution membrane on the first component and a receptacle for a swab on the second component.
Figure 7B:
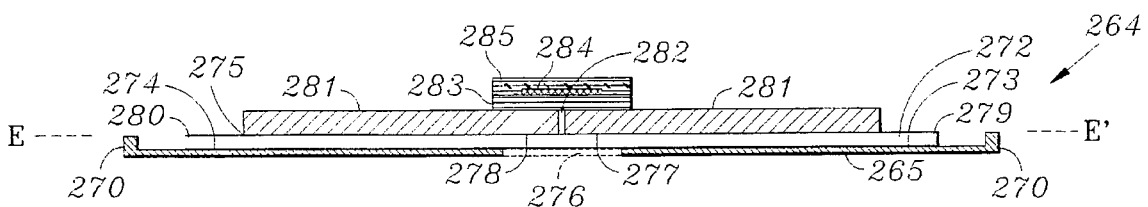
FIG. 7B is a cross-section through line E–E' of the first component of the two-component assay device of FIG. 7A, showing the first barrier, the aperture, the applicator, the second barrier, and the distribution membrane.

A device suitable for extraction of a swab is depicted in FIGS. 7A and 7B. FIG. 7A shows the arrangement of the two components, and a cross section along line E–E' of the first component, showing the detail of the first barrier, the aperture, the applicator, the second barrier, and the distribution membrane, is shown in FIG. 7B. The device 264 comprises a first opposable component 265 and a second opposable component 266 joined by a hinge 267. The first and second opposable components 265 and 266 preferably include locks 268 and 269 to hold the opposable components together. A gasket 270 surrounds the first and second opposable components 265 and 266 when they are in opposition to prevent leakage of the sample or reagents. The gasket 270 can have an opening 271 to accommodate the narrow end of the swab, e.g., a wooden stick or dowel.

The first opposable component 265 has a chromatographic medium 272, with a first end 273 and a second end 274, and a first surface 275 and a second surface 276. The chromatographic medium 272 incorporates a detection zone 277 and a control zone 278, as described above. The first opposable component 265 also has a first absorber 279 in operable contact with the first end 273 of the chromatographic medium 272, and a second absorber 280 in operable contact with the second end 274 of the chromatographic medium 272.

The first opposable component 265 also includes a first substantially fluid-impermeable barrier 281 adjacent to the first surface 275 of the chromatographic medium 272 and having an aperture 282 therethrough for application of liquid to the chromatographic medium 272, as described above.

The first opposable component 265 also includes an applicator 283 adjacent to the first barrier 281. The applicator 283 contains a labeled specific binding partner to the analyte in resolubilizable form. Additionally, the first opposable component 265 has a second substantially fluid-impermeable barrier 284 adjacent to the central portion of the applicator 283. A distribution membrane 285 is adjacent to the second barrier 284 and in operable contact with the portion of the applicator 283 to which the second barrier 284 is not adjacent. Fluid can flow from the distribution membrane 285 to the applicator 283 only around the second barrier 284. Alternatively, the distribution membrane 285 can be omitted so that fluid is applied directly to the second barrier 284 and flows around the second barrier 284 to the applicator 283.

The first opposable component 265 also includes a window 286 to allow viewing of the chromatographic medium 272.

The second opposable component 266 includes a receptacle 287 for a swab 288 containing a test sample. Bringing the first and second opposable components 265 and 266 into opposition results in the swab 288 in the receptacle 286 being in contact with the distribution membrane 285. The sample in the swab 288 is applied to the distribution membrane 285 and then to the chromatographic medium 272 through the aperture 282 in the first barrier 281 after passing around the second barrier 284 and through the applicator 283. In use, the swab 288 is inserted into the receptacle 286 in the second opposable component 266. An extraction reagent or reagents can be added to the swab 288 in the receptacle 286 if desired. In this case the receptacle 286 is designed to accommodate the extraction reagents and to apply them to the swab 288. The first and second opposable components 265 and 266 are then brought into opposition, so the sample in the swab 288 is applied to the distribution membrane 285 as described above.

Another device according to the present invention suitable for the extraction of a swab and the assay of an analyte contained in the swab can comprise:

(1) a first opposable component including:
  (a) a chromatographic medium having a first end, a second end, and first and second surfaces, and having a specific binding partner to the analyte immobilized thereon as described above;
  (b) at least one absorber in operable contact with one of the ends of the chromatographic medium;
  (c) a first substantially fluid-impermeable barrier adjacent to the first surface of the chromatographic medium and having a first aperture therethrough for application of liquid to the chromatographic medium as described above;
  (d) a distribution membrane adjacent to the first substantially fluid-impermeable barrier to direct fluid to the first aperture in the first substantially fluid-impermeable barrier;
  (e) a second substantially fluid-impermeable barrier adjacent to a central portion of the distribution membrane;
  (f) an applicator containing a labeled specific binding partner to the analyte in resolubilizable form and positioned adjacent to the barrier membrane so that fluid can flow from the applicator around the second barrier to the portion of the distribution membrane to which the second substantially fluid-impermeable barrier is not directly adjacent; and (g) a surface barrier containing a second aperture therethrough for application of liquid to the applicator; and (2) a second opposable component including a receptacle for a swab containing a test sample.

The first and second opposable components are configured so that bringing the first and second opposable components into opposition results in a swab inserted in the receptacle being in contact with the surface barrier and the second aperture so that the sample in the swab is applied to the applicator and then to the chromatographic medium through the aperture in the first barrier after passing around the second barrier and through the distribution membrane.

Figure 8A:
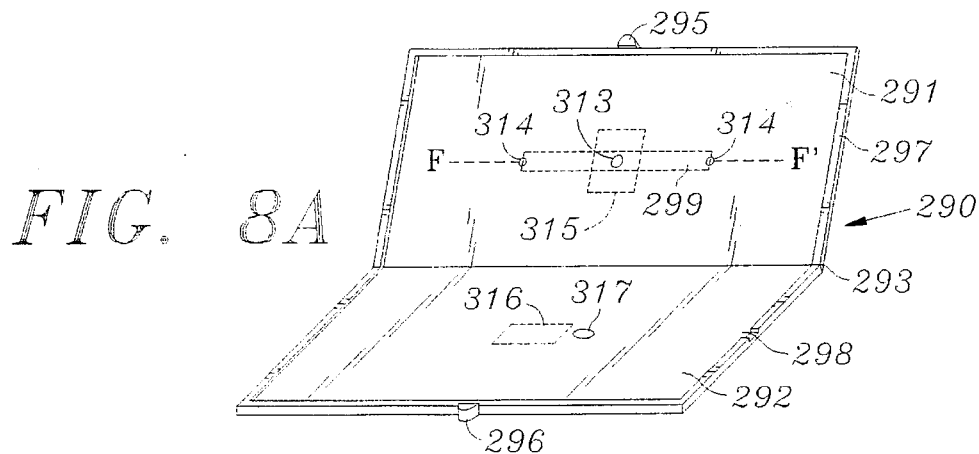
FIG. 8A is a drawing of a two-component assay device according to the present invention suitable for performing a sandwich immunoassay using a sample on a swab, with an applicator containing a resolubilizable labeled specific binding partner for the analyte adjacent to a barrier membrane.
Figure 8B:
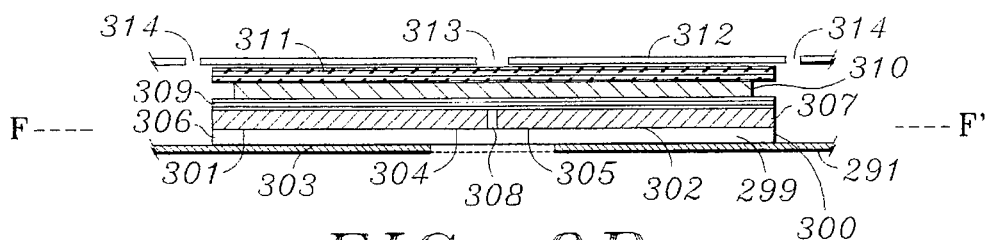
FIG. 8B is a cross-section through the first component and chromatographic medium of the two-component assay device of FIG. 8A along line F–F', showing the chromatographic medium, the first barrier and aperture, the distribution membrane, the second barrier, the applicator, and the surface barrier and aperture.

This device is shown in FIGS. 8A and 8B. FIG. 8A shows the arrangement of the two components, and a cross section along line F–F' of the first component, showing the detail of the first barrier, the aperture, the applicator, the second barrier, and the distribution membrane, is shown in FIG. 8B. The device 290 comprises a first opposable component 291 and a second opposable component 292 joined by a hinge 293. The first and second opposable components 291 and 292 preferably include locks 295 and 296 to hold the opposable components together. A gasket 297 surrounds the first and second opposable components 291 and 292 when they are in opposition to prevent leakage of the sample or reagents. The gasket 297 can have an opening 298 to accommodate the narrow end of the swab, e.g., a wooden stick or dowel.

The first opposable component 291 has a chromatographic medium 299, with a first end 300, a second end 301, a first surface 302, and a second surface 303. The chromatographic medium 299 incorporates a detection zone 304 and a control zone 305, as described above. The first opposable component 291 also has an absorber 306 in operable contact with the second end 300 of the chromatographic medium 299.

The first opposable component 291 also includes a first substantially fluid-impermeable barrier 307 adjacent to the first surface 302 of the chromatographic medium 299 and having a first aperture 308 therethrough for application of liquid to the chromatographic medium 299, as described above.

The first opposable component 291 also includes a distribution membrane 309 adjacent to the first substantially fluid-impermeable barrier 307 to direct fluid to the first aperture 308 in the first barrier 307. Adjacent to a central portion of the distribution membrane 309 is a second substantially fluid-impermeable barrier 310. The first opposable component 291 also includes an applicator 311 containing a labeled specific binding partner to the analyte in resolubilizable form and positioned adjacent to the second barrier 310. Fluid can flow from the applicator 311 around the second barrier 310 to the portion of the distribution membrane 309 to which the second substantially fluid-impermeable barrier 310 is not directly adjacent. Additionally, the first opposable component 291 has a surface barrier 312 containing a second aperture 313 therethrough for application of liquid to the applicator 311. Preferably, the surface barrier 312 is situated substantially level with the surface of the first opposable component 291; i.e., the components below the surface barrier 312 are located inside the first opposable component 291. The first opposable component 291 can also include one or more vents 314 for relieving pressure.

The first opposable component 291 also includes a window 315 to allow viewing of the chromatographic medium 299.

The second opposable component 292 includes a receptacle 316 for a swab containing a test sample, and, preferably, a well 317 for the addition of one or more reagents to the swab.

Bringing the first and second opposable components 291 and 292 into opposition results in the swab in the receptacle 316 being in contact with the surface barrier 312 and second aperture 313. The sample in the swab is applied to the applicator 311 and then to the chromatographic medium 299 after passing around the second barrier 310 and through the distribution membrane 309. In use, the swab 288 is inserted into the receptacle 316 in the second opposable component 292 and an extraction reagent or reagents can be added to the well 317 if desired. The first and second opposable components 291 and 292 are then brought into opposition to perform the assay, and the results are read.

7. Devices for Competitive Immunoassays

Devices according to the present invention can be used for competitive immunoassays as well as for sandwich immunoassays.

Typically, competitive assays are used for monovalent analytes. The monovalent analytes are typically haptens, but the same principles can be used to assay any analyte that is monovalent, such as a normally multivalent antigen on which the additional antibody-binding sites are blocked or modified. Assayable analytes include the following: theophylline, digoxin, disopyramide, lidocaine, procainamide, propranolol, quinidine, amikacin, penicillin and other β-lactam antibiotics, chloramphenicol, gentamycin, kanamycin, netilmycin, tobramycin, tricyclic antidepressants, ethosuximide, phenobarbital, diazepam, phenytoin, primidone, valproic acid, acetaminophen, acetylsalicylic acid, ibuprofen, methotrexate, drugs of abuse such as morphine, codeine, cocaine, fentanyl, 3-methylfentanyl, amphetamines, lysergic acid diethylamide, phencyclidine, and heroin and their metabolites, DNP, 1-substituted-4-hydroxy-2-nitrobenzenes, 4-substituted 2-nitrotrialkylanilinum salts, and environmental contaminants such as benzene, toluene, xylene, ethylbenzene, chlordane, DDT and its metabolites, 2,4-D, 2,4,5-T, and atrazine.

Specific binding partners suitable for the performance of these assays includes, but are not limited to, antibodies and specific binding proteins. An example of the latter is the penicillin binding protein (PBP) isolated from *Bacillus stearothermophilus*.

Unlike many previous assay devices adapted for carrying out competitive immunoassays, devices according to the present invention have the advantage that the presence of analyte in the sample gives a positive or detectable result, such as a colored line in the detection zone of the device. Typically, in competitive immunoassays, the development of a detectable signal indicates a negative result (no analyte present). Thus, an inverse relationship exists between the observed result and detection. The devices of the present invention, which yield a direct relationship between the analyte concentration and the detectable signal are less likely to yield false negative results. These devices also possess an expanded dynamic range.

In a competitive immunoassay device according to this invention, the labeled component is an analyte analog, not an anti-analyte antibody, as is typical for devices carrying out sandwich immunoassays. The analyte analogue comprises analyte covalently bound to a member of a specific binding pair. The member of the specific binding pair lacks affinity for the analyte and is bindable by a secondary specific binding partner immobilized to the chromatographic medium in the detection zone. The competitive aspect of this system comes from the use of an affinity membrane that has immobilized thereto a specific binding partner for the analyte. Thus, analyte in the test sample, if any, competes with the labeled analyte analogue for binding to the affinity membrane, so that in the absence of analyte, all or substantially all of the labeled analyte analogue is bound by the specific binding partner on the affinity membrane and none reaches the chromatography medium. If analyte is present in the test sample, at least some of the labeled analyte analogue cannot bind to the specific binding partner on the affinity medium because of the competition between the unlabeled analyte in the test sample and the analyte analogue. Therefore, at least some of the labeled analyte analogue reaches the chromatography medium and is bound by the secondary specific binding partner in the detection zone. The greater the concentration of analyte in the test sample, the greater the quantity of labeled analyte analogue that reaches the chromatographic medium.

A suitable device for such competitive immunoassays comprises:

(1) a first opposable component including:
   (a) a planar chromatographic medium having a first end, a second end, and first and second surfaces, and having a secondary specific binding partner immobilized thereon in a detection zone substantially smaller than the area of the chromatographic medium, the secondary specific binding partner capable of binding a member of a specific binding pair that lacks affinity for the analyte;
   (b) at least one absorber in operable contact with one of the ends of the chromatographic medium;
   (c) a substantially fluid-impermeable barrier adjacent to the top surface of the chromatographic medium and having an aperture therethrough for application of liquid to the chromatographic medium, the aperture being substantially smaller in area than the barrier so that liquid can enter the chromatographic medium only through the aperture; and
   (d) an affinity membrane adjacent to the barrier, the affinity membrane containing a specific binding partner to the analyte immobilized thereto; and (2) a second opposable component including an applicator, the applicator containing an analyte analogue in a form that can be resolubilized by the addition of an aqueous liquid to the applicator, the analyte analogue comprising analyte covalently bound to a member of a specific binding pair lacking affinity for the analyte and bindable by the specific binding partner, the analyte analogue being labeled with a detectable label.

The chromatographic medium, absorbers, barrier and aperture are configured so that the detection zone is located between the aperture and the first end of the chromatographic medium. The first and second opposable components are configured so that bringing the first and second opposable components into opposition results in the applicator being in contact with the affinity membrane so as to apply the sample and the resolubilized analyte-analog to the affinity membrane and then to the chromatographic medium through the aperture.

The chromatographic medium can further include a control zone of a member of a specific binding pair lacking affinity for the analyte or for the specific binding partner, with the applicator further including a compound binding the member of the specific binding pair in the control zone labeled with a second detectable label distinguishable from the label with which the analyte analogue is labeled. The control zone is located between the aperture and the second end of the chromatographic medium. If a control zone is included, both first and second absorbers are preferably used so that sufficient sample is applied to the control zone.

Figure 9A:
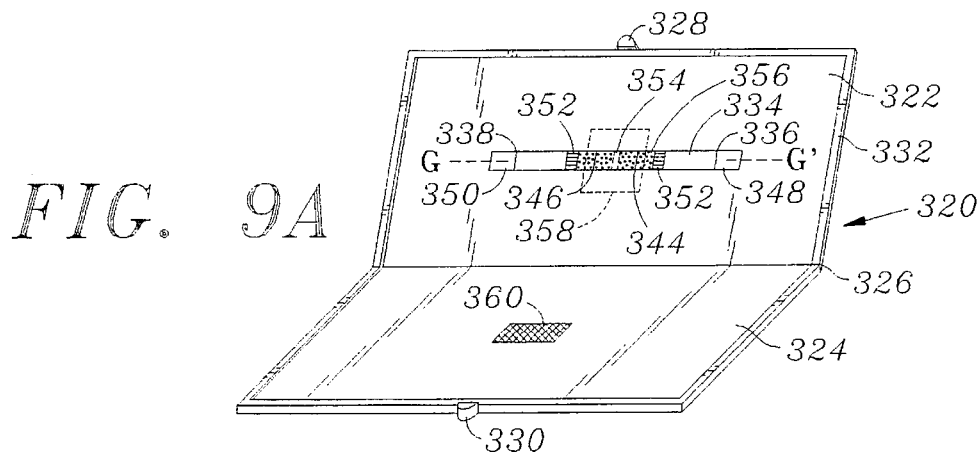
FIG. 9A is a drawing of a two-component assay device according to the present invention suitable for performing a competitive immunoassay, incorporating a chromatographic medium, a barrier, an aperture, and an affinity membrane.
Figure 9B:
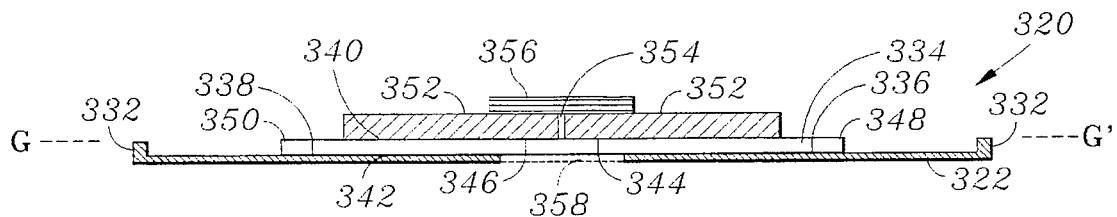
FIG. 9B is a cross-section along line G–G' of the first component of the two-component assay device of FIG. 9A, showing the detail of the chromatographic medium, the barrier, the aperture, and the affinity membrane.

A suitable two-component device for the performance of competitive immunoassay using a labeled analyte analogue is depicted in FIGS. 9A and 9B. The arrangement of the two components is shown in FIG. 9A, and a cross-section along line G–G' of the first component, showing the detail of the chromatographic medium, the barrier, the aperture, and the affinity membrane, is shown in FIG. 9B. The device 320 comprises first and second opposable components 322 and 324 joined by a hinge 326. The first and second opposable components 322 and 324 have locks 328 and 330 for engagement, and a gasket or ridge 332 surrounds the perimeter of the first and second opposable components 322 and 324 to prevent the leakage of sample or reagents. The first opposable component 322 also includes a chromatographic medium 334 having first and second ends 336 and 338 and first and second surfaces 340 and 342. The chromatographic medium 334 includes a detection zone 344 and, preferably, a control zone 346. The first opposable component also includes a first absorber 348 in operable contact with the first end 336 of the chromatographic medium and located closer to the detection zone 344 than to the control zone 346, as well as a second absorber 350 in operable contact with the second end 338 of the chromatographic medium 334 and closer to the control zone 346 than the detection zone 344.

The first opposable component 322 also includes a substantially fluid-impermeable barrier 352 adjacent to the first surface 340 of the chromatographic medium 334 and having an aperture 354 therethrough for application of liquid to the chromatographic medium 334 as described above. The detection zone is located between the aperture 354 and the first end 336 of the chromatographic medium 334. The control zone 346, if present, is located between aperture 354 and the second end 338 of the chromatographic medium 334.

The first opposable component 322 also includes an affinity membrane 356 adjacent to the barrier 352. The affinity membrane 356 contains a specific binding partner to the analyte immobilized thereto so that labeled analyte analogue and free analyte in the test sample can compete with the specific binding partner in the affinity membrane 356.

The first opposable component also includes a window 358 for viewing of the chromatographic medium 334.

The second opposable component 324 includes an applicator 360 that contains a labeled analyte analogue in resolubilizable form. If a control zone 346 is present on the chromatographic medium 334, the applicator 360 also includes a second bindable component labeled with a second, distinguishable label.

In use, the sample is applied to the applicator 360 to resolubilize the labeled analyte analogue, and if present, the second bindable component. The first and second opposable component 322 and 324 are then brought into opposition, applying the sample and the resolubilized labeled analyte analogue to the affinity membrane 356. If no analyte is present in the test sample, all of the analyte analogue is bound to the affinity membrane 356 and none reaches the detection zone 344 on the chromatographic medium 334. If analyte is present in the test sample, it competes with the labeled analyte analogue for the specific binding partner on the affinity membrane 356, so some of the labeled analyte analogue reaches the detection zone 344 on the chromatographic medium 334 and is bound there, giving a detectable signal. If the control zone 346 is present on the chromatographic medium, and a second bindable substance is applied to the applicator, the second bindable substance, with its distinguishable label, binds to the control zone 346 to indicate that the assay has been performed correctly.

D. Non-Isotropic Flow Devices

All devices previously described have used isotropic split flow in each element; that is, liquid was applied to the center of the element and flowed outwardly equally or substantially equally in both directions. However, this is not required, and it is possible to construct assay devices according to the present invention in which flow in one or more of the elements is not from the center of the element equally in both directions, or, alternatively, from both ends of the element towards the center, but is from one end of the element to the other. This may allow particularly efficient use of reagents, particularly resolubilizable reagents where it is desirable to have the liquid flow through the entire element to promote complete resolubilization.

One device according to the present invention using such non-isotropic flow is suitable for performing a sandwich immunoassay. This device comprises:

(1) a first opposable component including:
  (a) a chromatographic medium having a first end, a second end, and first and second surfaces, and having immobilized thereon in separate discrete and non-overlapping zones, the area of each zone being substantially smaller than the area of the chromatographic medium:
    (i) a detection zone of a specific binding partner to the analyte; and
    (ii) a control zone of analyte or analog thereof, the detection zone being located between a point removed from the ends of the chromatographic medium and the first end of the chromatographic medium, and the control zone being located between the point removed from the ends of the chromatographic medium and the second end of the chromatographic medium;
  (b) an absorber in operable contact with the first end of the chromatographic medium;
  (c) a first substantially fluid-impermeable barrier adjacent to the first surface of the chromatographic medium and positioned so the liquid can be applied to the chromatographic medium only through a first application area substantially smaller than the area of the chromatographic medium and located at a point removed from the ends of the chromatographic medium;
  (d) an applicator adjacent to the first barrier, the applicator containing a labeled specific binding partner to the analyte in resolubilizable form, the applicator extending past the barrier to apply liquid to the chromatographic medium at the first application area; and
  (e) a second substantially fluid-impermeable barrier adjacent to the applicator and positioned so that liquid can be applied to the applicator only through a second application area substantially smaller than the area of the chromatographic medium and located adjacent to the second end of the chromatographic medium; and (2) a second opposable component including a second application zone.

The first and second opposable components are configured so that bringing the first and second opposable components into opposition results in the sample preparation zone being in contact with the second barrier and with the second application area. Thus, sample in the sample preparation area is applied to the applicator through the second application area. The sample traverses substantially the entire length of the applicator in order to apply the sample and the resolubilized labeled specific binding partner to the chromatographic medium through the first application area.

Figure 10A:
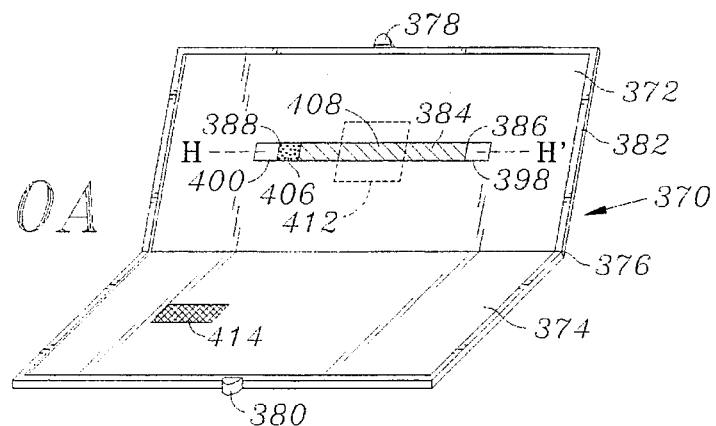
FIG. 10A is a drawing of a two-component assay device according to the present invention employing non-isotropic flow in several elements, incorporating two barriers, an applicator, and a chromatographic medium.
Figure 10B:
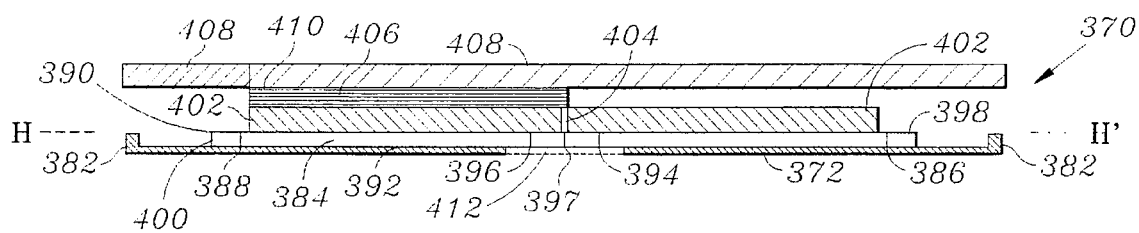
FIG. 10B is a cross-section along line H–H' of a side view of the first component of the two-component assay device of FIG. 10A, showing the detail of the chromatographic medium, the two barriers, and the applicator.

Such a non-isotropic flow device suitable for a sandwich immunoassay is depicted in FIGS. 10A and 10B. The arrangement of the two components is shown in FIG. 10A, and a cross-section along line H–H' of the first component, showing the detail of the chromatographic medium, the first barrier, the applicator, and the second barrier, is shown in FIG. 10B. The device 370 comprises first and second opposable components 372 and 374 joined by a hinge 376. The first and second opposable components 372 and 374 have locks 378 and 380 and are surrounded by a gasket 382. The first opposable component 372 includes a chromatographic medium 384 with first and second ends 386 and 388 and first and second surfaces 390 and 392. The chromatographic medium 384 has immobilized thereon in discrete non-overlapping areas a detection zone 394, and preferably, a control zone 396. The detection zone 394 contains a specific binding partner to the analyte. The control zone 396 contains analyte or analogue thereof as described above. The detection zone 394 is located between a point 397 removed from the ends of the chromatographic medium 384 and the first end 386 of the chromatographic medium 384, and the control zone 396 is located between the point 397 and the second end 388 of the chromatographic medium 384. Typically the point 397 removed from the ends of the chromatographic medium 384 is the midpoint of the chromatographic medium 384, and the detection zone 394 and the control zone 396 are equidistant from the midpoint of the chromatographic medium. However, this is not required.

The first opposable component 372 further includes a first absorber 398 in operable contact with the first end 386 of the chromatographic medium 384, and, if the control zone is present, a second absorber 400 can be in operable contact with the second end 388 of the chromatographic medium 384. However, this second absorber is not required and need not be present in all applications.

The first opposable component 372 also includes a first substantially fluid-impermeable barrier 402 adjacent to the first surface 390 of the chromatographic medium 384. The first barrier 402 is positioned so that liquid can be applied to the chromatographic medium 384 only through a first application area 404 substantially smaller than the area of the chromatographic medium 384. The first application area 404 is located at the point 397. Typically, the first application area 404 is located at the midpoint of the chromatographic medium 384. The first opposable component 372 also includes an applicator 406 adjacent to the first barrier 402 and extending past the first barrier 402 to apply liquid to the chromatographic medium 384 at the first application area 404. The applicator 406 contains a labeled specific binding partner to the analyte in resolubilizable form.

The first opposable component 372 also includes a second substantially fluid-impermeable barrier 408 adjacent to the applicator 406. Liquid can be applied to the applicator 406 only through a second application area 410 substantially smaller than the area of the chromatographic medium 384 and located adjacent to the second end 388 of the chromatographic medium 384. The first opposable component 372 also includes a window 412 to allow viewing of the chromatographic medium 384.

The second opposable component 374 includes a sample preparation zone 414 which can contain at least one reagent for treatment of the sample.

In use, a sample is applied to the sample preparation zone 414 on the second opposable component 374. The first and second opposable components 372 and 374 are then brought into opposition so that the test sample is transferred to the applicator 406 through the second application area 410. The sample transferred to the applicator 406 then resolubilizes the labeled specific binding partner in the applicator 406 and then traverses substantially the entire length of the applicator 406 to apply the sample and the resolubilized labeled specific binding partner to the chromatographic medium 384 through the first application area 404. Chromatography and detection of the analyte then take place as discussed above. Note that flow in the chromatographic medium itself is actually isotropic, although flow is not isotropic in a number of the elements.

Devices Employing Direct Absorption of Analyte to the Chromatographic Medium

Some antigens bind strongly and nonspecifically to materials commonly used as solid phases for immunoassays, such as nylon. These antigens tend to be hydrophobic, such as *Chlamydia trachomatis* lipopolysaccharide (LPS) antigens and other complex lipids. Such antigens can be bound to the chromatographic medium by an assay device according to the present invention and then detected with the appropriate labeled specific binding partner, such as a labeled antibody to the antigen. This is a single antibody immunoassay, not a sandwich immunoassay. In effect, the chromatographic medium itself takes the place of the first antibody in a conventional sandwich immunoassay.

An assay device according to the present invention suitable for performing assays involving direct immobilization of analyte on the chromatographic medium comprises:

(1) a first opposable component including:
 (a) a planar chromatographic medium having first and second ends and first and second surfaces, the chromatographic medium having an affinity for the analyte sufficient to immobilize the analyte from an aqueous solution containing the analyte on the chromatographic medium;

9555/118D-157C (b) an applicator in operable contact with the first end of the chromatographic medium, the applicator containing a labeled specific binding partner to the analyte in a form that can be resolubilized by the addition of an aqueous liquid to the applicator;
 (c) an absorber in operable contact with the second end of the chromatographic medium; and
 (d) a substantially fluid-impermeable barrier adjacent to the first surface of the chromatographic medium and having an aperture therethrough for application of liquid to the chromatographic medium, the aperture being substantially smaller in area than the barrier so that liquid can enter the chromatographic medium in the area covered by the barrier only through the aperture; and (2) a second opposable component including a sample preparation zone.

In this device, the first and second opposable components are configured so that bringing the first and second opposable components into opposition results in the sample preparation zone being in contact with the barrier so that the sample in the sample preparation zone is applied to the chromatographic medium. Analyte in the test sample is immobilized on the chromatographic medium in the vicinity of the aperture. In this device, unlike previous devices according to the present invention, flow in the chromatographic medium itself is from one end of the medium to the other and not from a point removed from the ends of the medium to each end.

The chromatographic medium itself can be nylon if the antigen is a lipopolysaccharide.

Figure 11A:
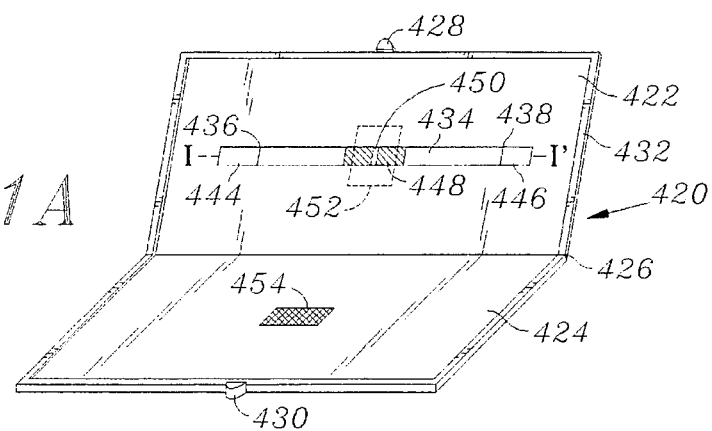
FIG. 11A is a drawing of a two-component assay device according to the present invention suitable for assay of an analyte that binds directly to the chromatographic medium such as a lipopolysaccharide.
Figure 11B:
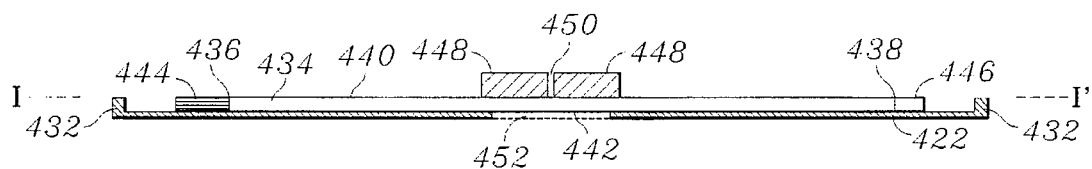
FIG. 11B is a cross-section along line I–I' of the first component of the two-component assay device of FIG. 10A, showing the detail of the chromatographic medium, the applicator, the absorber, the barrier, and the aperture.

A device suitable for an assay involving binding of the analyte to the chromatographic medium is depicted in FIGS. 11A and 11B. FIG. 11A shows the arrangement of the two components of the device, and FIG. 11B shows a cross-section along line I–I' of the first component, showing the detail of the chromatographic medium, the applicator, the barrier, and the aperture. The assay device 420 has first and second opposable components 422 and 424, joined by a hinge 426. The first and second opposable components contain locks 428 and 430, and a gasket 432 surrounds the first and second opposable components 422 and 424 when they are brought into opposition. The first opposable component 422 has a chromatographic medium 434, with a first end 436 and a second end 438. The chromatographic medium 434 has a first surface 440 and a second surface 442. The first opposable component 422 also includes an applicator 444 in operable contact with the first end 436 of the chromatographic medium 434 and an absorber 446 in operable contact with the second end 438 of the chromatographic medium 434. The first opposable component 422 also includes a substantially fluid-impermeable barrier 448 adjacent to the first surface 442 of the chromatographic medium and having an aperture 450 therethrough for application of liquid to the chromatographic medium 434. Preferably, the first opposable component also includes a window 452 adjacent to the second surface 444 of the chromatographic medium 434 for viewing of the chromatographic medium 434.

The second opposable component 424 includes a sample preparation zone 454.

In use, sample is added to the sample preparation zone 454 of the second opposable component 424, and an aqueous liquid is added to the applicator 444 through solubilized labeled specific binding partner. The first and second opposable components 422 and 424 are then brought into opposition so that the test sample is applied to the chromatographic medium 434 through the aperture 450 in the barrier 448. Then, any analyte in the sample is allowed to bind to the chromatographic medium 434 in the vicinity of the aperture. The resolubilized labeled specific binding partner is allowed to migrate through the chromatographic medium 434 from the first end 436 toward the second end 438. The labeled specific binding partner can react with analyte bound to the chromatographic medium 434 for detection. In this case, the detection zone is actually formed by analyte binding to the chromatographic medium 434 in the vicinity of the aperture 450 in the barrier 448.

II. SEQUENTIAL IMMUNOCHROMATOGRAPHY

In some applications, particularly in serological assays, it is desirable that the capture step, i.e., by a specific binding partner to the analyte immobilized on the solid support, occurs before the labeling step. For example, in a immunochromatographic assay for detecting IgG antibody to *Helicobacter pylori* in human serum, serum is run past the band of *H. pylori* antigen immobilized on a solid phase chromatographic medium. Specific IgG in the serum binds to the immobilized antigen. After withdrawal of serum containing non-specific IgG, anti-human IgG labeled with a detectable label, such as a visible dye (the conjugate) is then allowed to migrate past the antigen band and any bound IgG is labeled with the detectable label.

Conventional one-step linear chromatographic assays are unsuitable for the sequential type of assay unless a time-consuming and inconvenient wash step is incorporated in the procedure. If such a wash step is not incorporated, a large excess of human IgG not specific for *H. pylori* will react with the conjugate. This will leave a high background of label in the chromatographic medium and may exhaust the conjugate before it has had a chance to react with the anti-*H. pylori* antibody bound to the immobilized *H. pylori* antigen.

It would be desirable to have a chromatographic assay device that can perform a sequential immunoassay so that reaction of the antibody to be detected with the corresponding analyte immobilized on the chromatographic medium is first allowed to go to completion. Then, in a second step, the labeled conjugate is applied to detect the analyte, such as the anti-*H. pylori* antibody.

A device suitable for performing sequential immunoassay comprises:

(1) a first opposable component including:
  (a) a planar chromatographic medium as described above, having a specific binding partner to the analyte immobilized thereon in a detection zone substantially smaller than the area of the chromatographic medium;
  (b) a sample preparation zone in operable contact with the first end of the chromatographic medium;
  (c) a first absorber in operable contact with the second end of the chromatographic medium; and
  (d) a substantially fluid-impermeable barrier adjacent to the first surface of the chromatographic medium and having an aperture therethrough for application of liquid to the chromatographic medium, the aperture being substantially smaller in area than the barrier so that liquid can enter the chromatographic medium in the area covered by the barrier only through the aperture; and (2) a second opposable component including:
  (a) an applicator containing a specific binding partner to the analyte in resolubilizable form, the applicator positioned such that when the first and second opposable component are brought into opposition, the applicator is in contact with the barrier so that resolubilized labeled specific binding partner to the analyte is applied through the aperture in the barrier to the chromatographic medium; and
  (b) second and third absorbers positioned such that when the first and second opposable components are brought in to opposition, the second absorber is in operable contact with a portion of the chromatographic medium between the barrier and the first end of the chromatographic medium and the third absorber is in operable contact with a portion of the chromatographic medium between the barrier and the second end of the chromatographic medium between the barrier and the second end of the chromatographic medium so that the second and third absorbers can remove fluid from the chromatographic medium.

When the first and second opposable components are brought into opposition, therefore, fluid flow is from the aperture in the barrier outward to the second and third absorbers in both directions along the chromatography medium.

Typically, the assay device further comprises a substantially transparent backing adjacent to the second surface of the chromatographic medium, as described above.

The sample preparation zone, as described above, can contain at least one reagent for treatment of the sample before the sample is applied to the chromatographic medium. Unlike other devices according to the present invention as described above in which the sample preparation zone is on the second opposable component, in this device the application of the sample to the chromatographic medium occurs without bringing the first and second opposable components into opposition. Thus, the concentration of any reagent used for treatment of the sample is adjusted accordingly.

The chromatographic medium can further include a control zone of analyte or analog thereof immobilized on the chromatographic medium in an area substantially smaller than the chromatographic medium and not overlapping with the detection zone. When the chromatographic medium contains both a detection zone and a control zone, the detection zone is positioned between the aperture and the first end of the chromatographic medium. The control zone is positioned between the aperture and the second end of the chromatographic medium. Preferably, the detection zone is positioned between the aperture and the portion of the chromatographic medium contacted by the second absorber, and the control zone is positioned between the aperture and the portion of the chromatographic medium contacted by the third absorber, to insure that a sufficient quantity of resolubilized labeled specific binding partner reaches both the detection and control zones.

Figure 12A:
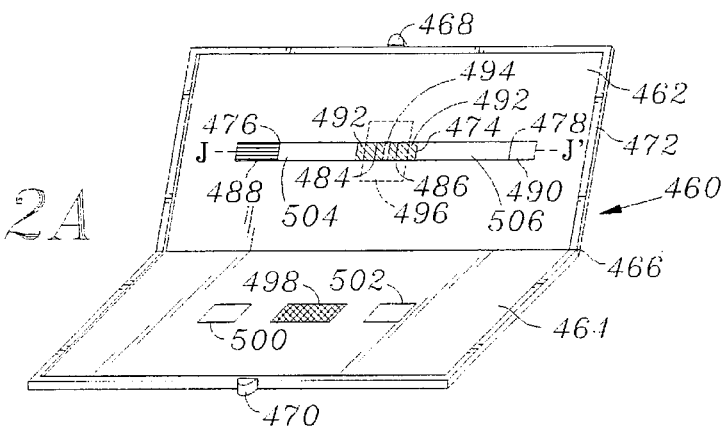
FIG. 12A is a drawing of a two-component assay device according to the present invention suitable for sequential assay of an analyte in which the capture by immobilized antibody of the antigen to be assayed occurs prior to the labeling step.
Figure 12B:
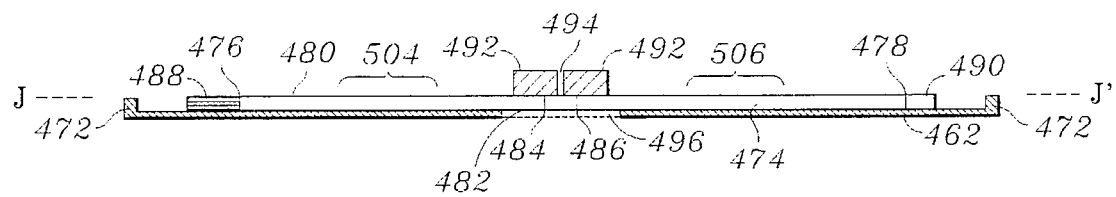
FIG. 12B is a cross-section along line J–J' of the first component of the two-component assay device of FIG. 12A, showing the detail of the chromatographic medium, the applicator, the absorber, the barrier, and the aperture.

This device is depicted in FIGS. 12A and 12B. FIG. 12A shows the arrangement of the two components of the device, and FIG. 12B shows a cross-section along line J–J' of the first component, showing the detail of the chromatographic medium, the applicator, the first absorber, the barrier, and the aperture. The assay device 460 has a first opposable component 462 and a second opposable component 464, joined by a hinge 466. The first and second opposable components contain locks 468 and 470, and a gasket 472 surrounds the first and second opposable components 462 and 464 when they are brought into opposition. The first opposable component 462 includes a substantially planar chromatographic medium 474 with a first end 476, a second end 478, and first and second surfaces 480 and 482. The chromatographic medium also includes a detection zone 484 containing an immobilized specific binding partner to the analyte, and, optionally, a control zone 486 containing immobilized analyte.

The first opposable component 462 also includes a sample preparation zone 488 in operable contact with the first end 476 of the chromatographic medium 474. The sample preparation zone 488 can contain at least one reagent for treatment of the sample, as described above. The first opposable component 462 also includes a first absorber 490 in operable contact with the second end 478 of the chromatographic medium 474.

The first opposable component 462 further includes a substantially fluid-impermeable barrier 492 adjacent to the first surface 480 of the chromatographic medium 474. The barrier 492 has an aperture 494 therethrough for application of liquid to the chromatographic medium 474. The aperture 494 is substantially smaller in area than the barrier 492 so that liquid can enter the chromatographic medium 474 in the area covered by the barrier 492 only through the aperture 494. However, in this device, liquid can also enter the chromatographic medium 474 at the first end 476 from the sample preparation zone 488.

The first opposable component also includes a window 496 adjacent to the second surface 482 of the chromatographic medium 474 for viewing of the chromatographic medium 474.

The second opposable component 464 includes an applicator 498 containing a labeled specific binding partner to the analyte in resolubilizable form. The applicator 498 is positioned such that when the first and second opposable components 462 and 464 are brought into opposition, the applicator 498 is in contact with the barrier 492 so that resolubilized labeled specific binding partner is applied through the aperture 494 in the barrier 492 to the chromatographic medium 474. The second opposable component 464 also includes second and third absorbers 500 and 502 positioned such that, when the first and second opposable components 462 and 464 are brought into opposition, the second absorber 500 is in operable contact with a portion 504 of the chromatographic medium 474 between the barrier 492 and the first end 476 of the chromatographic medium 474, and the third absorber 502 is in opposable contact with a portion 506 of the chromatographic medium 474 between the barrier 492 and the second end 478 of the chromatographic medium 474. This allows the second and third absorbers 500 and 502 to remove fluid from the chromatographic medium 474.

In use, the sample is applied to the sample preparation zone 488 and the sample is allowed to migrate through the chromatographic medium 474, including the detection zone 476. An aqueous liquid is then added to the applicator 498 on the second opposable component 464 to resolubilize the labeled specific binding partner to the analyte. The first and second opposable components 462 and 464 are then brought into opposition, to apply the resolubilized labeled specific binding partner to the aperture 494 in the barrier 492. Simultaneously, the second and third absorbers 500 and 502 are applied to the chromatographic medium 474 to remove fluid from the chromatographic medium 474. If analyte is present in the test sample, a ternary complex is formed at the detection zone 476 for detection of the analyte.

III. AMPLIFIED IMMUNOCHROMATOGRAPHY

Another aspect of the present invention is a device performing amplified immunochromatography. Such a device depends on amplification of colloidal gold staining with silver.

A. Principles of Silver Amplification

Silver can be used to amplify colloidal gold as a label for a compound participating in a specific binding reaction, i.e., as a specific binding partner such as an antigen, hapten, antibody, or antibody fragment. Gold can catalyze the reduction of a soluble silver salt to metallic silver, producing silver shells that surround the gold label so that larger areas are visible. This amplifies the signal that is bound in a ternary complex at the detection zone. The soluble silver salt is preferably silver lactate. The reducing agent is typically a quinone such as hydroquinone.

B. Devices Employing Silver Amplification

The present invention incorporates two types of devices employing silver amplification. The first type of device includes a gold-sol labeled specific binding partner incorporated in resolubilizable form on the first opposable component adjacent to a sample preparation zone. In this device, the second opposable component includes an applicator containing a soluble silver salt and a reducing agent. The second type of device is particularly adapted to the determination of an analyte in a sample on a swab. In this device, the swab is inserted into the second opposable component, and the soluble silver salt and reducing agent are provided by an insert positioned in the device.

1. Device With Silver Salt Incorporated in Applicator on Second Opposable Component One former device employing silver amplification includes a soluble silver salt and a reducing agent on an applicator in the second opposable component. This device comprises:

(1) a first opposable component including:
  (a) a planar chromatographic medium having a first end, a second end, and top and bottom surfaces, having a specific binding partner to the analyte immobilized thereon in a detection zone as described above;
  (b) an absorber in operable contact with the second end of the chromatographic medium;
  (c) a conductor in operable contact with the first end of the chromatographic medium;
  (d) a conjugate zone containing a specific binding partner to the analyte labeled with a gold sol in a form that can be resolubilized by the addition of an aqueous liquid to the conjugate zone, the conjugate zone in direct contact with the conductor and in indirect contact with the first end of the chromatographic medium;
  (e) a sample preparation zone for application of a test sample, the sample preparation zone being in direct contact with the conjugate zone, the conductor, conjugate zone, and sample preparation zone being positioned so that the conjugate zone bridges the sample preparation zone and the conductor; and
  (f) a substantially fluid-impermeable barrier adjacent to the second surface of the chromatographic medium and having an aperture therethrough for application of liquid to the chromatographic medium; and (2) a second opposable component including:
  (a) an applicator containing, in a form that can be resolubilized by the addition of an aqueous liquid to the applicator: (i) a soluble silver salt and (2) a reducing agent, the applicator positioned so that when the first and second opposable components are brought into opposition, the applicator is in contact with the barrier so that the resolubilized silver salt and reducing agent are applied through the aperture in the barrier to the chromatographic medium; and
  (b) second and third absorbers positioned that when the first and second opposable components are brought into opposition, the absorber is in operable contact with a portion of the chromatographic medium between the barrier and the first end of the chromatographic medium, and the third absorber is in operable contact with a portion of the chromatographic medium between the barrier and the second end of the chromatographic medium so that the second and third absorbers remove fluid from the chromatographic medium.

Figure 13A:
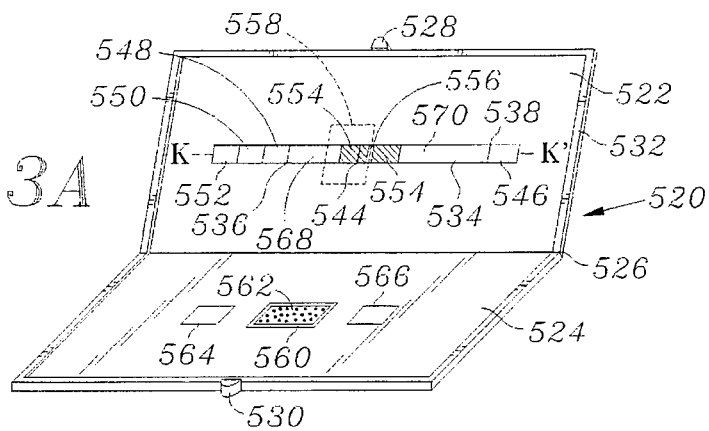
FIG. 13A is a drawing of a two-component assay device according to the present invention suitable for performing an amplified assay of an analyte in which the analyte is detected by gold labeling and silver is used to amplify the signal of the gold label.
Figure 13B:
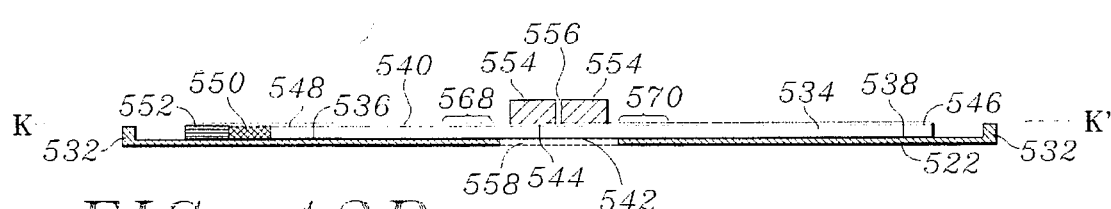
FIG. 13B is a cross-section along line K–K' of the first component of the two-component assay device of FIG. 13A, showing the detail of the chromatographic medium, elements in direct or indirect contact with the chromatographic medium, the barrier, and the aperture.

This device is depicted in FIGS. 13A and 13B. FIG. 13A shows the arrangement of the two components of the device, and FIG. 13B shows a cross-section along line K–K' of the first component, showing the detail of the chromatographic medium, the conductor, the conjugate zone, the sample preparation zone, the first absorber, the barrier, and the aperture. The device 520 has a first opposable component 522 and a second opposable component 524, joined by a hinge 526. The first and second opposable components 522 and 524 have engagers such as locks 528 and 530 to hold the components when they are placed into opposition, and a gasket 532 surrounds the first and second opposable components 522 and 524 when they are brought into opposition.

The first opposable component 522 has a chromatographic medium 534. The chromatographic medium 534 has first and second ends 536 and 538 and first and second surfaces 540 and 542. The chromatographic medium 534 also has a detection zone 544 substantially smaller than the area of the chromatographic medium 534. The detection zone includes a specific binding partner to the analyte immobilized thereon.

The first opposable component 522 also includes an absorber 546 in operable contact with the second end 536 of the chromatographic medium 532, and a conductor 548 in operable contact with the first end 536 of the chromatographic medium 534.

The first opposable component 522 also includes a conjugate zone 550 containing a specific binding partner to the analyte labeled with a gold sol in a form that can be resolubilized by the addition of an aqueous liquid to the conjugate zone 550. The conjugate zone 550 is in direct contact with the conductor 548 and is in indirect contact with the first end 536 of the chromatographic medium 534.

The first opposable component 522 also includes a sample preparation zone 552 for application of a test sample. The sample preparation zone 552 is in direct contact with the conjugate zone 550. The conductor 548, the conjugate zone 550, and the sample preparation zone 552 are positioned on the first opposable component 522 so that the conjugate zone 550 bridges the sample preparation zone 552 and the conductor 548.

The first opposable component 522 also includes a substantially fluid-impermeable barrier 554 adjacent to the first surface 540 of the chromatographic medium 534. The barrier 554 has an aperture 556 therethrough for application of liquid to the chromatographic medium 534. The aperture 556 is substantially smaller in area than the barrier 554 so that liquid can enter the chromatographic medium 534 in the area covered by the barrier 554 only through the aperture 556. However, in this device, liquid can also enter the chromatographic medium 534 through the conductor 548.

The first opposable component 522 also includes a window 558 adjacent to the second surface 542 of the chromatographic medium 534 for viewing of the chromatographic medium 534.

The second opposable component 524 includes an applicator 560 containing an amplifier zone 562. The amplifier zone 562 contains, in a form that can be resolubilized by the addition of the aqueous liquid to the applicator 556: (1) a soluble silver salt and (2) a reducing agent. The applicator 560 is positioned so that when the first and second opposable component 522 and 524 are brought into opposition, the applicator 560 is in contact with the barrier 554 so that the resolubilized silver salt and the reducing agent in the amplifier zone 562 are applied through the aperture 556 in the barrier 554 to the chromatographic medium 534. The second opposable component 524 also includes second and third absorbers 564 and 566. The second and third absorbers 564 and 566 are positioned such that when the first and second opposable component 522 and 524 are brought into opposition, the second absorber 564 is in operable contact with a portion 568 of the chromatographic medium 534 between the barrier 554 and the first end 536 of the chromatographic medium 534, and the third absorber 566 is in operable contact with a portion 570 of the chromatographic medium 534 between the barrier 554 and the second end 538 of the chromatographic medium. Thus, the second and third absorbers 564 and 566 remove fluid from the chromatographic medium.

In use, the sample is applied to the sample preparation zone 552 of the device 520. The sample is allowed to flow through the conjugate zone 550 to resolubilize the labeled specific binding partner in the conjugate zone 550. The sample and the resolubilized labeled specific binding partner are then allowed to enter the chromatographic medium 534 through the conductor 548 and to flow through at least a portion of the chromatographic medium 534 including the detection zone 544. An aqueous liquid is then added to the applicator 560 on the second opposable component 524 to resolubilize the soluble silver salt and the reducing agent in the amplifier zone 562. The first and second opposable components 522 and 524 are then brought into opposition to apply the resolubilized silver salt and the reducing agent to the chromatographic medium 534 through the aperture 556 in the barrier 554 and to bring the second and third absorbers 564 and 566 into operable contact with the portions 568 and 570 of the chromatographic medium 534 to withdraw fluid from the chromatographic medium 534. The resolubilized silver salt and the reducing agent are then allowed to flow through at least a portion of the chromatographic medium 534 including the detection zone 544 to deposit silver around the gold in the gold label of the labeled specific binding partner. Thus, any ternary complex bound at the detection zone 544 has silver bound to it to amplify the signal.

2. Device With Two-Sector Applicator to Provide Wash

Another version of an assay device according to the present invention employing silver amplification of a signal generated by gold sol has an applicator including two sectors to provide a wash of the chromatographic medium before the aqueous silver salt and reducing agent are applied to the chromatographic medium.

This device comprises:

(1) a first opposable component including:
  (a) a chromatographic medium having a first end, a second end, first and second surfaces, and a detection zone with a specific binding partner to the analyte as described above;
  (b) an absorber in operable contact with the second end of the chromatographic medium;
  (c) a conductor in operable contact with the first end of the chromatographic medium;
  (d) a conjugate zone containing a specific binding partner to the analyte labeled with a gold sol that can be resolubilized by the addition of an aqueous liquid to the conjugate zone, the conjugate zone being in direct contact with the conductor and being in indirect contact with the first end of the chromatographic medium;
  (e) a sample preparation zone for application of a test sample, the sample preparation zone being in direct contact with the conjugate zone, the conductor, conjugate zone and sample preparation zone being positioned so that the conjugate zone bridges the sample preparation zone and the conductor; and
  (f) a substantially fluid-impermeable barrier adjacent to the top surface of the chromatographic medium and having an aperture cut therethrough substantially smaller in area than the barrier as described above; and (2) a second opposable component including:
  (a) an applicator including two sectors:
    (i) a first sector for receiving an aqueous liquid; and
    (ii) a second sector containing a soluble silver salt and a reducing agent in resolubilizable form; and
  (b) second and third absorbers.

The applicator is positioned so that when the first and second opposable components are brought into opposition, the first sector of the applicator is in direct contact with the aperture in the barrier and the second sector of the applicator is in indirect contact with the aperture so that the aqueous liquid is applied first to the chromatographic medium to provide a wash, followed by the aqueous silver salt and the reducing agent. The second and third absorbers are positioned such that when the first and second opposable component are brought into opposition, the second absorber is in operable contact with a portion of the chromatographic medium between the barrier and the first end of the chromatographic medium and the third absorber is in operable contact with a portion of the chromatographic medium between the barrier and the second end of the chromatographic medium, so that the second and third absorbers remove fluid from the chromatographic medium.

This device is depicted in FIGS. 14A and 14B. FIG. 14A shows the arrangement of the two components of the device, and FIG. 14B shows a cross-section along line L–L' of the first component, showing the detail of the chromatographic medium, elements in direct or indirect contact with the chromatographic medium, the barrier, and the aperture. The chromatographic assay device 580 has a first opposable component 582 and a second opposable component 584 joined by a hinge 586. The first and second opposable components 582 and 584 have engagers such as locks 588 and 590 to hold the opposable components together. A gasket 592 surrounds the first and second opposable components 582 and 584 when they are brought into opposition.

The first opposable component 582 has a chromatographic medium 594, having first and second ends 596 and 598 and first and second surfaces 600 and 602. The chromatographic medium 594 has a detection zone 604 of specific binding partner to the analyte immobilized thereon. The detection zone 604 is substantially smaller in area than the chromatographic medium 594.

The first opposable component 582 also includes an absorber 606 in operable contact with the second end 598 of the chromatographic medium 594, and a conductor 608 in operable contact with the first end 596 of the chromatographic medium 594. The first opposable component 582 also includes a conjugate zone 610 containing a specific binding partner to the analyte labeled with a gold sol in resolubilizable form. The conjugate zone 610 is in direct contact with the conductor 608 and is in indirect contact with the first end 596 of the chromatographic medium 594.

The first opposable component 582 also includes a sample preparation zone 612 for application of a test sample. The sample preparation zone 612 is in direct contact with the conjugate zone 610. The sample preparation zone 612 can contain at least one reagent for treatment of the sample. The conductor 608, the conjugate zone 610, and the sample preparation zone 612 are positioned so that the conjugate zone 610 bridges the sample preparation zone 612 and the conductor 608.

The first opposable component 582 also includes a substantially fluid-impermeable barrier 614 adjacent to the first surface 600 of the chromatographic medium 594. The barrier 614 has an aperture 616 therethrough for application of liquid to the chromatographic medium 594. The aperture 616 is substantially smaller in area than the barrier 614 so that liquid can enter the portion of the chromatographic medium 594 adjacent to the barrier 614 only through the aperture 616.

The first opposable component 582 also includes a window 618 adjacent to the second surface 602 of the chromatographic medium 594 for viewing of the chromatographic medium 594.

The second opposable component 584 includes an applicator 620 that includes two sectors: (1) a first sector 622 for receiving an aqueous liquid; and (2) a second sector 624 containing, in resolubilizable form, a soluble silver salt and a reducing agent. The applicator 620 is positioned so that when the first and second opposable components 582 and 584 are brought into opposition, the first sector 622 of the applicator 620 is in direct contact with the aperture 616 in the barrier 614, and the second sector 624 of the applicator 620 is in indirect contact with the aperture 616 so that the aqueous liquid is applied first to the chromatographic medium 594 to provide a wash, followed by the resolubilized silver salt and the reducing agent. The second opposable component 584 also includes a second absorber 626 and a third absorber 628. The second and third absorbers 626 and 628 are positioned such that when the first and second opposable components 582 and 584 are brought into opposition, the second absorber 626 is in operable contact with a portion 630 of the chromatographic medium 630 between the barrier 614 and the first end 596 of the chromatographic medium 594, and the third absorber 628 is in operable contact with a portion 632 of the chromatographic medium between the barrier 614 and the second end 598 of the chromatographic medium 594. This is to enable the second and third absorbers 626 and 628 to remove fluid from the chromatographic medium 594.

In use, the sample is applied to the sample preparation zone 612 of the device 580. The sample is allowed to flow through the conjugate zone 610 to resolubilize the labeled specific binding partner to the analyte in the conjugate zone 610. The sample and the resolubilized labeled specific binding partner are then allowed to enter the chromatographic medium 594 through the conductor 608 and to flow through at least a portion of the chromatographic medium 594, including the detection zone 604. This forms a binary complex between any analyte present in the test sample and the immobilized specific binding partner at the detection zone 604. An aqueous liquid is then added to the first and second sectors 622 and 624 of the applicator 620. This resolubilizes the soluble silver salt and the reducing agent in the second sector 624 of the applicator 620. The first and second opposable components 582 and 584 are then brought into opposition to apply the aqueous liquid in the first sector 622 of the applicator 620 to the chromatographic medium 594 through the aperture 616 as a wash, followed by the application of the resolubilized silver salt and the reducing agent to the chromatographic medium 592. This also brings the second and third absorbers 626 and 628 into opposable contact with the portions 630 and 632 of the chromatographic medium 594 to withdraw fluid from the chromatographic medium 594. The resolubilized silver salt and reducing agent are then allowed to flow through at least a portion of the chromatographic medium 594 including the detection zone 604 to deposit silver around the gold of the gold label enhancing the signal.

3. Device With Base Panel and Insert

Another device according to the present invention suitable for performing amplified immunochromatography is divided into two separable pieces: a base panel and an insert. The insert includes the applicator for the application of the soluble silver salt and the reducing agent.

This device comprises:
  (1) a base panel including:
    (a) a first opposable component including:
      (i) a planar chromatographic medium having a first end, a second end, and first and second surfaces, and having a specific binding partner to the analyte immobilized thereon in a detection zone as described above;

(ii) a conjugate zone containing a specific binding partner to the analyte labeled with a gold sol in resolubilizable form, the conjugate zone being in operable contact with the first end of the chromatographic medium;

(iii) a conductor in operable contact with the conjugate zone, the conjugate zone reaching the first end of the chromatographic medium and the conductor; and (iv) a substantially fluid-impermeable barrier adjacent to the first service of the chromatographic medium and having an aperture therethrough for application of liquid to the chromatographic medium as described above;

(b) a second opposable component including:

(i) a receptacle for a swab containing a test sample;

(ii) a well for addition of at least one extraction reagent to the swab; and (iii) a first absorber separated from the receptacle and the well; and (c) a receptacle for holding an insert stable against relative motion of the surfaces of the insert and of the first and second opposable components; and (2) an insert including:

(a) an applicator containing, in resolubilizable form, a soluble silver salt and a reducing agent;

(b) a second absorber;

(c) a third absorber; and (d) a protrusion for insertion into the receptacle of the base panel.

The first and second opposable components of the base panel are configured so that, when they are brought into opposition, the first absorber is brought into contact with a portion of the chromatographic medium between the barrier and the second end of the chromatographic medium, and the receptacle is brought into contact with the conductor. The insert is configured such that when the protrusion of the insert is inserted into the receptacle of the base panel, the applicator is in operable contact with the aperture, the second absorber is in operable contact with a portion of the chromatographic medium between the barrier and the first end of the chromatographic medium between the barrier and the first end of the chromatographic medium, and the third absorber is in operable contact with a portion of the chromatographic medium between the barrier and the second end of the chromatographic medium.

The receptacle for holding the insert can be in either the first or second opposable component of the base panel. Alternatively, it can be located between the first and second opposable component of the base panel, which are typically joined by a hinge as in the two-component devices described above.

A device incorporating a base panel and an insert is shown in FIGS. 15A and 15B. FIG. 15A shows the arrangement of the two components of the base panel together with the insert, and FIG. 15B shows a cross-section along line M–M' of the first component of the base panel, showing the detail of the chromatographic medium, elements in direct or indirect contact with the chromatographic medium, the barrier, and the aperture. The device 640 comprises a base panel 642 and an insert 644. The base panel 642 includes a first opposable component 646 and a second opposable component 648, joined by a hinge 650.

The first opposable component 646 of the base panel 642 includes a chromatographic medium 656. The chromatographic medium 656 has first and second ends 658 and 660 and first and second surfaces 662 and 664. The chromatographic medium 656 further incorporates a detection zone 666 containing a specific binding partner to the analyte immobilized thereto, as described above.

The first opposable component 646 of the base panel 642 includes a conjugate zone 668 containing a specific binding partner to the analyte labeled with a gold sol in resolubilizable form. The conjugate zone 668 is in operable contact with the first end 658 of the chromatographic medium 656. The first opposable component 646 of the base panel 642 further includes a conductor 670 in operable contact with the conjugate zone 668. The conjugate zone 668 bridges the first end of the chromatographic medium 658 and the conductor 670.

The first opposable component 646 also includes a substantially fluid-impermeable barrier 672 adjacent to the first surface 662 of the chromatographic medium 656 and having an aperture 674 therethrough for application of liquid to the chromatographic medium 656. The aperture 674 is substantially smaller in area than the barrier 672 so that liquid can enter the area of the chromatographic medium 656 adjacent to the barrier 672 only through the aperture 674.

The first opposable component 646 of the base panel 642 also includes a window 676 for viewing of the chromatographic medium 656.

The second opposable component 648 of the base panel 642 includes a first receptacle 678 for a swab containing a test sample, a well 680 for addition of at least one extraction reagent to the swab, and a first absorber 682 separated from the receptacle 678 and the well 680. The first and second opposable components 646 and 648 of the base panel 642 are configured so that, when they are brought into opposition, the first absorber 682 is brought into contact with a portion 684 of the chromatographic medium between the barrier 672 and the second end 660 of the chromatographic medium 656, and the first receptacle 678 is brought into contact with the conductor 670. The base panel 642 further includes a second receptacle 686 for the insert 644. The first and second opposable components 646 and 648 can be held together by an engager 688 such as a resealable label, a Velcro™ closure, or other reversibly engageable closure.

The insert 644 includes an applicator 690 containing, in resolubilizable form, a soluble silver salt, and a reducing agent. The insert 644 further includes a second absorber 692 and a third absorber 694, as well as a protrusion 696 for insertion into the second receptacle 686 of the base panel 642. The insert 644 is configured such that when the protrusion 696 is inserted into the second receptacle 686 of the base panel, the applicator 690 is in operable contact with the aperture 674 to apply the contents of the applicator 690 to the chromatographic medium 656 through the aperture 674. The second absorber 692 is in operable contact with a portion 698 of the chromatographic medium 656 between the barrier 672 and the first end 658 of the chromatographic medium 656. The third absorber 694 is in operable contact with the portion 684 of the chromatographic medium between the barrier 672 and the second end 660 of the chromatographic medium 656; i.e., the third absorber 694 is in the same position as the first absorber 682 when the first and second opposable components 646 and 648 were in opposition prior to the insertion of the insert 644.

The insert 644 is inserted by the protrusion 696 into the second receptacle 686 in such a manner that the surfaces of the insert 644 and the first and second opposable components 646 and 648 of the base panel 642 are stabilized against relative motion.

In use, a swab containing a test sample is placed in the first receptacle 678 of the second opposable component 648 of the base panel 642 of the device 640. At least one extraction reagent is applied to the well 680 to extract analyte from the swab. The first and second opposable component 646 and 648 of the base panel 642 are then brought into opposition. The swab in the first receptacle 678 is in contact with the conductor 670 to apply the extracted analyte to the conductor 670. The extracted sample is then allowed to flow through the conjugate zone 668 to resolubilize the labeled specific binding partner therein. The extracted sample and the resolubilized labeled specific binding partner are then allowed to enter the chromatographic medium 656 and to flow through at least a portion of the chromatographic medium 656 including the detection zone 666. An aqueous liquid is then added to the applicator 690 of the insert 644 to resolubilize the soluble silver salt and the reducing agent. The protrusion 696 of the insert 644 is inserted into the second receptacle 686 of the base panel 642, and the insert is positioned so that the applicator 690 is in contact with the aperture 674 in the barrier to apply the contents of the applicator 690 to the chromatographic medium 656 to the aperture 674. The second and third absorbers 692 and 694 are in contact with portions of the chromatographic medium 656. The resolubilized silver salt and reducing agent are then allowed to flow through at least a portion of the chromatographic medium 656 including the detection zone 666 to amplify the signal for detection of the analyte.

IV. ENZYME IMMUNOCHROMATOGRAPHY

A powerful technique for determination of analytes by specific binding reactions is enzyme immunochromatography. In this technique, one of the components in a specific binding reaction such as an antibody, antigen, or hapten, is labeled with an enzyme. The complex between that component and its specific binding partner is detected by supplying a substrate to the enzyme and observing a detectable product produced by the reaction catalyzed by the enzyme. Although this is in principle a powerful technique, conventional immunochromatography is not suitable for enzyme labels, because the enzyme substrate must be added following the migration of the enzyme. Residual enzyme in the test strip then results in background color development that makes the reading of results very difficult if not impossible. However, devices according to the present invention can be adapted to perform enzyme immunochromatography, as described below.

A. Principles of Enzyme Labeling

The principles of enzyme labeling are well understood in the art and are disclosed, for example, in P. Tijssen, "Practice and Theory of Enzyme Immunoassay," (Elsevier, Amsterdam, 1985), pp. 173–296, incorporated herein by this reference, or in E. Harlow & V. Lane, "Antibodies: A Laboratory Manual" (Cold Spring Harbor, New York, 1988), pp. 592–599, incorporated herein by this reference. Among the parameters well understood in the art are the choice of enzyme and substrate, and the method used for coupling the specific binding partner to the enzyme.

1. Choice of Enzymes and Substrates

A number of enzymes whose properties are well known are useful for enzyme immunochromatography. For each of these enzymes, at least one substrate can be used. Preferably, the substrate is one that yields an insoluble product as a result of the reaction catalyzed by the enzyme. Such an insoluble product can adhere to the chromatographic medium at the detection zone to allow detection.

Among the enzymes particularly useful for enzyme immunochromatography are horseradish peroxidase and alkaline phosphatase. For horseradish peroxidase, suitable substrates that form insoluble products include 4-chloro-1-naphthol, 3 amino-9-ethylcarbazole, and diaminobenzidine (3,3',4,4'-tetraaminobiphenyl) Diaminobenzidine can be used in the presence of cobalt or nickel ions. For alkaline phosphatase, a suitable substrate producing an insoluble product is a mixture of bromochloroindolyl phosphate-nitro blue tetrazolium. Other enzymes and substrates suitable for use in immunochromatography are known in the art.

2. Coupling of Enzymes to Members of Specific Binding Pair

In carrying out immunochromatography, at least one member of a specific binding pair involving the analyte is covalently coupled to the enzyme used to produce the detectable product. Typically, if the analyte is an antigen or a hapten, an antibody that specifically binds the antigen or hapten is covalently coupled to the enzyme. However, immunochromatography can also be carried out to detect antibodies in which case an antigen or a hapten to which the antibody binds specifically is coupled to the enzyme. Among the reagents useful for coupling antibodies to enzymes are sodium periodate, glutaraldehyde, p-benzoquinone, N,N'-o-phenylenedimaleimide, bis-succinic acid N-hydroxysuccinimic ester, carbodiodiimides, tolylene 2,4-diisocyanate, 4,4'-difluoro-3,3'-dinitrophenyl sulfone, 4-(N-maleimidomethyl)-cyclohexane-1-carboyxlic acid N-hydroxysuccinimide ester, m-maleimidobenzoyl-N-hydroxysuccinimide ester, the N-hydroxysuccinimide ester of p-formylbenzoic acid, and N-succinimidyl-3-(2-pyridyldithio) propionate. Other reagents suitable for conjugation are known in the art.

The conjugation of antigens and haptens to proteins, including enzymes, is well known in the art and is described, for example, at pp. 279–296 of P. Tijssen, supra.

Briefly, haptens or antigens containing carboxyl groups or that can be carboxylated can be coupled by the mixed anhydride reaction, by reaction with a water-soluble carbodiimide, or with N-hydroxysuccinimide. Carboxylation can be performed by reactions such as alkylation of oxygen or nitrogen substituents with haloesters, followed by hydrolysis of the ester, or the formation of hemisuccinate esters or carboxymethyloximes on hydroxyl or ketone groups of steroids.

Haptens or antigens with amino groups or nitro groups reducible to amino groups can be converted to diazonium salts and reacted with proteins at alkaline pH, for aromatic amines. Haptens or antigens with aliphatic amines can be conjugated to proteins by various methods, including reaction with carbodiimides, reaction with the homobifunctional reagent tolylene-2,4-diisocyanate, or reaction with maleimide compounds. Aliphatic amines can also be converted to aromatic amines by reaction with p-nitrobenzoylchloride and subsequent reduction to a p-aminobenzoylamide, which can then be coupled to proteins after diazotization. Also, bifunctional esters such as dimethylpimelimidate, dimethyladipimidate, or dimethylsuberimidate, can be used to couple amino group-containing haptens or antigens to proteins, including enzymes.

Thiol-containing haptens or antigens can be conjugated to proteins with maleimides, such as 4-(N-maleimidomethyl)-cyclohexane-1-carboxylic acid N-hydroxysuccinimide ester.

For haptens or antigens with hydroxyl groups, an alcohol function can be converted to the hemisuccinate, which introduces a carboxyl group available for conjugation. Alternatively, the bifunctional reagent sebacoyldichloride converts an alcohol to an acid chloride, which then reacts with enzymes.

Phenols can be activated with diazotized p-aminobenzoic acid which introduces a carboxyl group, and can then be reacted with the protein by the mixed anhydride reaction. Sugars can be activated by forming a p-nitrophenyl glycoside, followed by reduction of the nitro group to an amino group and conjugation by diazotization. Other methods include the cleavage of vicinal glycol of sugars to aldehydes by reaction with periodate, followed by coupling to amines by reductive alkylation with sodium borohydride. Alternatively, hydroxyl containing haptens or antigens can be conjugated after conversion to chlorocarbonates by reaction with phosgene.

For haptens or antigens with aldehyde or ketone groups, carboxyl groups can be introduced through the formation of o-carboxymethyloximes. Ketone groups can also be derivatized with p-hydrazinobenzoic acid to produce carboxyl groups. Haptens or antigens containing aldehydes can be directly conjugated through the formation of Schiff bases that are stabilized by reaction with a reducing agent such as sodium borohydride. The foregoing is only a summary, and other coupling methods are well known in the art and may be useful for specific antigens or haptens.

Devices Suitable for Enzyme Immunochromatography

Several variations of immunochromatographic devices according to the present invention are suitable for enzyme immunochromatography. In one such device, the enzyme-labeled specific binding partner to the analyte is added to the test sample and allowed to migrate through the chromatographic medium. In the device, an insert contains, in resolubilizable form, a substrate for the enzyme label.

This device comprises:

(1) a base panel including:
  (a) a first opposable component including:
    (i) a planar chromatographic medium having a first end, a second end, and first and second surfaces and having a specific binding partner to the analyte immobilized thereon in a detection zone as described above;
    (ii) a conductor in operable contact with the first end of the chromatographic medium; and
    (iii) a substantially fluid-impermeable barrier adjacent to the first surface of the chromatographic medium and having an aperture therethrough for application of liquid to the chromatographic medium, the aperture being substantially smaller in area than the barrier;
  (b) a second opposable component including a first absorber, the first and second opposable components being configured so that when they are brought into opposition the first absorber is brought into operable contact with a portion of the chromatographic medium between the barrier and the second end of the chromatographic medium; and
  (c) a receptacle for insertion of a protrusion of an insert for holding the insert stable against relative motion of the surfaces of the insert and of the first and second opposable component;

(2) an insert including:
  (a) an applicator containing, in resolubilizable form, a substrate for an enzyme label that is bound to a specific binding partner to the analyte, the enzyme label producing an insoluble detectable product by catalysis of a reaction involving the substrate;
  (b) a second absorber;
  (c) a third absorber; and
  (d) a protrusion for insertion into the receptacle of the base panel.

The insert is configured so that when the protrusion is inserted into the receptacle of the base panel, the applicator is in operable contact with the aperture to apply the contents of the aperture to the chromatographic medium through the aperture, the second absorber is in operable contact with a portion of the chromatographic medium between the barrier and the first end of the chromatographic medium, and the third absorber is in operable contact with a portion of the chromatographic medium between the barrier and the second end of the chromatographic medium.

Figure 16A:
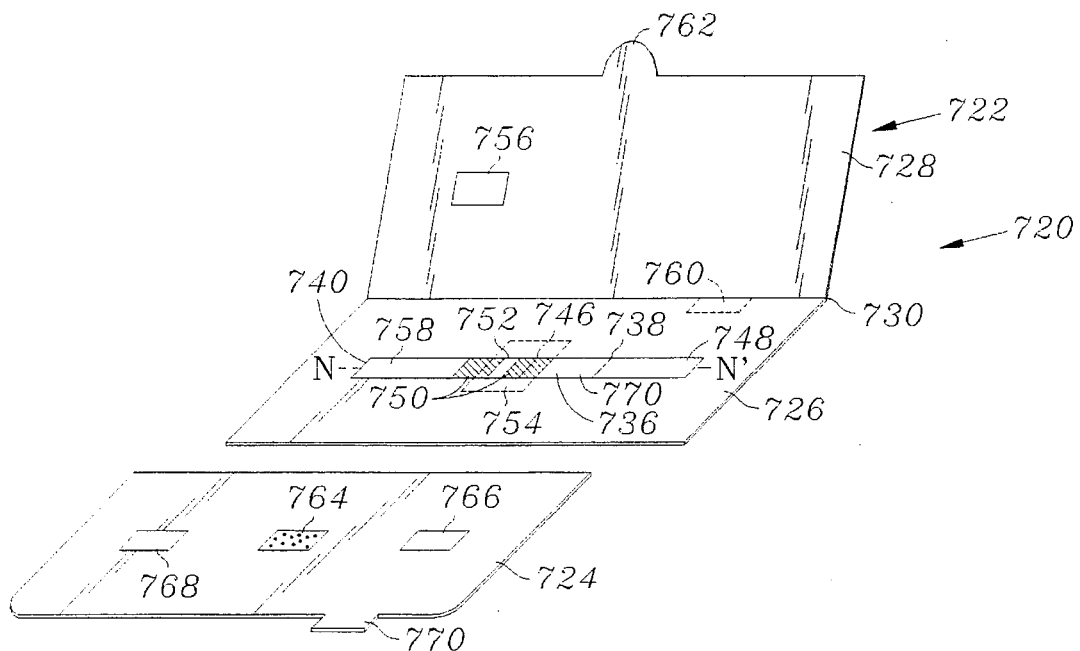
FIG. 16A is a drawing of an assay device according to the present invention employing a two-component base panel and an insert and suitable for performing an enzyme immunoassay using an enzyme-labeled antibody, with a substrate that forms an insoluble product.
Figure 16B:
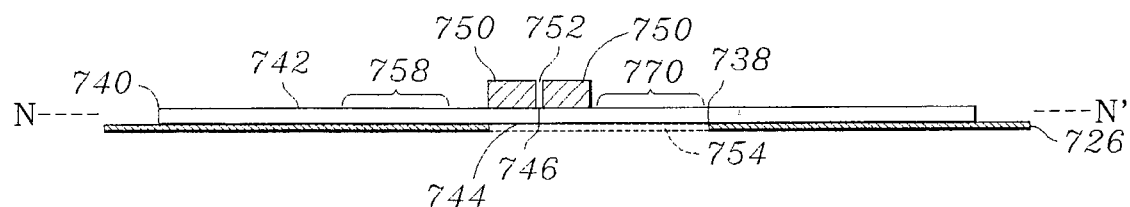
FIG. 16B is a cross-section along line N–N' of the first component of the base panel of the assay device of FIG. 15A, showing the detail of the chromatographic medium, elements in direct or indirect contact with the chromatographic medium, the barrier, and the aperture.

This device is depicted in FIGS. 16A and 16B. FIG. 16A shows the arrangement of the two components of the base panel together with the insert, and FIG. 16B shows a cross-section along line N–N' of the first component of the base panel, showing the detail of the chromatographic medium, elements in direct or indirect contact with the chromatographic medium, the barrier, and the aperture. The assay device 720 comprises a base panel 722 and an insert 724. The base panel 722 includes a first opposable component 726 and a second opposable component 728, joined by a hinge 730. The first opposable component 726 has a chromatographic medium 736 with first and second ends 738 and 740 and first and second surfaces 742 and 744. The chromatographic medium 736 includes a detection zone 746 on which is immobilized a specific binding partner for the analyte. The first opposable component 726 also includes a conductor 748 in operable contact with the first end 738 of the chromatographic medium 736. The first opposable component 726 also includes a substantially fluid-impermeable barrier 750 adjacent to the first surface 742 of the chromatographic medium 736. The barrier 750 has an aperture 752 therethrough for application of liquid to the chromatographic medium 736. The aperture 752 is substantially smaller in area than the barrier 750. The first opposable component 726 also includes a window 754 to allow viewing of the chromatographic medium.

The second opposable component 728 includes a first absorber 756. The first and second opposable components 706 and 708 are configured so that when they are brought into opposition the first absorber 756 is brought into operable contact with a first portion 758 of the chromatographic medium 736 between the barrier 750 and the second end 740 of the chromatographic medium 736. The base panel 702 further includes a receptacle 760 to hold the insert 724. The first and second opposable components 726 and 728 can be held together by an engager 762 such as a resealable label, a Velcro™ closure, or other reversibly engageable closure.

The insert 724 includes an applicator 764 containing, in resolubilizable form, a substrate for an enzyme label that is bound to a specific binding partner to the analyte. The insert 724 also includes a second absorber 766 and a third absorber 768 as well as a protrusion 770 for insertion into the receptacle 760 of the base panel 722. The insert 724 is configured so that when the protrusion 770 is inserted into the receptacle 760 of the base panel 722, the applicator 764 is in operable contact with the aperture 752 to apply the contents of the applicator 764 to the chromatographic medium 736 through the aperture. The second absorber 766 is in operable contact with a second portion 770 of the chromatographic medium 736 between the barrier 750 and the first end 738 of the chromatographic medium 736. The third absorber 768 is in operable contact with the first portion 758 of the chromatographic medium 736 between the barrier 750 and the second end 740 of the chromatographic medium 736.

In use, an enzyme-labeled specific binding partner to the analyte is added to an aqueous test sample. The solution containing the sample and the enzyme label is added to the conductor 748. The first and second opposable components 726 and 728 of the base panel 722 are then brought into opposition. The first absorber 756 is brought into operable contact with the portion 758 of the chromatographic medium 736 between the barrier 750 and the second end 740 of the chromatographic medium 736. The sample-label solution is then allowed to enter the chromatographic medium 736 and to flow through at least a portion of the chromatographic medium 736 including the detection zone 746. An aqueous liquid is added to the applicator 764 of the insert 724 to resolubilize the substrate on the applicator 764. This can be done either before or after applying the sample-label solution to the conductor 748. Then the protrusion 770 of the insert 724 is inserted into the receptacle 760 of the base panel 722. The insert 724 is positioned so that the applicator 764 is in contact with the aperture 752 in the barrier 750. The contents of the applicator 764 are applied to the chromatographic medium 736 through the aperture 752. The second and third absorbers 766 and 768 are placed in contact with portions 772 and 758 of the chromatographic medium 736 to withdraw fluid from the chromatographic medium 736. The resolubilized substrate is then allowed to flow through at least the portion of the chromatographic medium 736 including the detection zone 746. The enzyme of the enzyme label catalyzes a reaction involving the substrate and depositing an insoluble product as the signal of the label. This allows detection of the labeled specific binding partner bound to the detection zone 746 to detect and/or determine the analyte.

Another version of an assay device according to the present invention suitable for enzyme immunochromatography does not require pre-mixing of a sample-enzyme solution for application to the device. In this device, the first opposable component of the base panel contains a specific binding partner to the analyte labeled with an enzyme.

This device comprises:

(1) a base panel including:
  (a) a first opposable component including:
    (i) a planar chromatographic medium having a first end, a second end, and first and second surfaces, and having a specific binding partner to the analyte immobilized thereon in a detection zone as described above;
    (ii) a conjugate zone containing a specific binding partner to the analyte labeled with an enzyme in resolubilizable form, the conjugate zone being in operable contact with the first end of the chromatographic medium;
    (iii) a conductor in operable contact with the conjugate zone, the conjugate zone bridging the first end of the chromatographic medium and the conductor; and
    (iv) a substantially fluid-impermeable barrier adjacent to the first surface of the chromatographic medium and having an aperture therethrough for application of liquid to the chromatographic medium, the aperture being substantially smaller in area than the barrier as described above;
  (b) a second opposable component including:
    (i) a first receptacle for a swab containing a test sample;
    (ii) a well for addition of at least one extraction reagent to the swab; and
    (iii) a first absorber separated from the first receptacle and the well; and
  (c) a second receptacle for holding an insert stable against relative motion of the surfaces of the insert and the first and second opposable component;

(2) an insert including:
  (a) an applicator containing, in resolubilizable form, a substrate for an enzyme label bound to a specific binding partner to the analyte, the enzyme label producing an insoluble detectable product by catalysis of a reaction involving the substrate;
  (b) a second absorber;
  (c) a third absorber; and
  (d) a protrusion for insertion into the slot of the second receptacle of the base panel.

The first and second opposable components are configured so that when they are brought into opposition, the first absorber is brought into contact with a portion of the chromatographic medium between the barrier and the second end of the chromatographic medium and the first receptacle is brought into contact with the conductor.

The insert is configured such that when the protrusion is inserted into the second receptacle of the base panel, the applicator is in operable contact with the aperture to apply the contents of the applicator to the chromatographic medium through the aperture. The second absorber is in operable contact with a portion of the chromatographic medium between the barrier and the first end of the chromatographic medium. The third absorber is in operable contact with a portion of the chromatographic medium between the barrier and the second end of the chromatographic medium.

Figure 17A:
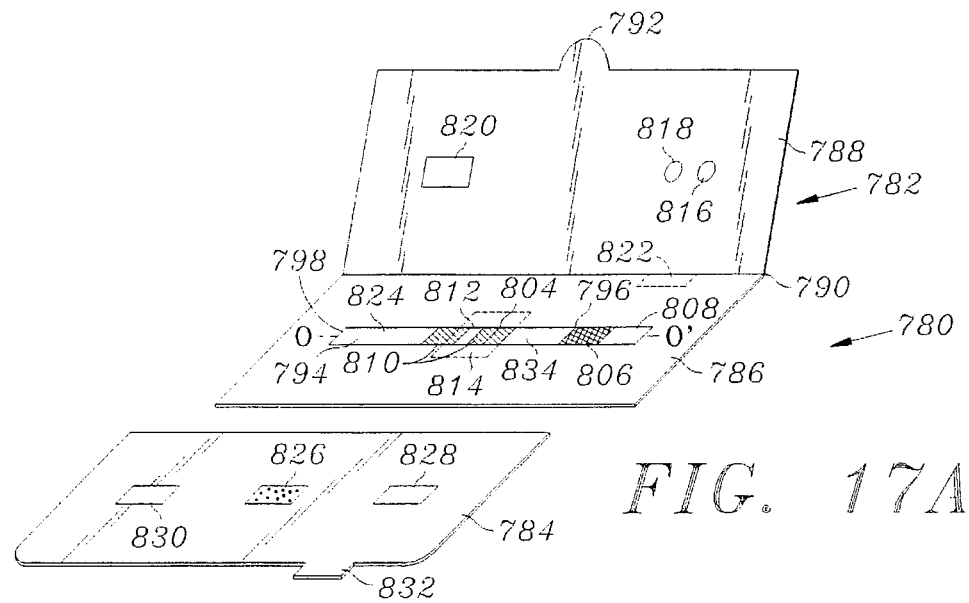
FIG. 17A is a drawing of an assay device according to the present invention employing a two-component base panel and an insert that is suitable for enzyme immunochromatography and incorporating a specific binding partner to the analyte labeled with an enzyme on the first component of the base panel of the device.
Figure 17B:
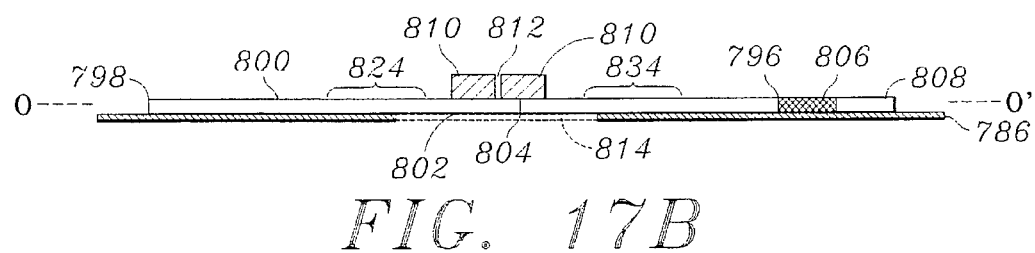
FIG. 17B is a cross-section along line 0–0' of the first component of the base panel of the assay device of FIG. 16A, showing the detail of the chromatographic medium, elements in direct or indirect contact with the chromatographic medium, the barrier, and the aperture.

This device is depicted in FIGS. 17A and 17B. FIG. 17A shows the arrangement of the two components of the base panel together with the insert, and FIG. 17B shows a cross-section along line O–O' of the first component of the base panel, showing the detail of the chromatographic medium, elements in direct or indirect contact with the chromatographic medium, the barrier, and the aperture. The assay device 780 has a base panel 782 and an insert 784. The base panel 782 includes a first opposable component 786 and a second opposable component 788 joined by a hinge 790. The first and second opposable components 786 and 788 can be held together by an engager 792 such as a resealable label, a Velcro™ closure, or other reversibly engageable closure.

The first opposable component 786 has a chromatographic medium 794 thereon. The chromatographic medium 794 has first and second ends 796 and 798, a first surface 800, and a second surface 802. The chromatographic medium 794 also has a detection zone 804 thereon, with a specific binding partner to the analyte immobilized thereto. The first opposable component also includes a conjugate zone 806 containing a specific binding partner to the analyte labeled with an enzyme in resolubilizable form. The conjugate zone 806 is in operable contact with the first end 796 of the chromatographic medium 794. The first opposable component 786 further includes a conductor 808 in operable contact with the conjugate zone 806. The conjugate zone 806 bridges the first end 796 of the chromatographic medium 794 and the conductor 808. The first opposable component 786 further includes a substantially fluid-impermeable barrier 810 adjacent to the first surface 800 of the chromatographic medium 794. The barrier 810 has an aperture 812 therethrough for application of liquid to the chromatographic medium 794. The aperture 812 is substantially smaller in area than the barrier 810. The first opposable component 786 further includes a window 814 for viewing of the chromatographic medium 794.

The second opposable component 788 includes a first receptacle 816 for a swab containing a test sample, a well 818 for addition of at least one extraction reagent to the swab, and a first absorber 820 separated from the first receptacle 816 and the well 818.

The base panel 782 also includes a second receptacle 822 for holding the insert 784 stable against relative motion of the first and second opposable components 786 and 788 and the insert 784.

The first and second opposable components 786 and 788 are configured so that when they are brought into opposition, the first absorber 820 is brought into contact with a portion 824 of the chromatographic medium 794 between the barrier 810 and the second end 798 of the chromatographic medium 794. The first receptacle 816, for holding a swab, is brought into contact with the conductor 808.

The insert 784 includes an applicator 826 containing, in resolubilizable form, a substrate for an enzyme label that is bound to a specific binding partner to the analyte. The enzyme label produces an insoluble detectable product by catalysis of a reaction involving the substrate.

The insert 784 also contains a second absorber 828, a third absorber 830, and a protrusion 832 for insertion into the second receptacle 822 of the base panel 782. The insert 784 is configured such that when the protrusion 832 is inserted into the second receptacle 822 of the base panel 782, the applicator 826 is in operable contact with the aperture 812 in the barrier 810. The contents of the applicator 826 are applied to the chromatographic medium 794 through the aperture 812. The second absorber 828 is in operable contact with a portion 834 of the chromatographic medium 794 between the barrier 792 and the first end 796 of the chromatographic medium 794. The third absorber 830 is in operable contact with the portion 824 of the chromatographic medium 794 between the barrier 812 and the second end 798 of the chromatographic medium 794.

In use, a swab containing a test sample is inserted into the first receptacle 816 of the second opposable component 788 of the base panel 782. At least one extraction reagent is applied to the well 818 to extract analyte from the swab. The first and second opposable components 786 and 788 are brought into opposition so that the swab in the first receptacle 816 is in contact with the conductor 808 to apply the extracted analyte to the conductor 808. The first absorber 820 is in contact with the portion 824 of the chromatographic medium between the barrier 810 and the second end 798 of the chromatographic medium 794. The extracted sample is then allowed to flow through the conjugate zone 806 to resolubilize the labeled specific binding partner in the conjugate zone 806, and the extracted sample and the resolubilized labeled specific binding partner are allowed to enter the chromatographic medium 794 and to flow through at least a portion of the chromatographic medium 794 including the detection zone 804.

An aqueous liquid is added to the applicator 826 of the insert 784 to resolubilize the substrate. This aqueous liquid can be added either before or after the first and second opposable components 786 and 788 are brought into opposition.

Then, the protrusion 832 of the insert 784 is inserted into the second receptacle 822 of the base panel 782. The insert 784 is positioned so that the applicator 826 is in contact with the aperture 812 in the barrier 810 to apply the contents of the applicator 826 to the chromatographic medium 794 through the aperture 810. The second and third absorbers 828 and 830 are in contact with the portions 834 and 824 of the chromatographic medium 794 to withdraw fluid from the chromatographic medium 794. The resolubilized substrate is then allowed to flow through at least the portion of the chromatographic medium 794 including the detection zone 804 so that a detectable signal is formed, which is used to detect the analyte.

The invention is illustrated by the following Examples. The Examples are for illustrative purposes only and are not to be construed as limiting the scope of the invention in any manner.

EXAMPLES

Example 1

Example Showing Lack of Reaction with Sample Negative for Giardia

An experiment was performed to show that a sample negative for the fecal parasite Giardia would not react with a test strip containing anti-Giardia antibody lines assembled in an assay device according to the present invention; i.e. a negative control. In this device, 5 μm nitrocellulose was used for the chromatographic medium (test strip) and two lines of anti-Giardia antibody (obtained from Cellabs, Australia) were positioned on the strip as indicated. The length of the strip was 0.75 inch. The width of the strip was 0.25 inch. At each end of the strip, a length of absorbent (Ahlstrom 270, Ahlstrom Filtration, Holly Springs, Pa.) of 0.375 inch was placed. The exposed surface of the strip was covered with an impermeable barrier leaving an approximately 1/16 inch gap or slit at a position midway between the two antibody lines for the first barrier 252 and the aperture 254 in the first barrier 252.

The test strip and the impermeable label were placed in a simplified version of a two-component assay device as shown in FIGS. 3A and 3B, above, lacking the gasket 82 and absorbers 98 and 100. On top of the chromatographic medium (test strip) 84 and barrier 102, a conjugate pad of anti-Giardia antibody labeled with colloidal gold dye (40 nm, EY Laboratories, San Mateo, Calif.) with a pink-red color (applicator) 106 was placed. In the right-hand panel of the device a specimen pad (sample preparation zone) 110 was placed. The specimen pad was made of polyester material.

A fecal specimen, negative for Giardia, was added to the specimen pad and the housing closed. Faint pink liquid was immediately observed through the window to spread in both directions from the central application band. No result lines developed over an observation period of thirty minutes. Therefore, a negative specimen gave a negative result.

Example 2

Experiment Showing Positive Detection of Giardia

A simplified assay device was prepared. This device was basically similar to the device shown in FIG. 7A and 7B, above, with the following changes: (1) the distribution membrane 285 was omitted; (2) on the second component, a sample preparation zone (specimen pad) replaced the receptacle 288 for the swab 286; (3) the engagers (locks) 268 and 269, gasket 270, and the opening 271 to accommodate the narrow end of the swab were omitted; and (4) both 277 and 278 were lines of anti-Giardia antibody instead of 278 being a control zone, i.e., a line of analyte or analyte analogue. In this device, the aperture 282 in the first barrier 281 was approximately 1/16 inch wide.

Figure 18:
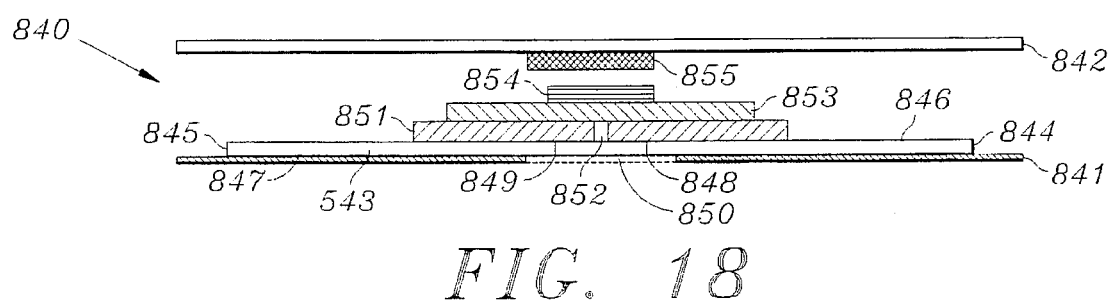
FIG. 18 is a cross-section of a simplified version of the device shown in FIGS. 7A and 7B and used to perform a test for the detection of the parasite Giardia in Example 2, below.

This device is shown in a cross-sectional view in FIG. 18. The device 840 has first and second opposable components 841 and 842. The first opposable component 841 has a chromatographic medium 843, with a first end 844 and a second end 845 and first and second surfaces 846 and 847. The chromatographic medium 843 has first and second detection zones 848 and 849 thereon. The first opposable component 841 has a window 850 for viewing of the chromatographic medium 843. Adjacent to the first surface 846 of the chromatographic medium 843 is a first barrier 851 with an aperture 852. The first opposable component further includes an applicator 853 adjacent to the first barrier 852, and a second barrier 854 adjacent to the central portion of the applicator 853. The second opposable component 842 has a specimen pad 855.

A fecal specimen positive for Giardia was added to the specimen pad 855 on the second opposable component 842 of the device 840 and the device 840 was closed to apply the specimen to the chromatographic medium 843. Two result lines were clearly visible through the window within one minute. On unfolding the device 840 at the conclusion of the test, the applicator 853 (the conjugate pad) was observed to have been completely cleared of pink conjugate. In other words, the assay device had effected complete mobilization and clearance of the conjugate from the pad.

Example 3

Assay Device for Streptococcus A

An assay device for Streptococcus A was constructed according to the present invention. This assay device is a simplified version of the assay device shown in FIGS. 8A and 8B, lacking the gasket 297 and the opening 298. The first opposable component 291 of the assay device 290 included a chromatographic medium 299 of nitrocellulose with a capture antibody 304 as the detection zone and a control zone 305. The capture antibody was anti-Streptococcus A antibody (Binax, Portland, Me.). The control line was anti-rabbit IgG (Binax). The chromatographic medium 299 was backed with a clear plastic backing 315 to permit viewing of the chromatographic medium. At one end of the chromatographic medium 299 an absorbent 306 was positioned. The chromatographic medium 299 was covered with a first barrier membrane 307 containing a slit approximately 1/16 inch wide that constituted the first aperture 308. Placed adjacent to the first barrier membrane 307 was a conductive membrane that served as the distribution membrane 309, and placed adjacent to the conductive membrane 309 was a second barrier membrane 310, positioned such that flow could proceed around the ends of the second barrier membrane 310 to the conductive membrane 309. Adjacent to the second barrier membrane 310 was a conjugate pad that served as the applicator 311. The applicator 311 made contact at the ends with the conductive member 309. Covering the conjugate pad 311 was an impermeable paper strip that constituted the surface barrier 312. The impermeable paper strip 312 had a hole that was the second aperture 313 and through which sample passes, and two vents 314, which were positioned at opposing ends of the chromatographic medium 297.

The second component 292 of the assay device 290 had a receptacle 316 for inserting a swab, formed by an impermeable barrier covering the second component 292. The second component 292 also included a vacuum-formed well 317 for addition of an extraction reagent to the swab. The receptacle 316 and well 317 are below the surface of the second component 292, and the impermeable barrier is on the surface of the second component 292.

In use, *Streptococcus pyogenes* A organisms (ATCC 12385) were added to a dacron swab. The swab was inserted into the receptacle 316 on the second opposable component 292 of the assay device 290. When fully inserted, the head of the swab protruded slightly from the surface of the second component 292. Extraction solutions (four drops of Extraction Reagent A (2M sodium nitrite, 5% Tween 20), followed by four drops of Extraction Reagent B (0.25M acetic acid, 5% Tween 20) were added to the well 317 so that bacteria and bacterial extract were carried, by wicking, to the head of the swab. After a one minute extraction, the device was closed by folding the first component 291 over the second component 292, thereby bringing the head of the swab into contact with the surface barrier 312 and the second aperture 313. Extract migrated to the ends of the conjugate pad 311, around the second barrier membrane 310, and to the distribution membrane 309. The distribution membrane 309 served to mix the conjugate and extract before applying the mixture, via the first aperture 308 and the first barrier membrane 307, to the nitrocellulose chromatographic medium 299. The absence of an absorber on the control-line side of the first aperture 308 insured that the majority of the mixture passed the capture line of anti-Streptococcus A antibody, beyond which was the absorber 306. This device reliably detected $1 \times 10^4$ organisms in a total test time of less than three minutes. Negative specimens gave results that remained consistently negative for at least 20 minutes.

Example 4

Device for Enzyme Immunochromatography

A device constructed according to FIGS. 16A and 16B, above, was used to perform enzyme immunochromatography for the hormone human chorionic gonadotropin, frequently assayed as a pregnancy test. In this device, the applicator 764 did not contain a resolubilizable substrate for the enzyme label; rather, the substrate was added during the course of the test.

On the nitrocellulose chromatographic medium 736, a line of anti-hCG antibody was immobilized as the detection zone 746. A monoclonal anti-hCG antibody-alkaline phosphatase conjugate (Hybritech, San Diego, Calif.) was mixed with urine (either positive or negative for hCG) and added to the first end 738 of the chromatographic medium 736. Enzyme substrate (precipitating alkaline phosphatase substrate, Hybritech, San Diego, Calif.) that gave a precipitate on positive reaction was added to the applicator 764 on the insert 724, and after 5 minutes the insert 724 was placed in the device 720 and the device 720 closed. A blue band of precipitated substrate developed at the detection zone 746 when the test urine contained hCG.

ADVANTAGES OF THE INVENTION

Chromatographic assay devices according to the present invention provide an advantage in being constructed of opposable elements. The use of opposable elements provides great versatility, as it permits the performance of reactions in a number of different sequences. This is possible because the use of such opposable elements allows the delivery of reagents to precisely defined regions of a test strip or other reaction component. The use of opposable elements also provides optimum performance with minimum consumption of reagents by ensuring that reagents are not wasted by being sequestered in dead volumes of apparatus. Finally, the use of opposable components provides optimum containment of possibly contaminated blood samples, each as those containing HIV or hepatitis virus.

Additionally, chromatographic assay devices according to the present invention allow the rapid and accurate detection of clinically important analytes, such as Streptococcus A and B antigen, hemoglobin for the determination of fecal occult blood, and antibody to *Helicobacter pylori*, as well as clinically important haptens. The construction of the devices, and the resulting application of the sample and/or reagents to the chromatographic medium through a barrier in an aperture, allows more even application of the samples and reagents to the chromatographic medium, and reduces interference that might otherwise be introduced by particulates or colored samples. This construction also allows the use of filters to remove particulates before the sample reaches the chromatographic medium. The use of colloidal metal labels in a resolubilizable form provides extremely rapid kinetics of labeling. This further aids in the separation of contaminants and improves the performance of the assay.

Assay devices according to the present invention can also be used for sequential immunochromatography or enzyme immunochromatography. In these applications, they present the advantages of lower background and higher sensitivity. Similarly, assay devices according to the present invention are suitable for the performance of amplified immunoassays using silver amplification to enhance a gold label.

Additionally, assay devices according to the present invention are suitable for assay of hydrophobic analytes such as lipopolysaccharides by direct absorption of the analyte to the chromatographic medium of the assay device.

Extraction of biological samples such as blood, sputum, or feces can be performed directly in the devices, reducing the quantity of contaminated material that must be disposed and reducing the likelihood of accidental infection of physicians, technicians, or the public by such contaminated material. Test methods using devices according to the present invention have a wide dynamic range and are substantially free from false negatives that may occur in other test methods at high concentrations of analyte.

Although the present invention has been described with considerable detail, with reference to certain preferred versions thereof, other versions and embodiments are possible. These versions include other arrangements of two- or three-component devices that operate by the basic principles described herein and use controlled application of at least one reagent through an aperture in a barrier. These versions include assay devices adapted for competitive immunoassays as well as sandwich immunoassays, in various arrangements. Therefore, the scope of the invention is determined by the following claims.

I claim:

1. A chromatographic assay device for detection and/or determination of an analyte in a test sample comprising:
   (a) a first opposable component including:
      (i) a chromatographic medium having a first end, a second end, and first and second surfaces, and having a specific binding partner for the analyte immobilized thereon in a detection zone between the first and second ends of the chromatographic medium;
      (ii) at least one absorber in operable contact with at least one of the first and second ends of the chromatographic medium; and
      (iii) a substantially fluid-impermeable barrier layered on top of the first surface of the chromatographic medium and having an aperture for application of liquid to the chromatographic medium, the barrier at least partially blocking application of liquid to the chromatographic medium; and
   (b) a second opposable component containing at least one reactant for applying the at least one reactant directly or indirectly to the chromatographic medium through the aperture; wherein the first and second opposable components are configured so that bringing the first and second opposable components into opposition results in the second opposable component applying the at least one reactant directly or indirectly to the chromatographic medium through the aperture.

2. The assay device of claim 1 wherein the first and second opposable components can be placed in opposition so that pressure facilitates application of the at least one reactant to the chromatographic medium through the aperture.

3. A chromatographic assay device for detection and/or determination of an analyte in a test sample comprising:
   (a) a first opposable component including:
      (i) a first opposable component including a chromatographic medium having a first end, a second end, and first and second surfaces, and having a specific binding partner for the analyte immobilized thereon in a detection zone between the first and second ends of the chromatographic medium;
      (ii) at least one absorber in operable contact with at least one of the first and second ends of the chromatographic medium;
      (iii) a substantially fluid-impermeable barrier layered on top of the first surface of the chromatographic medium and having an aperture for application of liquid to the chromatographic medium, the barrier at least partially blocking application of liquid to the chromatographic medium; and
      (iv) an applicator layered on top of the barrier, the applicator containing a labeled specific binding partner to the analyte in a form that can be resolubilized by the addition of an aqueous liquid to the applicator, the applicator being positioned such that the barrier is located between the applicator and the chromatographic medium and such that an aqueous liquid applied to the applicator is drawn through the aperture after resolubilizing the labeled specific binding partner and then is drawn through the chromatographic medium by the at least one absorber so that the analyte and the labeled specific binding partner can form a ternary complex at the detection zone on the chromatographic medium; and
   (b) a second opposable component including a sample preparation zone; wherein the first and second opposable components are configured so that bringing the first and second opposable components into opposition results in the sample preparation zone being in contact with the applicator so that sample in the sample preparation zone is applied to the applicator for resolubilization of the resolubilizable labeled specific binding partner and chromatography through the chromatographic medium.

4. The assay device of claim 3 comprising at least two absorbers, one in operable contact with the first end of the chromatographic medium and one in operable contact with the second end of the chromatographic medium, wherein the detection zone is substantially smaller than the area of the chromatographic medium, and wherein the chromatographic medium further includes a control zone of analyte or analogue thereof immobilized thereon in an area substantially smaller than the area of the chromatographic medium and not overlapping with the detection zone, the control and detection zones positioned with respect to the aperture and the absorber such that the detection zone is between the aperture and one of the absorbers and the control zone is between the aperture and the other absorber.

5. The assay device of claim 3 wherein the label of the labeled specific binding partner is a visually detectable label.

6. The assay device of claim 3 wherein the sample preparation zone contains at least one reagent for treatment of the sample distinct from the labeled specific binding partner for the analyte.

7. A method for the detection and/or determination of an analyte in an aqueous test sample comprising:

(a) applying the sample to the sample preparation zone of the assay device of claim 6;

(b) incubating the sample in the sample preparation zone so that the at least one reagent for treatment of the sample can react with the sample to produce a treated sample;

(c) bringing the first and second opposable components into opposition so that the treated sample is transferred from the sample preparation zone to the applicator;

(d) allowing the treated sample transferred to the applicator to resolubilize the labeled specific binding partner in the applicator to form a solution in the applicator containing the transferred treated sample and the resolubilized labeled specific binding partner;

(e) allowing the solution containing the treated sample and the resolubilized labeled specific binding partner to enter the chromatographic medium through the aperture in the barrier and then to flow through at least the portion of the chromatographic medium including the detection zone; and (f) detecting and/or determining the analyte in the test sample by observing and/or measuring the labeled specific binding partner in the detection zone.

8. A method for the detection and/or determination of an analyte in an aqueous test sample comprising:

(a) applying the sample to the sample preparation zone of the assay device of claim 3;

(b) bringing the first and second opposable components into opposition so that the sample is transferred from the sample preparation zone to the applicator;

(c) allowing the sample transferred to the applicator to resolubilize the labeled specific binding partner in the applicator to form a solution in the applicator containing the transferred sample and the resolubilized labeled specific binding partner;

(d) allowing the solution containing the sample and the labeled specific binding partner to enter the chromatographic medium through the aperture and the barrier and then to flow through at least the portion of the chromatographic medium including the detection zone; and (e) detecting and/or determining the analyte in the test sample by observing and/or measuring the labeled specific binding partner bound to the detection zone.

9. A chromatographic assay device for detection and/or determination of an analyte in a test sample comprising:

(a) a first opposable component including:

(i) a chromatographic medium having a first end, a second end, and first and second surfaces, and having a specific binding partner to the analyte immobilized thereon in a detection zone between the first and second ends of the chromatographic medium;

(ii) at least one absorber in operable contact with at least one of the first and second ends of the chromatographic medium; and (iii) a substantially fluid-impermeable barrier layered on top of the first surface of the chromatographic medium and having an aperture for application of liquid to the chromatographic medium, the barrier at least partially blocking application of liquid to the chromatographic medium; and (b) a second opposable component including an applicator for application of a sample thereto, the applicator containing a labeled specific binding partner to the analyte in a form that can be resolubilized by the addition of an aqueous liquid to the applicator; wherein the first and second opposable components are configured so that bringing the first and second opposable components into opposition results in the applicator being in operable contact with the barrier so that the sample and the resolubilized labeled specific binding partner in the applicator are applied through the aperture in the barrier to the chromatographic medium for chromatography through the chromatographic medium.

10. The assay device of claim 9 comprising at least two absorbers, one in operable contact with the first end of the chromatographic medium and one in operable contact with the second end of the chromatographic medium, wherein the detection zone is substantially smaller than the area of the chromatographic medium, and wherein the chromatographic medium further includes a control zone of analyte or analogue thereof immobilized thereon in an area substantially smaller than the area of the chromatographic medium and not overlapping with the detection zone, the control and detection zones positioned with respect to the aperture and the absorber such that the detection zone is between the aperture and one of the absorbers and the control zone is between the aperture and the other absorber.

11. The assay device of claim 9 wherein the label of the labeled specific binding partner is a visually detectable label.

12. The assay device of claim 9 wherein the applicator contains at least one reagent for treatment of the sample distinct from the labeled specific binding partner for the analyte.

13. The assay device of claim 9 wherein the first and second opposable components can be placed in opposition so that pressure facilitates application of the sample and the resolubilized detection reagent to the chromatographic medium through the aperture.

14. A method for the detection and/or determination of an analyte in an aqueous test sample comprising the steps of:

(a) applying the sample to the applicator of the assay device of claim 9;

(b) allowing the sample to resolubilize the labeled specific binding partner in the applicator to form a solution in the applicator containing the sample and the resolubilized labeled specific binding partner;

(c) bringing the first and second opposable components into opposition so that the solution containing the sample and the resolubilized labeled specific binding partner is applied to the chromatographic medium through the aperture in the barrier;

(d) allowing the solution containing the sample and the labeled specific binding partner to flow through at least a portion of the chromatographic medium including the detection zone; and (e) detecting and/or determining the analyte in the test sample by observing and/or measuring the labeled specific binding partner bound at the detection zone.

15. An assay device for detection and/or determination of an analyte in a test sample comprising:
(a) a first opposable component including:
  (i) a chromatographic medium having a first end, a second end, and first and second surfaces, and having a specific binding partner to the analyte immobilized thereon in a detection zone between the first and second ends of the chromatographic medium;
  (ii) at least one absorber in operable contact with at least one of the first and second ends of the chromatographic medium;
  (iii) a substantially fluid-impermeable barrier layered on top of the first surface of the chromatographic medium and having an aperture for application of liquid to the chromatographic medium, the barrier at least partially blocking application of liquid to the chromatographic medium; and
  (iv) a filter for removing particulates layered on top of the barrier; the chromatographic medium, the barrier, and the filter being positioned so that the barrier is located between the filter and the chromatographic medium in a fluid flow path transverse to the direction of flow along the chromatographic medium; and
(b) a second opposable component including an applicator for application of a sample thereto, the applicator containing a labeled specific binding partner to the analyte in a form that can be resolubilized by the addition of an aqueous liquid to the applicator; wherein the first and second opposable components are configured so that bringing the first and second opposable components into opposition results in the applicator being in operable contact with the filter so that the sample and the resolubilized labeled specific binding partner in the applicator are applied to the filter and then through the aperture in the barrier to the chromatographic medium for chromatography through the chromatographic medium.

16. The assay device of claim 15 comprising at least two absorbers, one in operable contact with the first end of the chromatographic medium and one in operable contact with the second end of the chromatographic medium, wherein the detection zone is substantially smaller than the area of the chromatographic medium, and wherein the chromatographic medium further includes a control zone of analyte or analogue thereof immobilized thereon in an area substantially smaller than the area of the chromatographic medium and not overlapping with the detection zone, the control and detection zones positioned with respect to the aperture and the absorber such that the detection zone is between the aperture and one of the absorbers and the control zone is between the aperture and the other absorber.

17. The assay device of claim 15 wherein the label of the labeled specific binding partner is a visually detectable label.

18. The assay device of claim 15 wherein the applicator contains at least one reagent for treatment of the sample distinct from the labeled specific binding partner for the analyte.

19. The assay device of claim 15 wherein the filter removes fecal matter.

20. The assay device of claim 15 wherein the first and second opposable components can be placed in opposition so that pressure facilitates application of the sample and the resolubilized labeled detection reagent to the chromatographic medium through the aperture.

21. A method for the detection and/or determination of an analyte in an aqueous test sample comprising the steps of:
(a) applying the sample to the applicator of the assay device of claim 15;
(b) allowing the sample to resolubilize the labeled specific binding partner in the applicator to form a solution in the applicator containing the sample and the resolubilized labeled specific binding partner;
(c) bringing the first and second opposable components into opposition so that the solution containing the sample and the resolubilized labeled specific binding partner is applied to the filter;
(d) allowing the solution containing the sample and the labeled specific binding partner to pass through the filter to form a filtered solution;
(e) allowing the filtered solution to enter the chromatographic medium through the aperture in the barrier and to flow through at least the portion of the chromatographic medium including the detection zone; and
(f) detecting and/or determining the analyte in the test sample by observing and/or measuring the labeled specific binding partner bound at the detection zone.

22. An assay device for detection and/or determination of an analyte in a test sample comprising:
(a) a first opposable component including:
  (i) a chromatographic medium having a first end, a second end, and first and second surfaces, and having a specific binding partner to the analyte immobilized thereon in a detection zone between the first and second ends of the chromatographic medium;
  (ii) at least one absorber in operable contact with at least one of the first and second ends of the chromatographic medium;
  (iii) a substantially fluid-impermeable barrier layered on top of the first surface of the chromatographic medium and having an aperture for application of liquid to the chromatographic medium, the barrier at least partially blocking application of liquid to the chromatographic medium;
  (iv) an applicator layered on top of the barrier, the applicator containing a labeled specific binding partner for the analyte in a form that can be resolubilized by the addition of an aqueous liquid to the applicator; and
  (v) a filter for removing particulates layered on top of the applicator, the chromatographic medium, the barrier, the applicator, and the filter being positioned so that the applicator is located between the filter and the chromatographic medium in a fluid flow path transverse to the direction of flow along the chromatographic medium; and
(b) a second opposable component including a sample preparation zone; where the first and second opposable components are configured so that bringing the first and second opposable components into opposition results in the sample preparation zone being in operable contact with the filter so that sample is applied to the filter, and a solution of filtered sample and labeled specific binding partner is then applied to the chromatographic medium through the aperture in the barrier.

23. The assay device of claim 22 comprising at least two absorbers, one in operable contact with the first end of the chromatographic medium and one in operable contact with the second end of the chromatographic medium, wherein the detection zone is substantially smaller than the area of the chromatographic medium, and wherein the chromatographic medium further includes a control zone of analyte or analogue thereof immobilized thereon in an area substantially smaller than the area of the chromatographic medium and not overlapping with the detection zone, the control and detection zones positioned with respect to the aperture and the absorber such that the detection zone is between the aperture and one of the absorbers and the control zone is between the aperture and the other absorber.

24. The assay device of claim 22 wherein the label of the labeled specific binding partner is a visually detectable label.

25. The assay device of claim 22 wherein the sample preparation zone contains at least one reagent for treatment of the sample distinct from the specific binding partner for the analyte.

26. A method for the detection and/or determination of an analyte in an aqueous test sample comprising the steps of:

(a) applying the sample to the sample preparation zone of the assay device of claim 25;

(b) incubating the sample in the sample preparation zone so that the at least one reagent for treatment of the sample can react with the sample forming a treated sample;

(c) bringing the first and second opposable components into opposition to transfer the treated sample from the sample preparation zone to the filter;

(d) allowing the treated sample transferred to the filter to pass through the filter producing a filtered treated sample;

(e) allowing the filtered treated sample to enter the applicator to resolubilize the labeled specific binding partner in the applicator, forming a solution in the applicator containing the filtered treated sample and the resolubilized labeled specific binding partner;

(f) allowing the solution containing the filtered treated sample and the resolubilized labeled specific binding partner to enter the chromatographic medium through the aperture in the barrier and to flow through at least the portion of the chromatographic medium including the detection zone; and (g) detecting and/or determining the analyte in the test sample by observing and/or measuring the labeled specific binding partner bound at the detection zone.

27. The assay device of claim 22 wherein the filter removes fecal matter.

28. The assay device of claim 22 wherein the first and second opposable components can be placed in opposition so that pressure facilitates application of the solution of filtered sample and labeled specific binding partner to the chromatographic medium through the aperture.

29. A method for the detection and/or determination of an analyte in an aqueous test sample comprising the steps of:

(a) applying the sample to the sample preparation zone of the assay device of claim 22;

(b) bringing the first and second opposable components into opposition so that the sample is transferred from the sample preparation zone to the filter;

(c) allowing the sample transferred to the filter to pass through the filter to produce a filtered sample;

(d) allowing the filtered sample to enter the applicator to resolubilize the labeled specific binding partner in the applicator forming a solution in the applicator containing the filtered sample and the resolubilized specific binding partner;

(e) allowing the solution containing the filtered sample and the resolubilized labeled specific binding partner to enter the chromatographic medium through the aperture in the barrier and to flow through at least the portion of the chromatographic medium including the detection zone; and (f) detecting and/or determining the analyte in the test sample by observing and/or measuring the labeled specific binding partner bound to the detection zone.

30. An assay device for detection and/or determination of an analyte in a test sample comprising:

(a) a first opposable component including:

(i) a chromatographic medium having a first end, a second end, and first and second surfaces, and having a specific binding partner to the analyte immobilized thereon in a detection zone between the first end and the second end of the chromatographic medium;

(ii) at least one absorber in operable contact with at least one of the first and second ends of the chromatographic medium;

(iii) a first substantially fluid-impermeable barrier layered on top of the first surface of the chromatographic medium and having an aperture for application of liquid to the chromatographic medium, the first barrier at least partially blocking application of liquid to the chromatographic medium;

(iv) an applicator layered on top of the first barrier, the applicator containing a labeled specific binding partner to the analyte in a form that can be resolubilized by the addition of an aqueous liquid to the applicator;

(v) a second substantially fluid-impermeable barrier layered on top of a first portion of the applicator centrally located on the applicator; and (vi) a distribution membrane layered on top of the second barrier and in contact with portions of the applicator not supporting the second barrier so that fluid can flow from the distribution membrane to the applicator around the second barrier; and (b) a second opposable component including a receptacle for a swab that can contain a test sample; wherein the first and second opposable components are configured so that bringing the first and second opposable components into opposition results in applying a sample to the distribution membrane and then to the chromatographic medium.

31. The assay device of claim 30 comprising at least two absorbers, one in operable contact with the first end of the chromatographic medium and one in operable contact with the second end of the chromatographic medium, wherein the detection zone is substantially smaller than the area of the chromatographic medium, and wherein the chromatographic medium further includes a control zone of analyte or analogue thereof immobilized thereon in an area substantially smaller than the area of the chromatographic medium and not overlapping with the detection zone, the control and detection zones positioned with respect to the aperture and the absorber such that the detection zone is between the aperture and one of the absorbers and the control zone is between the aperture and the other absorber.

32. The assay device of claim 30 wherein the label of the labeled specific binding partner is a visually detectable label.

33. The assay device of claim 30 wherein the first and second opposable components can be placed in opposition so that pressure facilitates application of the sample to the chromatographic medium through the aperture.

34. A method for the detection and/or determination of an analyte in an aqueous test sample comprising the steps of:

(a) placing a swab containing the test sample in the receptacle of the assay device of claim 30;

(b) bringing the first and second opposable components of the assay device into opposition so that the test sample is transferred from the swab to the distribution membrane;

(c) allowing the sample to enter the applicator to resolubilize the labeled specific binding partner in the applicator to form a solution in the applicator containing the sample and the resolubilized labeled specific binding partner;

(d) allowing the solution containing the sample and the labeled specific binding partner to enter the chromatographic medium and to flow through at least a portion of the chromatographic medium including the detection zone; and (e) detecting and/or determining the analyte in the test sample by observing and/or measuring the labeled specific binding partner bound at the detection zone.

35. An assay device for performing a competitive immunoassay for detection and/or determination of an analyte in a test sample, comprising:

(a) a chromatographic medium having a first end, a second end, and first and second surfaces, and having a secondary specific binding partner immobilized thereon in a detection zone between the first and second ends of the chromatographic medium, the secondary specific binding partner capable of binding a member of a specific binding pair that lacks affinity for the analyte;

(b) at least one absorber in operable contact with at least one of the first and second ends of the chromatographic medium;

(c) a substantially fluid-impermeable barrier layered on top of the first surface of the chromatographic medium, the barrier having at least one aperture for application of liquid to the chromatographic medium, the barrier at least partially blocking application of liquid to the chromatographic medium; and (d) an affinity membrane layered on top of the barrier, the affinity membrane containing a specific binding partner to the analyte immobilized thereto; the chromatographic medium, absorber, barrier, aperture, and affinity membrane being configured such a liquid applied to the affinity membrane is drawn through the chromatographic medium by the at least one absorber so that a labeled analyte analogue comprising analyte bound to a member of a specific binding pair lacking affinity for the analyte and bindable by the secondary specific binding partner, the analyte analog being labeled with a detectable label, binds at the detection zone on the chromatographic medium if analyte is present in the sample.

36. An assay device for performing a competitive immunoassay for detection and/or determination of an analyte in a test sample comprising:

(a) a first opposable component including:

(i) a chromatographic medium having a first end, a second end, and first and second surfaces, and having a secondary specific binding partner immobilized thereon in a detection zone between the first end and second end of the chromatographic medium, the secondary specific binding partner capable of binding a member of a specific binding pair that lacks affinity for the analyte, the secondary specific binding partner being an antibody specific for a species, class, or subclass of antibody that does not bind the analyte;

(ii) a first absorber in operable contact with the first end of the chromatographic medium;

(iii) a second absorber in operable contact with the second end of the chromatographic medium;

(iv) a substantially fluid-impermeable barrier layered on top of the first surface of the chromatographic medium and having an aperture therethrough for application of liquid to the chromatographic medium, the aperture being substantially smaller in area than the barrier so that liquid can enter the chormatographic medium only through the aperture; the chromatographic medium, absorbers, barrier and aperture being configured so that the detection zone is located between the aperture and the first end of the chromatographic medium; and (v) an affinity membrane layered on top of the barrier, the affinity membrane containing a specific binding partner to the analyte immobilized thereto; and (b) a second opposable component including an applicator, the applicator containing an analyte analogue in a form that can be resolubilized by the addition of an aqueous liquid to the applicator, the analyte analogue comprising analyte covalently bound to a member of a specific binding pair lacking affinity for the analyte and bindable by the secondary specific binding partner, the analyte analogue being labeled with a detectable label; wherein the first and second opposable components are configured so that bringing the first and second opposable components into opposition results in the applicator being in operable contact with the affinity membrane.

37. The assay device of claim 36 wherein the detectable label is a visually detectable label.

38. The assay device of claim 36 wherein the first and second opposable components can be placed in opposition so that pressure facilitates application of the liquid to the chromatographic medium through the aperture.

39. A method for the detection and/or determination of an analyte in an aqueous test sample comprising the steps of:

(a) applying the sample to the applicator of the assay device of claim 36;

(b) allowing the sample to resolubilize the labeled analyte analogue in the applicator to form a solution in the applicator containing the test sample and the resolubilized labeled analyte analog;

(c) bringing the first and second opposable components of the assay device into opposition so that the solution containing the test sample and the resolubilized labeled analyte analogue is transferred from the applicator to the affinity membrane;

(d) allowing the solution containing the test sample and the resolubilized analyte analogue to pass through the affinity membrane, and then into the chromatographic medium through the aperture in the barrier and to flow through at least a portion of the chromatographic medium including the detection zone; and (e) detecting and/or determining the analyte in the test sample by observing and/or measuring the labeled analyte analogue bound to the detection zone by performance of a competitive immunoassay, wherein the quantity of labeled analyte analogue bound is directly correlated with the concentration of analyte in the test sample.

40. An assay device for detection and/or determination of an analyte in a test sample comprising:

(a) a first opposable component including:

(i) a chromatographic medium having a first end and a second end and first and second surfaces, and having immobilized thereon in separate discrete and non-overlapping zones between the first and second ends of the chromatographic medium:

(A) a detection zone with immobilized specific binding partner to the analyte; and (B) a control zone of analyte or analogue thereof; the detection zone being located between a point removed from the ends of the chromatographic medium and the second end of the chromatographic medium and the control zone being located between a point removed from the ends of the chromatographic medium and the second end of the chromatographic medium;

(ii) an absorber in operable contact with the first end of the chromatographic medium;

(iii) a first substantially fluid-impermeable barrier layered on top of the first surface of the chromatographic medium and having a first application aperture substantially smaller than the area of the chromatographic medium and located at a point removed from the ends of the chromatographic medium, the first barrier at least partially blocking application of liquid to the chromatographic medium;

(iv) an applicator layered on top of the first barrier, the applicator containing a labeled specific binding partner to the analyte in a form that can be resolubilized by the addition of an aqueous liquid to the applicator, the applicator positioned to apply liquid to the chromatographic medium via the first application aperture; and (v) a second substantially fluid-impermeable barrier layered on top of the applicator and positioned to at least partially block application of liquid to the applicator and to allow application of liquid to the applicator through a second application aperture substantially smaller than the area of the chromatographic medium and located closer to the second end of the chromatographic medium then to the first end of the chromatographic medium; and (b) a second opposable component including a sample preparation zone; wherein the first and second opposable components are configured so that bringing the first and second opposable components into opposition results in the sample preparation zone being in contact with the second barrier so that the sample in the sample preparation zone is applied to the applicator through the second application aperture and traverses substantially the entire length of the applicator in order to apply the sample and the resolubilized labeled specific binding partner to the chromatographic medium through the first application aperture.

41. The assay device of claim 40 wherein the sample preparation zone contains at least one reagent for treatment of the sample.

42. A method for detection and/or determination of an analyte in a test sample comprising:

(a) applying the test sample to the sample preparation zone of the assay device of claim 41;

(b) incubating the sample in the sample preparation zone so the at least one reagent for treatment of the sample can react with the sample forming a treated sample;

(c) bringing the first and second opposable components into opposition so that the treated sample is transferred to the applicator through the second application aperture;

(d) allowing the treated sample transferred to the applicator to resolubilize the labeled specific binding partner in the applicator to form a solution containing the treated sample and the resolubilized labeled specific binding partner;

(e) allowing the solution containing the treated sample and the resolubilized labeled specific binding partner to enter the chromatographic medium and to flow through at least the portion of the chromatographic medium including the detection zone and the control zone; and (f) detecting and/or determining the analyte in the test sample by observing and/or measuring the labeled specific binding partner bound to the detection zone.

43. The assay device of claim 40 wherein the detectable label is a visually detectable label.

44. The assay device of claim 40 wherein the first and second opposable components can be placed in opposition so that pressure facilitates application of the sample to the chromatographic medium through the first and second apertures.

45. A method for detection and/or determination of an analyte in a test sample comprising:

(a) applying the test sample to the sample preparation zone of the assay device of claim 40;

(b) bringing the first and second opposable components into opposition so that the test sample is transferred to the applicator through the second application aperture;

(c) allowing the sample transferred to the applicator to resolubilize the labeled specific binding partner in the applicator to form a solution containing the sample and the resolubilized labeled specific binding partner;

(d) allowing the solution containing the sample and the resolubilized labeled specific binding partner to enter the chromatographic medium and to flow through at least the portion of the chromatographic medium including the detection zone and the control zone; and (e) detecting and/or determining the analyte in a test sample by observing and/or measuring the labeled specific binding partner bound at the detection zone.

46. An assay device for detection and/or determination of a hydrophobic analyte in a test sample comprising:

(a) a first opposable component including:

(i) a nylon chromatographic medium having a first end, a second end, and first and second surfaces, the chromatographic medium having an affinity for a hydrophobic analyte sufficient to immobilize the analyte from an aqueous solution containing the analyte on the chromatographic medium;

(ii) an applicator in operable contact with the first end of the chromatographic medium, the applicator containing a labeled specific binding partner to the analyte in a form that can be resolubilized by the addition of an aqueous liquid to the applicator;

(iii) an absorber in operable contact with the second end of the chromatographic medium; and (iv) a substantially fluid-impermeable barrier layered on top of the first surface of the chromatographic medium and having an aperture for application of liquid to the chromatographic medium, the barrier at least partially blocking application of liquid to the chromatographic medium; and (b) a second opposable component including a sample preparation zone; wherein the first and second opposable components are configured so that bringing the first and second opposable components into opposition results in the sample preparation zone being in contact with the barrier so that the sample in the sample preparation zone is applied to the chromatographic medium and so that analyte in a test sample is immobilized on the chromatographic medium in at least the vicinity of the aperture.

47. The assay device of claim 46 wherein the detectable label is a visually detectable label.

48. The assay device of claim 46 wherein the antigen is a lipopolysaccharide.

49. The assay device of claim 46 wherein the sample preparation zone contains at least one reagent for treatment of the analyte.

50. The assay device of claim 46 wherein the first and second opposable components can be placed in opposition so that pressure facilitates application of the sample to the chromatographic medium through the aperture.

51. An assay device for detection and/or determination of an analyte in a test sample comprising:
   (a) a first opposable component including:
      (i) a chromatographic medium having a first end, a second end, and first and second surfaces, and having a specific binding partner for the analyte immobilized thereon in a detection zone between the first and second ends of the chromatographic medium;
      (ii) a sample preparation zone in operable contact with the first end of the chromatographic medium;
      (iii) a first absorber in operable contact with the second end of the chromatographic medium; and
      (iv) a substantially fluid-impermeable barrier layered on top of the first surface of the chromatographic medium and having an aperture for application of liquid to the chromatographic medium, the barrier at least partially blocking application of liquid to the chromatographic medium; and
   (b) a second opposable component including:
      (i) an applicator containing a labeled specific binding partner to the analyte in a form that can be resolubilized by the addition of an aqueous liquid to the applicator, the applicator positioned such that when the first and second opposable components are brought into opposition, the applicator is in contact with the barrier so that the resolubilized labeled specific binding partner is applied through the aperture in the barrier to the chromatographic medium; and
      (ii) second and third absorbers positioned such that when the first and second opposable components are brought into opposition, the second absorber and third absorber are in operable contact with portions of the chromatographic medium so that the second and third absorbers remove fluid from the chromatographic medium.

52. The assay device of claim 51 wherein the label is a visually detectable label.

53. The assay device of claim 51 wherein the sample preparation zone contains at least one reagent for treatment of the sample.

54. A method for the detection and/or determination of an analyte in an aqueous test sample comprising the steps of:
   (a) applying the sample to the sample preparation zone of the assay device of claim 53;
   (b) incubating the sample in the sample preparation zone so that the at least one reagent for treatment of the sample can react with the sample to produce a treated sample;
   (c) allowing the treated sample to flow through at least the portion of the chromatographic medium including the detection zone;
   (d) adding an aqueous liquid to the applicator to resolubilize the labeled specific binding partner to the analyte;
   (e) bringing the first and second opposable components into opposition to apply the resolubilized labeled specific binding partner to the chromatographic medium through the aperture in the barrier and to bring the second and third absorbers into operable contact with the chromatographic medium to withdraw fluid therefrom;
   (f) allowing the resolubilized labeled specific binding partner to flow through at least the portion of the chromatographic medium including the detection zone to form a ternary complex including labeled specific binding partner at the detection zone if analyte is present in the test sample; and
   (g) detecting and/or determining the analyte in the test sample by observing and/or measuring the labeled specific binding partner bound at the detection zone.

55. The assay device of claim 51 wherein the chromatographic medium further includes a control zone of analyte or analogue thereof immobilized thereto in an area not overlapping with the detection zone, the detection zone being positioned between the aperture and the first end of the chromatographic medium and the control zone being positioned between the aperture and the second end of the chromatographic medium.

56. The assay device of claim 51 wherein the first and second opposable components can be placed in opposition so that pressure facilitates application of the resolubilized labeled specific binding partner to the chromatographic medium through the aperture.

57. A test kit for the detection and/or determination of an analyte in a test sample comprising, in separate containers:
   (a) the assay device of claim 51; and
   (b) an aqueous liquid for resolubilizing the labeled specific binding partner in the applicator.

58. A method for the detection and/or determination of an analyte in an aqueous test sample comprising:
   (a) applying the sample to the sample preparation zone of the assay device of claim 51;
   (b) allowing the sample to flow through at least the portion of the chromatographic medium including the detection zone;
   (c) adding an aqueous liquid to the applicator to resolubilize the labeled specific binding partner to the analyte;
   (d) bringing the first and second opposable components into opposition to apply the labeled specific binding partner to the chromatographic medium through the aperture in the barrier and to bring the second and third absorbers into operable contact with the chromatographic medium to withdraw fluid therefrom;
   (e) allowing the resolubilized labeled specific binding partner to flow through at least the portion of the chromatographic medium including the detection zone to form a ternary complex including labeled specific binding partner at the detection zone if analyte is present in the test sample; and
   (f) detecting and/or determining the analyte in the test sample by observing and/or measuring the labeled specific binding partner bound at the detection zone.

59. An assay device for detection and/or determination of an analyte in a test sample comprising:
   (a) a first opposable component including:
      (i) a chromatographic medium having a first end, a second end, and first and second surfaces, and having a specific binding partner to the analyte immobilized thereon in a detection zone between the first end and the second end of the chromatographic medium;

(ii) an absorber in operable contact with the second end of the chromatographic medium;

(iii) a conductor in operable contact with the first end of the chromatographic medium;

(iv) a conjugate zone containing a specific binding partner to the analyte labeled with a gold sol in a form that can be resolubilized by the addition of an aqueous liquid to the conjugate zone, the conjugate zone being in direct contact with the conductor;

(v) a sample preparation zone, the sample preparation zone being in direct contact with the conjugate zone, the conductor, the conjugate zone, and the sample preparation zone being positioned so that the conjugate zone bridges the sample preparation zone and the conductor; and (vi) a substantially fluid-impermeable barrier layered on top of the first surface of the chromatographic medium and having an aperture for application of liquid to the chromatographic medium, the barrier at least partially blocking application of liquid to the chromatographic medium; and (b) a second opposable component including:

(i) an applicator containing, in a form that can be resolubilized by the addition of an aqueous liquid to the applicator: (1) a soluble silver salt and (2) a reducing agent, the applicator positioned such that when the first and second opposable components are brought into opposition, the applicator is in contact with the barrier so that the resolubilized silver salt and the reducing agent are applied through the aperture in the barrier to the chromatographic medium; and (ii) second and third absorbers positioned such that when the first and second opposable components are brought into opposition, the second absorber and third absorber are in operable contact with portions of the chromatographic medium so that the second and third absorbers remove fluid from the chromatographic medium.

60. The assay device of claim 59 wherein the sample preparation zone contains at least one reagent for treatment of the sample.

61. A method for the detection and/or determination of an analyte in an aqueous test sample comprising:

(a) applying the sample to the sample preparation zone of the assay device of claim 60;

(b) incubating the sample and the sample preparation zone so that at least the one reagent for treatment of the sample can react with the sample to produce a treated sample;

(c) allowing the treated sample to flow through the conjugate zone to resolubilize the labeled specific binding partner in the conjugate zone;

(d) allowing the treated sample and the resolubilized labeled specific binding partner to enter the chromatographic medium through the conductor and to flow through at least the portion of the chromatographic medium including the detection zone;

(e) adding an aqueous liquid to the applicator to resolubilize the soluble silver salt and the reducing agent;

(f) bringing the first and second opposable components into opposition to apply the resolubilized silver salt and the reducing agent to the chromatographic medium through the aperture in the barrier and to bring the second and third absorbers into operable contact with the chromatographic medium to withdraw fluid from the chromatographic medium;

(g) allowing the resolubilized silver salt and reducing agent to flow through at least the portion of the chromatographic medium including the detection zone so that silver is deposited around gold in the gold label of the labeled specific binding partner bound at the detection zone to enhance the signal generated by the label; and (h) detecting and/or determining the analyte in the test sample by observing and/or measuring the labeled specific binding partner bound at the detection zone.

62. The assay device of claim 59 wherein the soluble silver salt is silver lactate and the reducing agent is a quinone.

63. The assay device of claim 59 wherein the first and second opposable components can be placed in opposition so that pressure facilitates application of the resolubilized silver salt and the reducing agent to the chromatographic medium through the aperture.

64. A method for the detection and/or determination of an analyte in an aqueous test sample comprising the steps of:

(a) applying the sample to the sample preparation zone of the assay device of claim 59;

(b) allowing the sample to flow through the conjugate zone to resolubilize the labeled specific binding partner in the conjugate zone;

(c) allowing the sample and the resolubilized labeled specific binding partner to enter the chromatographic medium through the conductor and to flow through at least a portion of the chromatographic medium including the detection zone;

(d) adding an aqueous liquid to the applicator to resolubilize the soluble silver salt and the reducing agent;

(e) bringing the first and second opposable components into opposition to apply the resolubilized silver salt and the reducing agent to the chromatographic medium through the aperture in the barrier and to bring the second and third absorbers into operable contact with the chromatographic medium to withdraw fluid from the chromatographic medium;

(f) allowing the resolubilized silver salt and reducing agent to flow through at least the portion of the chromatographic medium including the detection zone so that silver is deposited around gold in the gold label of the labeled specific binding partner bound at the detection zone to enhance the signal generated by the label; and (g) detecting and/or determining the analyte in the test sample by observing and/or measuring the labeled specific binding partner bound at the detection zone.

65. An assay device for the detection and/or determination of an analyte in a test sample comprising:

(a) a first opposable component including:

(i) a chromatographic medium having a first end, a second end, and first and second surfaces, and having a specific binding partner to the analyte immobilized thereon in a detection zone between the first and second ends of the chromatographic medium;

(ii) an absorber in operable contact with the second end of the chromatographic medium;

(iii) a conductor in operable contact with the first end of the chromatographic medium;

(iv) a conjugate zone containing a specific binding partner to the analyte labeled with a gold sol in a form that can be resolubilized by the addition of an aqueous liquid to the conjugate zone, the conjugate zone being in direct contact with the conductor;

(v) a sample preparation zone, the sample preparation zone being in direct contact with the conjugate zone, the conductor, conjugate zone and sample preparation zone being positioned so that the conjugate zone bridges the sample preparation zone and the conductor; and (vi) a substantially fluid-impermeable barrier layered on top of the first surface of the chromatographic medium and having an aperture for application of liquid to the chromatographic medium, the barrier at least partially blocking application of liquid to the chromatographic medium; and (b) the second opposable component including:
(i) an applicator including two sectors:
(A) a first sector for receiving an aqueous liquid; and
(B) a second sector containing, in a form that can be resolubilized by the addition of an aqueous liquid to the second sector of the applicator: (1) a soluble silver salt and (2) a reducing agent, the applicator positioned so that when the first and second opposable components are brought into opposition, the first sector of the applicator is in direct contact with the aperture in the barrier and the second sector of the applicator is in indirect contact with the aperture so that the aqueous liquid is applied first to the chromatographic medium to provide a wash, followed by the aqueous silver salt and the reducing agent; and (ii) second and third absorbers positioned such that when the first and second opposable components are brought into opposition, the second absorber is in operable contact with a portion of the chromatographic medium between the barrier and the first end of the chromatographic medium and the third absorber is in operable contact with a portion of the chromatographic medium between the barrier and the second end of the chromatographic medium so that the second and third absorbers remove fluid from the chromatographic medium.

66. The assay device of claim 65 wherein the sample preparation zone contains at least one reagent for treatment of the sample.

67. A method for the detection and/or determination of an analyte in an aqueous test sample comprising:

(a) applying the sample to the sample preparation zone of the assay device of claim 66;

(b) incubating the sample in the sample preparation zone so that the at least one reagent for treatment of the sample can react with the sample to produce a treated sample;

(c) allowing the treated sample to flow through the conjugate zone to resolubilize the labeled specific binding partner in the conjugate zone;

(d) allowing the treated sample and the resolubilized labeled specific binding partner to enter the chromatographic medium through the conductor and to flow through at least the portion of the chromatographic medium including the detection zone;

(e) adding an aqueous liquid to the first and second sectors of the applicator to resolubilize the soluble silver salt and the reducing agent in the second sector of the applicator;

(f) bringing the first and second components into opposition to apply the aqueous liquid in the first sector of the applicator to the chromatographic medium through the aperture as a wash, followed by the application of the resolubilized silver salt and the reducing agent to the chromatographic medium, and to bring the second and third absorbers into operable contact with the chromatographic medium to withdraw fluid from the chromatographic medium;

(g) allowing the resolubilized silver salt and reducing agent to flow through at least the portion of the chromatographic medium including the detection zone so that silver is deposited around gold in the gold label of the labeled specific binding partner bound at the detection zone to enhance the signal generated by the label; and (h) detecting and/or determining the analyte in the test sample by observing and/or measuring the labeled specific binding partner bound at the detection zone.

68. The assay device of claim 65 wherein the soluble silver salt is silver lactate and the reducing agent is a quinone.

69. The assay device of claim 65 wherein the first and second opposable components can be placed in opposition so that pressure facilitates application of liquid to the chromatographic medium through the aperture.

70. A method for the detection and/or determination of an analyte in a test sample comprising the steps of:

(a) applying the sample to the sample preparation zone of the assay device of claim 65;

(b) allowing the sample to flow through the conjugate zone to resolubilize the labeled specific binding partner in the conjugate zone;

(c) allowing the sample and the resolubilized label to specific binding partner to enter the chromatographic medium through the conductor and to flow through at least a portion of the chromatographic medium including the detection zone;

(d) adding an aqueous liquid to the first and second sectors of the applicator to resolubilize the soluble silver salt and the reducing agent in the second sector of the applicator;

(e) bringing the first and second components into opposition to apply the aqueous liquid in the first sector of the applicator to the chromatographic medium through the aperture as a wash, followed by the application of the resolubilized silver salt and the reducing agent to the chromatographic medium, and to bring the second and third absorbers into operable contact with the chromatographic medium to withdraw fluid from the chromatographic medium;

(f) allowing the resolubilized silver salt and reducing agent to flow through at least the portion of the chromatographic medium including the detection zone so that silver is deposited around gold in the gold label of the labeled specific binding partner bound at the detection zone to enhance the signal generated by the label; and (g) detecting and/or determining the analyte in the test sample by observing and/or measuring the labeled specific binding partner bound at the detection zone.

71. An assay device for the detection and/or determination of an analyte in a test sample comprising:

(a) a panel including:
(i) a first opposable component including:
(A) a chromatographic medium having a first end, a second end, and first and second surfaces, and having a specific binding partner to the analyte immobilized thereon in a detection zone between the first end and the second end of the chromatographic medium;

(B) a conjugate zone containing a specific binding partner to the analyte labeled with a gold sol in a form that can be resolubilized by the addition of an aqueous liquid to the conjugate zone, the conjugate zone being in operable contact with the first end of the chromatographic medium;

(C) a conductor in operable contact with the conjugate zone, the conjugate zone bridging the first end of the chromatographic medium and the conductor; and (D) a substantially fluid-impermeable barrier layered on top of the first surface of the chromatographic medium and having an aperture for application of liquid to the chromatographic medium, the barrier at least partially blocking application of liquid to the chromatographic medium;

(ii) a second opposable component including:

(A) a first receptacle for a swab which may contain a test sample;

(B) a well for addition of at least one extraction reagent to the swab; and (C) a first absorber separated from the first receptacle and the well; and (iii) a second receptacle for holding a protrusion of an insert to align the insert with the first and second opposable components; the first and second opposable components of the panel being configured so that, when they are brought into opposition, the first absorber is brought into contact with a portion of the chromatographic medium, and the first receptacle is brought into contact with the conductor; and (b) an insert including:

(i) an applicator containing, in a form that can be resolubilized by the addition of an aqueous liquid to the applicator: (1) a soluble silver salt and (2) a reducing agent;

(ii) a second absorber;

(iii) a third absorber; and (iv) a protrusion for insertion into the second receptacle of the panel; the insert configured so that when the protrusion is inserted into the second receptacle of the panel, the applicator is in operable contact with the aperture to apply the contents of the applicator to the chromatographic medium through the aperture, and the second and third absorbers are each in operable contact with a portion of the chromatographic medium to withdraw fluid from the chromatographic medium.

72. The assay device of claim 71 wherein the soluble silver salt is silver lactate and the reducing agent is a quinone.

73. The assay device of claim 71 wherein the first and second opposable components can be placed in opposition so that pressure facilitates application of the liquid to the chromatographic medium through the aperture.

74. A method for the detection and/or determination of an analyte in an aqueous test sample comprising the steps of:

(a) placing a swab containing a test sample in the first receptacle of the assay device of claim 71;

(b) applying at least one extraction reagent to the well to extract analyte from the swab;

(c) bringing the first and second opposable components into opposition so that the swab in the receptacle is in contact with the conductor to apply the extracted analyte with the conductor and so that the first absorber is in contact with a portion of the chromatographic medium;

(d) allowing the extracted sample to flow through the conjugate zone to resolubilize the labeled specific binding partner in the conjugate zone;

(e) allowing the extracted sample and the resolubilized labeled specific binding partner to enter the chromatographic medium and to flow through at least the portion of the chromatographic medium including the detection zone;

(f) adding an aqueous liquid to the applicator of the insert to resolubilize the soluble silver salt and the reducing agent;

(g) inserting the protrusion of the insert into the second receptacle of the panel and positioning the insert so that the applicator is in contact with the aperture in the barrier to apply the contents of the applicator to the chromatographic medium through the aperture and so that the second and third absorbers are in contact with the chromatographic medium to withdraw fluid from the chromatographic medium;

(h) allowing the resolubilized silver salt and reducing agent to flow through at least the portion of the chromatographic medium including the detection zone so that the silver is deposited around gold in the gold label of the labeled specific binding partner bound at the detection zone to enhance the signal generated by the label; and (i) detecting and/or determining the analyte in the test sample by observing and/or measuring the labeled specific binding partner bound at the detection zone.

75. An assay device for the detection and/or determination of an analyte in a test sample comprising:

(a) a panel including:

(i) a first opposable component including:

(A) a chromatographic medium having a first end, a second end, and first and second surfaces and having a specific binding partner to the analyte immobilized thereon in a detection zone between the first and second ends of the chromatographic medium and substantially smaller than the area of the chromatographic medium;

(B) a conductor in operable contact with the first end of the chromatographic medium; and (C) a substantially fluid-impermeable barrier layered on top of the first surface of the chromatographic medium and having an aperture for application of liquid to the chromatographic medium, the barrier at least partially blocking application of liquid to the chromatographic medium;

(ii) a second opposable component including a first absorber, the first and second opposable components being configured so that when they are brought into opposition the first absorber is brought into operable contact with a portion of the chromatographic medium so that the first absorber contacts the chromatographic medium on the opposite side of the detection zone from the conductor; and (iii) a receptacle for holding a protrusion of an insert to align the insert with the first and second opposable components; and (b) an insert including:

(i) an applicator containing, in a form that can be resolubilized by the addition of an aqueous liquid to the applicator, a substrate for an enzyme label that is bound to a specific binding partner to the analyte, the enzyme label producing an insoluble detectable product by catalysis of a reaction involving the substrate;

(ii) a second absorber;

(iii) a third absorber; and (iv) a protrusion for insertion into the receptacle of the panel; the insert configured so that when the protrusion is inserted into the receptacle of the panel, the applicator is in operable contact with the aperture to apply the contents of the applicator to the chromatographic medium through the aperture, and the second and third absorbers are each in operable contact with a portion of the chromatographic medium to withdraw fluid from the chromatographic medium.

76. The assay device of claim 75 wherein the first and second opposable components can be placed in opposition so that pressure facilitates application of the contents of the applicator to the chromatographic medium through the aperture.

77. A method for the detection and/or determination of an analyte in a test sample comprising the steps of:

(a) adding to an aqueous test sample a labeled specific binding partner to the analyte, the label of the labeled specific binding partner being an enzyme catalyzing a reaction producing an insoluble detectable product, to form a sample-label solution;

(b) applying the sample-label solution to the conductor of the assay device of claim 75;

(c) bringing the first and second opposable components into opposition to bring the first absorber into operable contact with a portion of the chromatographic medium;

(d) allowing the sample-label solution to enter the chromatographic medium and to flow through at least the portion of the chromatographic medium including the detection zone;

(e) adding an aqueous liquid to the applicator of the insert to resolubilize the substrate;

(f) inserting the protrusion of the insert into the receptacle of the panel and positioning the insert so that the applicator is in contact with the aperture and the barrier to apply the contents of the applicator to the chromatographic medium through the aperture and so that the second and third absorbers are placed in contact with the chromatographic medium to withdraw fluid from the chromatographic medium;

(g) allowing the resolubilized substrate to flow through at least the portion of the chromatographic medium including the detection zone, so that the enzyme of the enzyme label catalyzes a reaction involving the substrate and depositing an insoluble product as a signal of the label; and (h) detecting and/or determining the analyte in the test sample by observing and/or measuring the labeled specific binding partner bound at the detection zone based on the insoluble product deposited as a signal.

78. An assay device for the detection and/or determination of an analyte in a test sample comprising:

(a) a panel including:

(i) a first opposable component including:

(A) a chromatographic medium having a first end, a second end, and first and second surfaces, and having a specific binding partner to the analyte immobilized thereon in a detection zone between the first and second ends of the chromatographic medium;

(B) a conjugate zone containing a specific binding partner to the analyte labeled with an enzyme in a form that can be resolubilized by the addition of an aqueous liquid to the conjugate zone, the conjugate zone being in contact with the first end of the chromatographic medium;

(C) a conductor in direct contact with the conjugate zone, the conjugate zone bridging the first end of the chromatographic medium and the conductor; and (D) a substantially fluid-impermeable barrier layered on top of the first surface of the chromatographic medium and having an aperture for application of liquid to the chromatographic medium, the barrier at least partially blocking application of liquid to the chromatographic medium;

(ii) a second opposable component including:

(A) a first receptacle for a swab containing a test sample;

(B) a well for addition of at least one extraction reagent to the swab; and (C) a first absorber separated from the first receptacle and the well; and (iii) a second receptacle for holding a protrusion of an insert to align the insert with the first and second opposable components; the first and second opposable components being configured so that when they are brought into opposition, the first absorber is brought into contact with a portion of the chromatographic medium so that the first absorber contacts the chromatographic medium on the opposite side of the detection zone from the conductor and the first receptacle is brought into contact with the conductor; and (b) an insert including:

(i) an applicator containing, in a form that can be resolubilized by the addition of an aqueous liquid to the applicator, a substrate for the enzyme label bound to the specific binding partner to the analyte in the conjugate zone, the enzyme label producing a insoluble detectable product by catalysis of a reaction involving the substrate;

(ii) a second absorber;

(iii) a third absorber; and (iv) a protrusion for insertion into the second receptacle of the panel; the protrusion configured such that when the protrusion is inserted into the second receptacle of the panel, the applicator is in contact with the aperture to apply the contents of the applicator to the chromatographic medium through the aperture, and the second and third absorbers are each in contact with a portion of the chromatographic medium to withdraw fluid from the chromatographic medium.

79. The assay device of claim 78 wherein the first and second opposable components can be placed in opposition so that pressure facilitates application of the contents of the applicator to the chromatographic medium through the aperture.

80. A method for the detection and/or determination of an analyte in a test sample comprising the steps of:

(a) placing a swab containing a test sample in the first receptacle of the assay device of claim 78;

(b) applying at least one extraction reagent to the well to extract analyte from the swab;

(c) bringing the first and second opposable components into opposition so that the swab in the first receptacle is in contact with the conductor to apply the extracted analyte to the conductor and so that the first absorber is in contact with a portion of the chromatographic medium;

(d) allowing the extracted sample to flow through the conjugate zone to resolubilize the labeled specific binding partner in the conjugate zone;

(e) allowing the extracted sample and the resolubilized labeled specific binding partner to enter the chromatographic medium and to flow through at least the portion of the chromatographic medium including the detection zone;

(f) adding an aqueous liquid to the applicator of the insert to resolubilize the substrate;

(g) inserting the protrusion of the insert into the second receptacle of the panel and positioning the insert so that the applicator is in contact with the aperture and the barrier to apply the contents of the applicator to the chromatographic medium through the aperture and so that the second and third absorbers are in contact with the chromatographic medium to withdraw fluid from the chromatographic medium;

(h) allowing the resolubilized substrate to flow through at least a portion of the chromatographic medium including the detection zone so that the enzyme of the enzyme label catalyzes a reaction involving the substrate and depositing an insoluble product that is a signal of the label; and (i) detecting and/or determining the analyte in the test sample by observing and/or measuring the labeled specific binding partner bound at the detection zone by means of the insoluble product deposited as a signal.

81. An assay device for the detection and/or determination of an analyte in a test sample comprising:

(a) a first opposable component including:

(i) the chromatographic medium having a first end, a second end, and first and second surfaces, and having a specific binding partner to the analyte immobilized thereon in a detection zone between the first and second ends of the chromatographic medium;

(ii) at least one absorber in operable contact with the one of the ends of the chromatographic medium;

(iii) a first substantially fluid-impermeable barrier layered on top of the first surface of the chromatographic medium and having a first aperture therethrough for application of liquid to the chromatographic medium;

(iv) a distribution membrane adjacent to the first substantially fluid-impermeable barrier to direct fluid to the first aperture in the first substantially fluid-impermeable barrier, the distribution membrane having a central portion and a portion surrounding the central portion;

(v) a second substantially fluid-impermeable barrier layered on top of the central portion of the distribution membrane;

(vi) an applicator containing a labeled specific binding partner to the analyte in resolubilizable form and layered on top of the second substantially fluid impermeable barrier and extending to make operable contact with the portion surrounding the central portion of the distribution membrane so that fluid can flow from the applicator around the second barrier to the portion of the distribution membrane surrounding the central portion; and (vii) a surface barrier containing a second aperture therethrough for application of liquid to the applicator; and (b) a second opposable component including a receptacle for a swab containing a test sample.

82. The assay device of claim 81 wherein the label of the labeled specific binding partner is a visually detectable label.

83. The assay device of claim 81 wherein the first and second opposable components can be placed in opposition so that pressure facilitates application of liquid to the chromatographic medium through the aperture.

84. A test kit for the detection and/or determination of an analyte in a test sample comprising, in separate containers:

(a) the assay device of claim 83; and (b) at least one reagent for the extraction of analyte from the swab.

85. A method for the detection and/or determination of an analyte in a test sample comprising the steps of:

(a) placing a swab containing a test sample in the receptacle of the assay device of claim 83;

(b) applying at least one extraction reagent to the swab in the receptacle to extract analyte from the swab;

(c) bringing the first and second opposable components into opposition to apply the extracted analyte to the second aperture in the surface barrier and then to the applicator and chromatographic medium after passing around the second barrier and through the distribution membrane, thereby resolubilizing the labeled specific binding partner in the applicator;

(d) allowing the sample and the resolubilized labeled specific binding partner to the analyte to flow through at least the portion of the chromatographic medium including the detection zone; and (e) detecting and/or determining the analyte in the test sample by observing and/or measuring the labeled detection reagent bound at the detection zone.

* * * * *